(12) United States Patent
Dotti et al.

(10) Patent No.: US 10,519,214 B2
(45) Date of Patent: Dec. 31, 2019

(54) METHODS AND COMPOSITIONS FOR CHIMERIC ANTIGEN RECEPTOR TARGETING CANCER CELLS

(71) Applicants: The University of North Carolina at Chapel Hill, Chapel Hill, NC (US); The General Hospital Corporation, Boston, MA (US)

(72) Inventors: Gianpietro Dotti, Chapel Hill, NC (US); Soldano Ferrone, Boston, MA (US); Hongwei Du, Chapel Hill, NC (US); Xinhui Wang, Boston, MA (US); Cristina Ferrone, Boston, MA (US)

(73) Assignees: The University of North Carolina at Chapel Hill, Chapel Hill, NC (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 16/262,490

(22) Filed: Jan. 30, 2019

(65) Prior Publication Data

US 2019/0153063 A1    May 23, 2019

Related U.S. Application Data

(63) Continuation of application No. 16/012,432, filed on Jun. 19, 2018, now Pat. No. 10,233,226.

(60) Provisional application No. 62/523,105, filed on Jun. 21, 2017.

(51) Int. Cl.
| | | |
|---|---|---|
| *C07K 14/705* | (2006.01) |
| *A61P 35/00* | (2006.01) |
| *G01N 33/574* | (2006.01) |
| *A61K 35/17* | (2015.01) |
| *A61K 38/00* | (2006.01) |

(52) U.S. Cl.
CPC ........ *C07K 14/70521* (2013.01); *A61K 35/17* (2013.01); *A61P 35/00* (2018.01); *C07K 14/70532* (2013.01); *C07K 14/70596* (2013.01); *G01N 33/574* (2013.01); *G01N 33/57492* (2013.01); *A61K 38/00* (2013.01)

(58) Field of Classification Search
CPC ............................................. C07K 14/70521
See application file for complete search history.

(56) References Cited

U.S. PATENT DOCUMENTS

| | | | |
|---|---|---|---|
| 4,444,887 A | 4/1984 | Hoffmann |
| 4,716,111 A | 12/1987 | Osband et al. |
| 4,946,778 A | 8/1990 | Ladner et al. |
| 5,225,539 A | 7/1993 | Winter |
| 5,258,498 A | 11/1993 | Huston et al. |
| 5,413,923 A | 5/1995 | Kucherlapati et al. |
| 5,530,101 A | 6/1996 | Queen et al. |
| 5,545,806 A | 8/1996 | Lonberg et al. |
| 5,565,332 A | 10/1996 | Hoogenboom et al. |
| 5,569,825 A | 10/1996 | Lonberg et al. |
| 5,585,089 A | 12/1996 | Queen et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,814,318 A | 9/1998 | Lonberg et al. |
| 5,939,598 A | 8/1999 | Kucherlapati et al. |
| 6,420,377 B1 | 7/2002 | Lee et al. |
| 6,537,988 B2 | 3/2003 | Lee |
| 8,399,645 B2 * | 3/2013 | Campana ........... C07K 16/2866 536/23.4 |
| 10,233,226 B2 * | 3/2019 | Dotti ................ C07K 14/70521 |
| 2016/0038578 A1 | 2/2016 | Wang et al. |
| 2016/0053017 A1 | 2/2016 | Orentas et al. |
| 2016/0303124 A1 | 10/2016 | Webster et al. |

FOREIGN PATENT DOCUMENTS

| | | | |
|---|---|---|---|
| EP | 0519596 | 12/1992 |
| EP | 0592106 | 4/1994 |
| WO | 2012079000 | 6/2012 |
| WO | 2016044383 | 3/2016 |
| WO | 2017044699 | 3/2017 |
| WO | WO2017/062672 | * 4/2017 ............. A61K 16/68 |

OTHER PUBLICATIONS

Leitner et al. (Eur J Immunol. Jul. 2009 ; 39(7): 1754-1764) (Year: 2009).*
Altschul et al. "Basic Local Alignment Search Tool" The Journal of Molecular Biology, 215:403-410 (1990).
Altschul et al. "Gapped BLAST and PSI-BLAST: a new generation of protein database search programs" Nucleic Acids Research, 25(17):3389-3402 (1997).
Bird et al. "Single-Chain Antigen-Binding Proteins" Science, 242:423-426 (1988).
Fauci et al. "Monoclonal antibody-based immunotherapy of ovarian cancer: targeting ovarian cancer cells with the B7-H3-specific mAb 376.96" Gynecologic Oncology, 132(1):203-210 (2014) (Abstract only).
Gonnet et al. "Exhaustive Matching of the Entire Protein Sequence Database" Science, 256:1443-1445 (1992).
Greenspan et al. "Idiotypes: structure and immunogenicity" FASEB Journal, 7(5):437-444 (1989) (Abstract only).
Holliger et al. "'Diabodies': small bivalent and bispecific antibody fragments" Proceedings of the National Academy of Sciences USA, 90:6444-6448 (1993).
Huston et al. "Protein engineering of antibody binding sites: recovery of specific activity in an anti-digoxin single-chain Fv analogue produced in *Escherichia coli*" Proceedings of the National Academy of Sciences USA, 85:5879-5883 (1988).
Huston et al. "Protein engineering of single-chain Fv analogs and fusion proteins" Methods in Enzymology, 203:46-52 (1991) (Abstract only).
Imai et al. "A 94,000-dalton glycoprotein expressed by human melanoma and carcinoma cells" Journal of the National Cancer Institute, 68(5):761-769 (1982) (Abstract only).

(Continued)

*Primary Examiner* — Scott Long
(74) *Attorney, Agent, or Firm* — Lisa M. Warren, Esq.; Morse, Barnes-Brown & Pendleton, P.C.

(57) ABSTRACT

The present invention provides a chimeric antigen receptor (CAR) that recognizes B7-H3 (CD276), as well as methods of use in the treatment of diseases and disorders.

22 Claims, 29 Drawing Sheets

Specification includes a Sequence Listing.

(56) References Cited

OTHER PUBLICATIONS

Jespers et al. "Guiding the selection of human antibodies from phage display repertoires to a single epitope of an antigen" Bio/technology, 12:899-903 (1988) (Abstract only).
Kasten et al. "B7-H3-targeted 212Pb radioimmunotherapy of ovarian cancer in preclinical models" Nuclear Medicine and Biology, 47:23-30 (2017) (Abstract only).
Langstein et al. "CD137 (ILA/4-1BB), a Member of the TNF Receptor Family, Induces Monocyte Activation via Bidirectional Signaling" The Journal of Immunology, 160:2488-2494 (1998).
Lonberg et al. "Human antibodies from transgenic mice" International Reviews of Immunology, 13:65-93 (1995) (Abstract only).
Nissinoff, Alfred "Idiotypes: concepts and applications" The Journal of Immunology, 147(8):2429-2438 (1991).
Padlan, E. "A possible procedure for reducing the immunogenicity of antibody variable domains while preserving their ligand-binding properties" Molecular Immunology, 28(4-5):489-498 (1991) (Abstract only).
Pearson, William R. "Using the FASTA Program to Search Protein and DNA Sequence Databases" Methods in Molecular Biology, 24:307-331 (1994).
Riechmann et al. "Reshaping human antibodies for therapy" Nature, 332:323-327 (1988) (Abstract only).
Roguska et al. "Humanization of murine monoclonal antibodies through variable domain resurfacing" Proceedings of the National Academy of Sciences, 91:969-973 (1994).
Rosenberg et al. "Use of Tumor-Infiltrating Lymphocytes and Interleukin-2 in the Immunotherapy of Patients with Metastatic Melanoma" The New England Journal of Medicine, 319:1676-1680 (1988) (Abstract only).
Rosenberg, Steven A. "The Immunotherapy of Solid Cancers Based on Cloning the Genes Encoding Tumor-Rejection Antigens" Annual Review of Medicine, 47:481-491 (1996).
Shu et al. "Secretion of a single-gene-encoded immunoglobulin from myeloma cells" Proceedings of the National Academy of Sciences USA, 90:7995-7999 (1993).
Skerra et al. "Assembly of a functional immunoglobulin Fv fragment in *Escherichia coli*" Science, 240(4855):1038-1041 (1988) (Abstract only).
Studnicka et al. "Human-engineered monoclonal antibodies retain full specific binding activity by preserving non-CDR complementarity-modulating residues" Protein Engineering, 7(6):805-814 (1994).
Ward et al. "Binding activities of a repertoire of single immunoglobulin variable domains secreted from *Escherichia coli*" Nature, 241:544-546 (1989).
International Search Report and the Written Opinion of the International Searching Authority corresponding to International Patent Application No. PCT/US2018/038289 (8 pages) (dated Dec. 27, 2018).
Theruvath et al. "IMMU-07. Checkpoint Molecule B7-H3 is Highly Expressed on Medulloblastoma and Proves to be a Promising Candidate for CAR T Cell Immunotherapy" Neuro-Oncology, 19(Suppl. 4):iv28-iv29 (2017).

\* cited by examiner

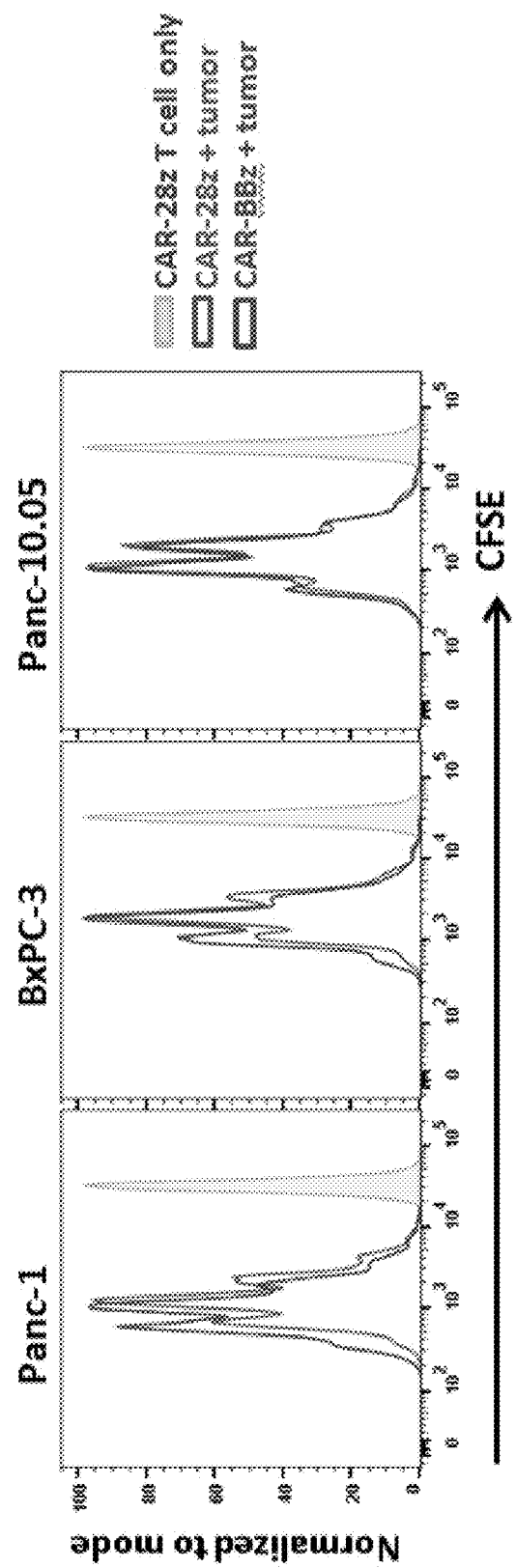

1. Map of the plasmid

2. DNA sequence of the whole plasmid.

AAGCTTTGCTCTTAGGAGTTTCCTAATACATCCCAAACTCAAATATATAAAGCAT
TTGACTTGTTCTATGCCCTAGGGGGCGGGGGGAAGCTAAGCCAGCTTTTTTTAAC
ATTTAAAATGTTAATTCCATTTTAAATGCACAGATGTTTTTATTTCATAAGGGTTT
CAATGTGCATGAATGCTGCAATATTCCTGTTACCAAAGCTAGTATAAATAAAAAT
AGATAAACGTGGAAATTACTTAGAGTTTCTGTCATTAACGTTTCCTTCCTCAGTTG
ACAACATAAATGCGCTGCTGAGCAAGCCAGTTTGCATCTGTCAGGATCAATTTCC
CATTATGCCAGTCATATTAATTACTAGTCAATTAGTTGATTTTTATTTTTGACATA
TACATGTGAATGAAAGACCCCACCTGTAGGTTTGGCAAGCTAGCTTAAGTAACGC
CATTTTGCAAGGCATGGAAAAATACATAACTGAGAATAGAAAAGTTCAGATCAA
GGTCAGGAACAGATGGAACAGCTGAATATGGGCCAAACAGGATATCTGTGGTAA
GCAGTTCCTGCCCCGGCTCAGGGCCAAGAACAGATGGAACAGCTGAATATGGGC
CAAACAGGATATCTGTGGTAAGCAGTTCCTGCCCCGGCTCAGGGCCAAGAACAG
ATGGTCCCCAGATGCGGTCCAGCCCTCAGCAGTTTCTAGAGAACCATCAGATGTT
TCCAGGGTGCCCCAAGGACCTGAAATGACCCTGTGCCTTATTTGAACTAACCAAT
CAGTTCGCTTCTCGCTTCTGTTCGCGCGCTTATGCTCCCGAGCTCAATAAAAGA
GCCCACAACCCCTCACTCGGGGCGCCAGTCCTCCGATTGACTGAGTCGCCCGGGT
ACCCGTGTATCCAATAAACCCTCTTGCAGTTGCATCCGACTTGTGGTCTCGCTGTT
CCTTGGGAGGGTCTCCTCTGAGTGATTGACTACCCGTCAGCGGGGGTCTTTCATT
TGGGGGCTCGTCCGGGATCGGGAGACCCCTGCCCAGGGACCACCGACCCACCAC
CGGGAGGTAAGCTGGCCAGCAACTTATCTGTGTCTGTCCGATTGTCTAGTGTCTA
TGACTGATTTTATGCGCCTGCGTCGGTACTAGTTAGCTAACTAGCTCTGTATCTGG
CGGACCCGTGGTGGAACTGACGAGTTCGGAACACCCGGCCGCAACCCTGGGAGA
CGTCCCAGGGACTTCGGGGGCCGTTTTGTGGCCCGACCTGAGTCCTAAAATCCC
GATCGTTTAGGACTCTTTGGTGCACCCCCTTAGAGGAGGGATATGTGGTTCTGG
TAGGAGACGAGAACCTAAAACAGTTCCCGCCTCCGTCTGAATTTTTGCTTTCGGT
TTGGGACCGAAGCCGCGCCGCGCGTCTTGTCTGCTGCAGCATCGTTCTGTGTTGT
CTCTGTCTGACTGTGTTTCTGTATTTGTCTGAAAATATGGGCCCGGGCTAGCCTGT
TACCACTCCCTTAAGTTTGACCTTAGGTCACTGGAAAGATGTCGAGCGGATCGCT
CACAACCAGTCGGTAGATGTCAAGAAGAGACGTTGGGTTACCTTCTGCTCTGCAG
AATGGCCAACCTTTAACGTCGGATGGCCGCGAGACGGCACCTTTAACCGAGACC
TCATCACCCAGGTTAAGATCAAGGTCTTTTCACCTGGCCCGCATGGACACCCAGA
CCAGGTGGGGTACATCGTGACCTGGGAAGCCTTGGCTTTTGACCCCCCTCCCTGG
GTCAAGCCCTTTGTACACCCTAAGCCTCCGCCTCCTCTTCCTCCATCCGCCCCGTC
TCTCCCCCTTGAACCTCCTCGTTCGACCCCGCCTCGATCCTCCCTTTATCCAGCCC
TCACTCCTTCTCTAGGCGCCCCCATATGGCCATATGAGATCTTATATGGGGCACC
CCCGCCCCTTGTAAACTTCCCTGACCCTGACATGACAAGAGTTACTAACAGCCCC
TCTCTCCAAGCTCACTTACAGGCTCTCTACTTAGTCCAGCACGAAGTCTGGAGAC
CTCTGGCGGCAGCCTACCAAGAACAACTGGACCGACCGGTGGTACCTCACCCTT
ACCGAGTCGGCGACACAGTGTGGGTCCGCCGACACCAGACTAAGAACCTAGAAC
CTCGCTGGAAAGGACCTTACACAGTCCTGCTGACCACCCCCACCGCCCTCAAAGT
AGACGGCATCGCAGCTTGGATACACGCCGCCCACGTGAAGGCTGCCGACCCCGG
GGGTGGACCATCCTCTAGACTGCCATGGAATTCGGCCTGAGCTGGCTGTTCCTGG
TGGCCATCCTGAAGGGCGTGCAGTGCGACATTGTGATGACCCAGTCTCACAAATT
CATGTCCACATCAATTGGAGCCAGGGTCAGCATCACCTGCAAGGCCAGTCAGGA
TGTGAGAACTGCTGTAGCCTGGTATCAACAGAAACCAGGCCAGTCTCCTAAACTA
CTAATTTACTCGGCATCCTACCGGTACACTGGAGTCCCTGATCGCTTCACTGGCA
GTGGATCTGGGACGGATTTCACTTTCACCATCAGCAGTGTGCAGGCTGAAGACCT
GGCAGTTTATTACTGTCAGCAACATTATGGTACTCCTCCGTGGACGTTCGGTGGA
GGCACCAAGCTGGAAATCAAAGGCGGCGGAGGATCTGGCGGAGGCGGAAGTGG

Figure 7 (continued)

```
CGGAGGGGGCTCTGAAGTGCAGCTGGTGGAGTCTGGGGGAGGCTTAGTGAAGCC
TGGAGGGTCCCTGAAACTCTCCTGTGAAGCCTCTAGATTCACTTTCAGTAGCTAT
GCCATGTCTTGGGTTCGCCAGACTCCGGAGAAGAGGCTGGAGTGGGTCGCAGCC
ATTAGTGGAGGTGGTAGGTACACCTACTATCCAGACAGTATGAAGGGTCGATTC
ACCATCTCCAGAGACAATGCCAAGAATTTCCTGTACCTGCAAATGAGCAGTCTGA
GGTCTGAGGACACGGCCATGTATTACTGTGCAAGACACTATGATGGTTATCTTGA
CTACTGGGGCCAAGGCACCACTCTCACAGTCTCCTCAACGCGTACCACGACGCCA
GCGCCGCGACCACCAACACCGGCGCCCACCATCGCGTCGCAGCCCCTGTCCCTGC
GCCCAGAGGCGTGCCGGCCAGCGGCGGGGGGCGCAGTGCACACGAGGGGGCTG
GACTTCGCCTGTGATATCTACATCTGGGCGCCCTTGGCCGGGACTTGTGGGGTCC
TTCTCCTGTCACTGGTTATCACCCTTTACTGCAGGAGTAAGAGGAGCAGGCTCCT
GCACAGTGACTACATGAACATGACTCCCCGCCGCCCCGGGCCCACCCGCAAGCA
TTACCAGCCCTATGCCCCACCACGCGACTTCGCAGCCTATCGCTCCAGAGTGAAG
TTCAGCAGGAGCGCAGACGCCCCGCGTACCAGCAGGGCCAGAACCAGCTCTAT
AACGAGCTCAATCTAGGACGAAGAGAGGAGTACGATGTTTTGGACAAGAGACGT
GGCCGGGACCCTGAGATGGGGGGAAAGCCGAGAAGGAAGAACCCTCAGGAAGG
CCTGTACAATGAACTGCAGAAAGATAAGATGGCGGAGGCCTACAGTGAGATTGG
GATGAAAGGCGAGCGCCGGAGGGGCAAGGGGCACGATGGCCTTTACCAGGGTCT
CAGTACAGCCACCAAGGACACCTACGACGCCCTTCACATGCAGGCCCTGCCCCCT
CGCTAAGCATGCACCTCGAGATCGATCCGGATTAGTCCAATTTGTTAAAGACAGG
ATATCAGTGGTCCAGGCTCTAGTTTTGACTCAACAATATCACCAGCTGAAGCCTA
TAGAGTACGAGCCATAGATAAAATAAAAGATTTTATTTAGTCTCCAGAAAAAGG
GGGGAATGAAAGACCCCACCTGTAGGTTTGGCAAGCTAGCTTAAGTAACGCCAT
TTTGCAAGGCATGGAAAAATACATAACTGAGAATAGAGAAGTTCAGATCAAGGT
CAGGAACAGATGGAACAGCTGAATATGGGCCAAACAGGATATCTGTGGTAAGCA
GTTCCTGCCCCGGCTCAGGGCCAAGAACAGATGGAACAGCTGAATATGGGCCAA
ACAGGATATCTGTGGTAAGCAGTTCCTGCCCCGGCTCAGGGCCAAGAACAGATG
GTCCCCAGATGCGGTCCAGCCCTCAGCAGTTTCTAGAGAACCATCAGATGTTTCC
AGGGTGCCCCAAGGACCTGAAATGACCCTGTGCCTTATTTGAACTAACCAATCAG
TTCGCTTCTCGCTTCTGTTCGCGCGCTTCTGCTCCCCGAGCTCAATAAAAGAGCCC
ACAACCCCTCACTCGGGGCGCCAGTCCTCCGATTGACTGAGTCGCCCGGGTACCC
GTGTATCCAATAAACCCTCTTGCAGTTGCATCCGACTTGTGGTCTCGCTGTTCCTT
GGGAGGGTCTCCTCTGAGTGATTGACTACCCGTCAGCGGGGGTCTTTCACACATG
CAGCATGTATCAAAATTAATTTGGTTTTTTTTCTTAAGTATTTACATTAAATGGCC
ATAGTACTTAAAGTTACATTGGCTTCCTTGAAATAAACATGGAGTATTCAGAATG
TGTCATAAATATTTCTAATTTTAAGATAGTATCTCCATTGGCTTTCTACTTTTTCTT
TTATTTTTTTTGTCCTCTGTCTTCCATTTGTTGTTGTTGTTGTTTGTTTGTTTGTTT
GTTGGTTGGTTGGTTAATTTTTTTTTAAAGATCCTACACTATAGTTCAAGCTAGAC
TATTAGCTACTCTGTAACCCAGGGTGACCTTGAAGTCATGGGTAGCCTGCTGTTT
TAGCCTTCCCACATCTAAGATTACAGGTATGAGCTATCATTTTTGGTATATTGATT
GATTGATTGATTGATGTGTGTGTGTGATTGTGTTTGTGTGTGTGACTGTGAAAA
TGTGTGTATGGGTGTGTGTGAATGTGTGTATGTATGTGTGTGTGAGTGTGTGT
GTGTGTGTGTGCATGTGTGTGTGTGACTGTGTCTATGTGTATGACTGTGTGTGT
GTGTGTGTGTGTGTGTGTGTGTGTGTGTGTGTGTTGTGAAAAAATATTCTAT
GGTAGTGAGAGCCAACGCTCCGGCTCAGGTGTCAGGTTGGTTTTGAGACAGAGT
CTTTCACTTAGCTTGGAATTCACTGGCCGTCGTTTACAACGTCGTGACTGGGAA
AACCCTGGCGTTACCCAACTTAATCGCCTTGCAGCACATCCCCCTTTCGCCAGCT
GGCGTAATAGCGAAGAGGCCCGCACCGATCGCCCTTCCCAACAGTTGCGCAGCC
TGAATGGCGAATGGCGCCTGATGCGGTATTTCTCCTTACGCATCTGTGCGGTAT
TCACACCGCATATGGTGCACTCTCAGTACAATCTGCTCTGATGCCGCATAGTTA
```

Figure 7 (continued)

AGCCAGCCCCGACACCCGCCAACACCCGCTGACGCGCCCTGACGGGCTTGTCTG
CTCCCGGCATCCGCTTACAGACAAGCTGTGACCGTCTCCGGGAGCTGCATGTGTC
AGAGGTTTTCACCGTCATCACCGAAACGCGCGATGACGAAAGGGCCTCGTGATA
CGCCTATTTTTATAGGTTAATGTCATGATAATAATGGTTTCTTAGACGTCAGGTGG
CACTTTTCGGGGAAATGTGCGCGGAACCCCTATTTGTTTATTTTTCTAAATACATT
CAAATATGTATCCGCTCATGAGACAATAACCCTGATAAATGCTTCAATAATATTG
AAAAAGGAAGAGTATGAGTATTCAACATTTCCGTGTCGCCCTTATTCCCTTTTTG
CGGCATTTTGCCTTCCTGTTTTGCTCACCCAGAAACGCTGGTGAAAGTAAAAGA
TGCTGAAGATCAGTTGGGTGCACGAGTGGGTTACATCGAACTGGATCTCAACAG
CGGTAAGATCCTTGAGAGTTTTCGCCCCGAAGAACGTTTTCCAATGATGAGCACT
TTTAAAGTTCTGCTATGTGGCGCGGTATTATCCCGTATTGACGCCGGGCAAGAGC
AACTCGGTCGCCGCATACACTATTCTCAGAATGACTTGGTTGAGTACTCACCAGT
CACAGAAAAGCATCTTACGGATGGCATGACAGTAAGAGAATTATGCAGTGCTGC
CATAACCATGAGTGATAACACTGCGGCCAACTTACTTCTGACAACGATCGGAGG
ACCGAAGGAGCTAACCGCTTTTTTGCACAACATGGGGGATCATGTAACTCGCCTT
GATCGTTGGGAACCGGAGCTGAATGAAGCCATACCAAACGACGAGCGTGACACC
ACGATGCCTGTAGCAATGGCAACAACGTTGCGCAAACTATTAACTGGCGAACTA
CTTACTCTAGCTTCCCGGCAACAATTAATAGACTGGATGGAGGCGGATAAAGTTG
CAGGACCACTTCTGCGCTCGGCCCTTCCGGCTGGCTGGTTTATTGCTGATAAATCT
GGAGCCGGTGAGCGTGGGTCTCGCGGTATCATTGCAGCACTGGGGCCAGATGGT
AAGCCCTCCCGTATCGTAGTTATCTACACGACGGGGAGTCAGGCAACTATGGATG
AACGAAATAGACAGATCGCTGAGATAGGTGCCTCACTGATTAAGCATTGGTAAC
TGTCAGACCAAGTTTACTCATATATACTTTAGATTGATTTAAAACTTCATTTTTAA
TTTAAAAGGATCTAGGTGAAGATCCTTTTTGATAATCTCATGACCAAAATCCCTT
AACGTGAGTTTTCGTTCCACTGAGCGTCAGACCCCGTAGAAAAGATCAAAGGAT
CTTCTTGAGATCCTTTTTTTCTGCGCGTAATCTGCTGCTTGCAAACAAAAAAACCA
CCGCTACCAGCGGTGGTTTGTTTGCCGGATCAAGAGCTACCAACTCTTTTTCCGA
AGGTAACTGGCTTCAGCAGAGCGCAGATACCAAATACTGTCCTTCTAGTGTAGCC
GTAGTTAGGCCACCACTTCAAGAACTCTGTAGCACCGCCTACATACCTCGCTCTG
CTAATCCTGTTACCAGTGGCTGCTGCCAGTGGCGATAAGTCGTGTCTTACCGGGT
TGGACTCAAGACGATAGTTACCGGATAAGGCGCAGCGGTCGGGCTGAACGGGGG
GTTCGTGCACACAGCCCAGCTTGGAGCGAACGACCTACACCGAACTGAGATACC
TACAGCGTGAGCATTGAGAAAGCGCCACGCTTCCCGAAGGGAGAAAGGCGGACA
GGTATCCGGTAAGCGGCAGGGTCGGAACAGGAGAGCGCACGAGGGAGCTTCCA
GGGGGAAACGCCTGGTATCTTTATAGTCCTGTCGGGTTTCGCCACCTCTGACTTG
AGCGTCGATTTTTGTGATGCTCGTCAGGGGGCGGAGCCTATGGAAAAACGCCA
GCAACGCGGCCTTTTTACGGTTCCTGGCCTTTTGCTGGCCTTTTGCTCACATGTTC
TTTCCTGCGTTATCCCCTGATTCTGTGGATAACCGTATTACCGCCTTTGAGTGAGC
TGATACCGCTCGCCGCAGCCGAACGACCGAGCGCAGCGAGTCAGTGAGCGAGGA
AGCGGAAGAGCGCCCAATACGCAAACCGCCTCTCCCCGCGCGTTGGCCGATTCA
TTAATGCAGCTGGCACGACAGGTTTCCCGACTGGAAAGCGGGCAGTGAGCGCAA
CGCAATTAATGTGAGTTAGCTCACTCATTAGGCACCCCAGGCTTTACACTTTATG
CTTCCGGCTCGTATGTTGTGTGGAATTGTGAGCGGATAACAATTTCACACAGGAA
ACAGCTATGACCATGATTACGCC

Figure 7 (continued)

3. Feature of the nucleotide sequence:

| Name | Start | End | Description |
|---|---|---|---|
| 5LTR | 399 | 999 | |
| SP | 2278 | 2334 | Signal peptide |
| VK4 | 2335 | 2658 | Light chain of scFv |
| L | 2659 | 2703 | Linker between light chain and heavy chain |
| VH1 | 2704 | 3054 | Heavy chain of scFv |
| hinge | 3061 | 3195 | CD8a hinge |
| TM-CD8a | 3196 | 3267 | CD8a transmembrane domain |
| CD28 | 3268 | 3390 | CD28 endodmain |
| z | 3391 | 3729 | CD3 zeta chain |
| 3LTR | 3894 | 4460 | |

4. Amino acid sequence of CD28 version CAR:

MEFGLSWLFLVAILKGVQCDIVMTQSHKFMSTSIGARVSITCKASQDVRTAVA
WYQQKPGQSPKLLIYSASYRYTGVPDRFTGSGSGTDFTFTISSVQAEDLAVYYC
QQHYGTPPWTFGGGTKLEIKGGGGSGGGGSGGGGSEVQLVESGGGLVKPGGS
LKLSCEASRFTFSSYAMSWVRQTPEKRLEWVAAISGGGRYTYYPDSMKGRFTIS
RDNAKNFLYLQMSSLRSEDTAMYYCARHYDGYLDYWGQGTTLTVSSTRTTTPA
PRPPTPAPTIASQPLSLRPEACRPAAGGAVHTRGLDFACDIYIWAPLAGTCGVLL
LSLVITLYCRSKRSRLLHSDYMNMTPRRPGPTRKHYQPYAPPRDFAAYRSRVKF
SRSADAPAYQQGQNQLYNELNLGRREEYDVLDKRRGRDPEMGGKPRRKNPQE
GLYNELQKDKMAEAYSEIGMKGERRRGKGHDGLYQGLSTATKDTYDALHMQ
ALPPR

5. Feature of the amino acid sequence:

| Start | End | Description |
|---|---|---|
| 1 | 19 | Single peptide |
| 20 | 127 | Light chain of scFv (SEQ ID NO:6) |
| 128 | 142 | Linker between light chain and heavy chain |
| 143 | 259 | Heavy chain of scFv (SEQ ID NO:7) |
| 260 | 306 | Hinge from CD8a |
| 307 | 330 | Transmembrane domain from CD8a |
| 331 | 371 | Intracellular part of CD28 |
| 372 | 480 | CD3 zeta chain |

Figure 7 (continued)

1. Map of the plasmid

2. DNA sequence of the whole plasmid.

AAGCTTTGCTCTTAGGAGTTTCCTAATACATCCCAAACTCAAATATATAAAGCAT
TTGACTTGTTCTATGCCCTAGGGGGCGGGGGGAAGCTAAGCCAGCTTTTTTAAC
ATTTAAAATGTTAATTCCATTTTAAATGCACAGATGTTTTATTTCATAAGGGTTT
CAATGTGCATGAATGCTGCAATATTCCTGTTACCAAAGCTAGTATAAATAAAAAT
AGATAAACGTGGAAATTACTTAGAGTTTCTGTCATTAACGTTTCCTTCCTCAGTTG
ACAACATAAATGCGCTGCTGAGCAAGCCAGTTTGCATCTGTCAGGATCAATTTCC
CATTATGCCAGTCATATTAATTACTAGTCAATTAGTTGATTTTATTTTTGACATA
TACATGTGAATGAAAGACCCCACCTGTAGGTTTGGCAAGCTAGCTTAAGTAACGC
CATTTTGCAAGGCATGGAAAAATACATAACTGAGAATAGAAAAGTTCAGATCAA
GGTCAGGAACAGATGGAACAGCTGAATATGGGCCAAACAGGATATCTGTGGTAA
GCAGTTCCTGCCCCGGCTCAGGGCCAAGAACAGATGGAACAGCTGAATATGGGC
CAAACAGGATATCTGTGGTAAGCAGTTCCTGCCCCGGCTCAGGGCCAAGAACAG
ATGGTCCCCAGATGCGGTCCAGCCCTCAGCAGTTTCTAGAGAACCATCAGATGTT
TCCAGGGTGCCCCAAGGACCTGAAATGACCCTGTGCCTTATTTGAACTAACCAAT
CAGTTCGCTTCTCGCTTCTGTTCGCGCGCTTATGCTCCCGAGCTCAATAAAAGA
GCCCACAACCCCTCACTCGGGGCGCCAGTCCTCCGATTGACTGAGTCGCCCGGGT
ACCCGTGTATCCAATAAACCCTCTTGCAGTTGCATCCGACTTGTGGTCTCGCTGTT
CCTTGGGAGGGTCTCCTCTGAGTGATTGACTACCCGTCAGCGGGGGTCTTTCATT
TGGGGGCTCGTCCGGGATCGGGAGACCCCTGCCCAGGGACCACCGACCCACCAC
CGGGAGGTAAGCTGGCCAGCAACTTATCTGTGTCTGTCCGATTGTCTAGTGTCTA
TGACTGATTTTATGCGCCTGCGTCGGTACTAGTTAGCTAACTAGCTCTGTATCTGG
CGGACCCGTGGTGGAACTGACGAGTTCGGAACACCCGGCCGCAACCCTGGGAGA
CGTCCCAGGGACTTCGGGGGCCGTTTTGTGGCCCGACCTGAGTCCTAAAATCCC
GATCGTTTAGGACTCTTTGGTGCACCCCCCTTAGAGGAGGGATATGTGGTTCTGG
TAGGAGACGAGAACCTAAAACAGTTCCCGCCTCCGTCTGAATTTTGCTTTCGGT
TTGGGACCGAAGCCGCGCCGCGTCTTGTCTGCTGCAGCATCGTTCTGTGTTGT
CTCTGTCTGACTGTGTTTCTGTATTTGTCTGAAAATATGGGCCCGGGCTAGCCTGT
TACCACTCCCTTAAGTTTGACCTTAGGTCACTGGAAAGATGTCGAGCGGATCGCT
CACAACCAGTCGGTAGATGTCAAGAAGAGACGTTGGGTTACCTTCTGCTCTGCAG
AATGGCCAACCTTTAACGTCGGATGGCCGCGAGACGGCACCTTTAACCGAGACC
TCATCACCCAGGTTAAGATCAAGGTCTTTTCACCTGGCCCGCATGGACACCCAGA
CCAGGTGGGGTACATCGTGACCTGGGAAGCCTTGGCTTTTGACCCCCCTCCCTGG
GTCAAGCCCTTTGTACACCCTAAGCCTCCGCCTCCTCTTCCTCCATCCGCCCCGTC
TCTCCCCCTTGAACCTCCTCGTTCGACCCCGCCTCGATCCTCCCTTTATCCAGCCC
TCACTCCTTCTCTAGGCGCCCCCATATGGCCATATGAGATCTTATATGGGGCACC
CCCGCCCCTTGTAAACTTCCCTGACCCTGACATGACAAGAGTTACTAACAGCCCC
TCTCTCCAAGCTCACTTACAGGCTCTCTACTTAGTCCAGCACGAAGTCTGGAGAC
CTCTGGCGGCAGCCTACCAAGAACAACTGGACCGACCGGTGGTACCTCACCCTT
ACCGAGTCGGCGACACAGTGTGGGTCCGCCGACACCAGACTAAGAACCTAGAAC
CTCGCTGGAAAGGACCTTACACAGTCCTGCTGACCACCCCCACCGCCCTCAAAGT
AGACGGCATCGCAGCTTGGATACACGCCGCCCACGTGAAGGCTGCCGACCCCGG
GGGTGGACCATCCTCTAGACTGCCATGGAATTCGGCCTGAGCTGGCTGTTCCTGG
TGGCCATCCTGAAGGGCGTGCAGTGCGACATTGTGATGACCCAGTCTCACAAATT
CATGTCCACATCAATTGGAGCCAGGGTCAGCATCACCTGCAAGGCCAGTCAGGA
TGTGAGAACTGCTGTAGCCTGGTATCAACAGAAACCAGGCCAGTCTCCTAAACTA
CTAATTTACTCGGCATCCTACCGGTACACTGGAGTCCCTGATCGCTTCACTGGCA
GTGGATCTGGGACGGATTTCACTTTCACCATCAGCAGTGTGCAGGCTGAAGACCT
GGCAGTTTATTACTGTCAGCAACATTATGGTACTCCTCCGTGGACGTTCGGTGGA
GGCACCAAGCTGGAAATCAAGGCGGCGGAGGATCTGGCGGAGGCGGAAGTGG

Figure 8 (continued)

```
CGGAGGGGGCTCTGAAGTGCAGCTGGTGGAGTCTGGGGGAGGCTTAGTGAAGCC
TGGAGGGTCCCTGAAACTCTCCTGTGAAGCCTCTAGATTCACTTTCAGTAGCTAT
GCCATGTCTTGGGTTCGCCAGACTCCGGAGAAGAGGCTGGAGTGGGTCGCAGCC
ATTAGTGGAGGTGGTAGGTACACCTACTATCCAGACAGTATGAAGGGTCGATTC
ACCATCTCCAGAGACAATGCCAAGAATTTCCTGTACCTGCAAATGAGCAGTCTGA
GGTCTGAGGACACGGCCATGTATTACTGTGCAAGACACTATGATGGTTATCTTGA
CTACTGGGGCCAAGGCACCACTCTCACAGTCTCCTCAACGCGTACCACGACGCCA
GCGCCGCGACCACCAACACCGGCGCCCACCATCGCGTCGCAGCCCCTGTCCCTGC
GCCCAGAGGCGTGCCGGCCAGCGGCGGGGGCGCAGTGCACACGAGGGGCTG
GACTTCGCCTGTGATATCTACATCTGGGCGCCCTTGGCCGGGACTTGTGGGGTCC
TTCTCCTGTCACTGGTTATCACCCTTTACTGCAAACGGGGCAGAAAGAAACTCCT
GTATATATTCAAACAACCATTTATGAGACCAGTACAAACTACTCAAGAGGAAGA
TGGCTGTAGCTGCCGATTTCCAGAAGAAGAAGAAGGAGGATGTGAACTGAGAGT
GAAGTTCAGCAGGAGCGCAGACGCCCCGCGTACCAGCAGGGCCAGAACCAGCT
CTATAACGAGCTCAATCTAGGACGAAGAGAGGAGTACGATGTTTTGGACAAGAG
ACGTGGCCGGGACCCTGAGATGGGGGGAAAGCCGAGAAGGAAGAACCCTCAGG
AAGGCCTGTACAATGAACTGCAGAAAGATAAGATGGCGGAGGCCTACAGTGAGA
TTGGGATGAAAGGCGAGCGCCGGAGGGGCAAGGGGCACGATGGCCTTTACCAGG
GTCTCAGTACAGCCACCAAGGACACCTACGACGCCCTTCACATGCAGGCCCTGCC
CCCTCGCTAAGCATGCACCTCGAGATCGATCCGGATTAGTCCAATTTGTTAAAGA
CAGGATATCAGTGGTCCAGGCTCTAGTTTTGACTCAACAATATCACCAGCTGAAG
CCTATAGAGTACGAGCCATAGATAAAATAAAAGATTTTATTTAGTCTCCAGAAAA
AGGGGGGAATGAAAGACCCCACCTGTAGGTTTGGCAAGCTAGCTTAAGTAACGC
CATTTTGCAAGGCATGGAAAAATACATAACTGAGAATAGAGAAGTTCAGATCAA
GGTCAGGAACAGATGGAACAGCTGAATATGGGCCAAACAGGATATCTGTGGTAA
GCAGTTCCTGCCCCGGCTCAGGGCCAAGAACAGATGGAACAGCTGAATATGGGC
CAAACAGGATATCTGTGGTAAGCAGTTCCTGCCCCGGCTCAGGGCCAAGAACAG
ATGGTCCCCAGATGCGGTCCAGCCCTCAGCAGTTCTAGAGAACCATCAGATGTT
TCCAGGGTGCCCCAAGGACCTGAAATGACCCTGTGCCTTATTTGAACTAACCAAT
CAGTTCGCTTCTCGCTTCTGTTCGCGCGCTTCTGCTCCCCGAGCTCAATAAAAGAG
CCCACAACCCCTCACTCGGGGCGCCAGTCCTCCGATTGACTGAGTCGCCCGGGTA
CCCGTGTATCCAATAAACCCTCTTGCAGTTGCATCCGACTTGTGGTCTCGCTGTTC
CTTGGGAGGGTCTCCTCTGAGTGATTGACTACCCGTCAGCGGGGGTCTTTCACAC
ATGCAGCATGTATCAAAATTAATTTGGTTTTTTTTCTTAAGTATTTACATTAAATG
GCCATAGTACTTAAAGTTACATTGGCTTCCTTGAAATAAACATGGAGTATTCAGA
ATGTGTCATAAATATTTCTAATTTAAGATAGTATCTCCATTGGCTTTCTACTTTTT
CTTTTATTTTTTTTGTCCTCTGTCTTCCATTTGTTGTTGTTGTTGTTTGTTTGTTTG
TTTGTTGGTTGGTTGGTTAATTTTTTTTAAAGATCCTACACTATAGTTCAAGCTA
GACTATTAGCTACTCTGTAACCCAGGGTGACCTTGAAGTCATGGGTAGCCTGCTG
TTTTAGCCTTCCCACATCTAAGATTACAGGTATGAGCTATCATTTTGGTATATTG
ATTGATTGATTGATGTGTGTGTGTGTGATTGTGTTTGTGTGTGTGACTGTGA
AAATGTGTGTATGGGTGTGTGTGAATGTGTGTATGTATGTGTGTGTGAGTGTG
TGTGTGTGTGTGCATGTGTGTGTGTGACTGTGTCTATGTGTATGACTGTGTG
TGTGTGTGTGTGTGTGTGTGTGTGTGTGTGTGTGTGTTGTGAAAAAATATTC
TATGGTAGTGAGAGCCAACGCTCCGGCTCAGGTGTCAGGTTGGTTTTGAGACAG
AGTCTTTCACTTAGCTTGGAATTCACTGGCCGTCGTTTTACAACGTCGTGACTGGG
AAAACCCTGGCGTTACCCAACTTAATCGCCTTGCAGCACATCCCCCTTTCGCCAG
CTGGCGTAATAGCGAAGAGGCCCGCACCGATCGCCCTTCCCAACAGTTGCGCAG
CCTGAATGGCGAATGGCGCCTGATGCGGTATTTTCTCCTTACGCATCTGTGCGGT
ATTTCACACCGCATATGGTGCACTCTCAGTACAATCTGCTCTGATGCCGCATAGT
```

Figure 8 (continued)

```
TAAGCCAGCCCCGACACCCGCCAACACCCGCTGACGCGCCCTGACGGGCTTGTCT
GCTCCCGGCATCCGCTTACAGACAAGCTGTGACCGTCTCCGGGAGCTGCATGTGT
CAGAGGTTTTCACCGTCATCACCGAAACGCGCGATGACGAAAGGGCCTCGTGAT
ACGCCTATTTTTATAGGTTAATGTCATGATAATAATGGTTTCTTAGACGTCAGGTG
GCACTTTTCGGGGAAATGTGCGCGGAACCCCTATTTGTTTATTTTTCTAAATACAT
TCAAATATGTATCCGCTCATGAGACAATAACCCTGATAAATGCTTCAATAATATT
GAAAAAGGAAGAGTATGAGTATTCAACATTTCCGTGTCGCCCTTATTCCCTTTTT
GCGGCATTTTGCCTTCCTGTTTTGCTCACCCAGAAACGCTGGTGAAAGTAAAAG
ATGCTGAAGATCAGTTGGGTGCACGAGTGGGTTACATCGAACTGGATCTCAACA
GCGGTAAGATCCTTGAGAGTTTTCGCCCCGAAGAACGTTTTCCAATGATGAGCAC
TTTTAAAGTTCTGCTATGTGGCGCGGTATTATCCCGTATTGACGCCGGGCAAGAG
CAACTCGGTCGCCGCATACACTATTCTCAGAATGACTTGGTTGAGTACTCACCAG
TCACAGAAAAGCATCTTACGGATGGCATGACAGTAAGAGAATTATGCAGTGCTG
CCATAACCATGAGTGATAACACTGCGGCCAACTTACTTCTGACAACGATCGGAG
GACCGAAGGAGCTAACCGCTTTTTTGCACAACATGGGGGATCATGTAACTCGCCT
TGATCGTTGGGAACCGGAGCTGAATGAAGCCATACCAAACGACGAGCGTGACAC
CACGATGCCTGTAGCAATGGCAACAACGTTGCGCAAACTATTAACTGGCGAACT
ACTTACTCTAGCTTCCCGGCAACAATTAATAGACTGGATGGAGGCGGATAAAGTT
GCAGGACCACTTCTGCGCTCGGCCCTTCCGGCTGGCTGGTTTATTGCTGATAAAT
CTGGAGCCGGTGAGCGTGGGTCTCGCGGTATCATTGCAGCACTGGGGCCAGATG
GTAAGCCCTCCCGTATCGTAGTTATCTACACGACGGGGAGTCAGGCAACTATGGA
TGAACGAAATAGACAGATCGCTGAGATAGGTGCCTCACTGATTAAGCATTGGTA
ACTGTCAGACCAAGTTTACTCATATATACTTTAGATTGATTTAAAACTTCATTTTT
AATTTAAAAGGATCTAGGTGAAGATCCTTTTTGATAATCTCATGACCAAAATCCC
TTAACGTGAGTTTTCGTTCCACTGAGCGTCAGACCCCGTAGAAAAGATCAAAGGA
TCTTCTTGAGATCCTTTTTTTCTGCGCGTAATCTGCTGCTTGCAAACAAAAAAACC
ACCGCTACCAGCGGTGGTTTGTTTGCCGGATCAAGAGCTACCAACTCTTTTTCCG
AAGGTAACTGGCTTCAGCAGAGCGCAGATACCAAATACTGTCCTTCTAGTGTAGC
CGTAGTTAGGCCACCACTTCAAGAACTCTGTAGCACCGCCTACATACCTCGCTCT
GCTAATCCTGTTACCAGTGGCTGCTGCCAGTGGCGATAAGTCGTGTCTTACCGGG
TTGGACTCAAGACGATAGTTACCGGATAAGGCGCAGCGGTCGGGCTGAACGGGG
GGTTCGTGCACACAGCCCAGCTTGGAGCGAACGACCTACACCGAACTGAGATAC
CTACAGCGTGAGCATTGAGAAAGCGCCACGCTTCCCGAAGGGAGAAAGGCGGAC
AGGTATCCGGTAAGCGGCAGGGTCGGAACAGGAGAGCGCACGAGGGAGCTTCC
AGGGGGAAACGCCTGGTATCTTTATAGTCCTGTCGGGTTTCGCCACCTCTGACTT
GAGCGTCGATTTTGTGATGCTCGTCAGGGGGGCGGAGCCTATGGAAAAACGCC
AGCAACGCGGCCTTTTTACGGTTCCTGGCCTTTTGCTGGCCTTTTGCTCACATGTT
CTTTCCTGCGTTATCCCTGATTCTGTGGATAACCGTATTACCGCCTTTGAGTGAG
CTGATACCGCTCGCCGCAGCCGAACGACCGAGCGCAGCGAGTCAGTGAGCGAGG
AAGCGGAAGAGCGCCCAATACGCAAACCGCCTCTCCCCGCGCGTTGGCCGATTC
ATTAATGCAGCTGGCACGACAGGTTTCCCGACTGGAAAGCGGGCAGTGAGCGCA
ACGCAATTAATGTGAGTTAGCTCACTCATTAGGCACCCCAGGCTTTACACTTTAT
GCTTCCGGCTCGTATGTTGTGTGGAATTGTGAGCGGATAACAATTTCACACAGGA
AACAGCTATGACCATGATTACGCC
```

Figure 8 (continued)

3. Feature of the nucleotide sequence:

| Name | Start | End | Description |
|---|---|---|---|
| 5LTR | 399 | 999 | |
| SP | 2278 | 2334 | Signal peptide |
| VK4 | 2335 | 2658 | Light chain of scFv |
| L | 2659 | 2703 | Linker between light chain and heavy chain |
| VH1 | 2704 | 3054 | Heavy chain of scFv |
| H | 3061 | 3195 | CD8a hinge |
| TM-CD8a | 3196 | 3267 | CD8a transmembrane domain |
| 4-1BB | 3268 | 3393 | 4-1BB intracytoplasmic domain |
| z | 3394 | 3732 | CD3zeta chain |
| 3LTR | 3897 | 4463 | |

4. Amino acid sequence of 4-1-BB version CAR:

MEFGLSWLFLVAILKGVQCDIVMTQSHKFMSTSIGARVSITCKASQDVRTAVA
WYQQKPGQSPKLLIYSASYRYTGVPDRFTGSGSGTDFTFTISSVQAEDLAVYYC
QQHYGTPPWTFGGGTKLEIKGGGGSGGGGSGGGGSEVQLVESGGGLVKPGGS
LKLSCEASRFTFSSYAMSWVRQTPEKRLEWVAAISGGGRYTYYPDSMKGRFTIS
RDNAKNFLYLQMSSLRSEDTAMYYCARHYDGYLDYWGQGTTLTVSSTRTTTPA
PRPPTPAPTIASQPLSLRPEACRPAAGGAVHTRGLDFACDIYIWAPLAGTCGVLL
LSLVITLYCKRGRKKLLYIFKQPFMRPVQTTQEEDGCSCRFPEEEEGGCELRVK
FSRSADAPAYQQGQNQLYNELNLGRREEYDVLDKRRGRDPEMGGKPRRKNPQ
EGLYNELQKDKMAEAYSEIGMKGERRRGKGHDGLYQGLSTATKDTYDALHM
QALPPR

5. Feature of the amino acid sequence:

| Start | End | Description |
|---|---|---|
| 1 | 19 | Single peptide |
| 20 | 127 | Light chain of scFv (SEQ ID NO:6) |
| 128 | 142 | Linker between light chain and heavy chain |
| 143 | 259 | Heavy chain of scFv (SEQ ID NO:7) |
| 260 | 306 | Hinge from CD8a |
| 307 | 330 | Transmembrane domain from CD8a |
| 331 | 372 | Intracellular part of CD28 |
| 373 | 480 | CD3 zeta chain |

Figure 8 (continued)

SEQUENCE LISTING

<160> NUMBER OF SEQ ID NOS: 7

<210> SEQ ID NO 1
<211> LENGTH: 483
<212> TYPE: PRT
<213> ORGANISM: Artificial
<220> FEATURE:
<223> OTHER INFORMATION: chimeric antigen receptor CD28

<400> SEQUENCE: 1

Met Glu Phe Gly Leu Ser Trp Leu Phe Leu Val Ala Ile Leu Lys Gly
1               5                   10                  15

Val Gln Cys Asp Ile Val Met Thr Gln Ser His Lys Phe Met Ser Thr
                20                  25                  30

Ser Ile Gly Ala Arg Val Ser Ile Thr Cys Lys Ala Ser Gln Asp Val
            35                  40                  45

Arg Thr Ala Val Ala Trp Tyr Gln Gln Lys Pro Gly Gln Ser Pro Lys
        50                  55                  60

Leu Leu Ile Tyr Ser Ala Ser Tyr Arg Tyr Thr Gly Val Pro Asp Arg
65                  70                  75                  80

Phe Thr Gly Ser Gly Ser Gly Thr Asp Phe Thr Phe Thr Ile Ser Ser
                85                  90                  95

Val Gln Ala Glu Asp Leu Ala Val Tyr Tyr Cys Gln Gln His Tyr Gly
            100                 105                 110

Thr Pro Pro Trp Thr Phe Gly Gly Thr Lys Leu Glu Ile Lys Gly
        115                 120                 125

Gly Gly Gly Ser Gly Gly Gly Gly Ser Gly Gly Gly Gly Ser Glu Val
    130                 135                 140

Gln Leu Val Glu Ser Gly Gly Gly Leu Val Lys Pro Gly Gly Ser Leu
145                 150                 155                 160

Lys Leu Ser Cys Glu Ala Ser Arg Phe Thr Phe Ser Ser Tyr Ala Met
                165                 170                 175

Ser Trp Val Arg Gln Thr Pro Glu Lys Arg Leu Glu Trp Val Ala Ala
            180                 185                 190

Ile Ser Gly Gly Gly Arg Tyr Thr Tyr Tyr Pro Asp Ser Met Lys Gly
        195                 200                 205

Arg Phe Thr Ile Ser Arg Asp Asn Ala Lys Asn Phe Leu Tyr Leu Gln
    210                 215                 220

Met Ser Ser Leu Arg Ser Glu Asp Thr Ala Met Tyr Tyr Cys Ala Arg
225                 230                 235                 240

His Tyr Asp Gly Tyr Leu Asp Tyr Trp Gly Gln Gly Thr Thr Leu Thr
                245                 250                 255

Val Ser Ser Thr Arg Thr Thr Thr Pro Ala Pro Arg Pro Pro Thr Pro
            260                 265                 270

Ala Pro Thr Ile Ala Ser Gln Pro Leu Ser Leu Arg Pro Glu Ala Cys
            275                 280                 285

Arg Pro Ala Ala Gly Gly Ala Val His Thr Arg Gly Leu Asp Phe Ala
        290                 295                 300

Cys Asp Ile Tyr Ile Trp Ala Pro Leu Ala Gly Thr Cys Gly Val Leu
305                 310                 315                 320

Leu Leu Ser Leu Val Ile Thr Leu Tyr Cys Arg Ser Lys Arg Ser Arg
                325                 330                 335

Leu Leu His Ser Asp Tyr Met Asn Met Thr Pro Arg Arg Pro Gly Pro
            340                 345                 350

Thr Arg Lys His Tyr Gln Pro Tyr Ala Pro Pro Arg Asp Phe Ala Ala
            355                 360                 365

Tyr Arg Ser Arg Val Lys Phe Ser Arg Ser Ala Asp Ala Pro Ala Tyr
        370                 375                 380

Gln Gln Gly Gln Asn Gln Leu Tyr Asn Glu Leu Asn Leu Gly Arg Arg
385                 390                 395                 400

Glu Glu Tyr Asp Val Leu Asp Lys Arg Gly Arg Asp Pro Glu Met
                405                 410                 415

Gly Gly Lys Pro Arg Arg Lys Asn Pro Gln Glu Gly Leu Tyr Asn Glu
                420                 425                 430

Leu Gln Lys Asp Lys Met Ala Glu Ala Tyr Ser Glu Ile Gly Met Lys
            435                 440                 445

Gly Glu Arg Arg Arg Gly Lys Gly His Asp Gly Leu Tyr Gln Gly Leu
        450                 455                 460

Ser Thr Ala Thr Lys Asp Thr Tyr Asp Ala Leu His Met Gln Ala Leu
465                 470                 475                 480

Pro Pro Arg

<210> SEQ ID NO 2
<211> LENGTH: 484
<212> TYPE: PRT
<213> ORGANISM: Artificial
<220> FEATURE:
<223> OTHER INFORMATION: chimeric antigen receptor 4-1-BB

<400> SEQUENCE: 2

Met Glu Phe Gly Leu Ser Trp Leu Phe Leu Val Ala Ile Leu Lys Gly
1               5                   10                  15

Val Gln Cys Asp Ile Val Met Thr Gln Ser His Lys Phe Met Ser Thr
            20                  25                  30

Ser Ile Gly Ala Arg Val Ser Ile Thr Cys Lys Ala Ser Gln Asp Val
        35                  40                  45

Arg Thr Ala Val Ala Trp Tyr Gln Gln Lys Pro Gly Gln Ser Pro Lys
    50                  55                  60

Leu Leu Ile Tyr Ser Ala Ser Tyr Arg Tyr Thr Gly Val Pro Asp Arg
65                  70                  75                  80

Phe Thr Gly Ser Gly Ser Gly Thr Asp Phe Thr Phe Thr Ile Ser Ser
                85                  90                  95

Val Gln Ala Glu Asp Leu Ala Val Tyr Tyr Cys Gln Gln His Tyr Gly
            100                 105                 110

```
Thr Pro Pro Trp Thr Phe Gly Gly Thr Lys Leu Glu Ile Lys Gly
            115                 120                 125
Gly Gly Gly Ser Gly Gly Gly Ser Gly Gly Gly Ser Glu Val
    130                 135                 140
Gln Leu Val Glu Ser Gly Gly Leu Val Lys Pro Gly Gly Ser Leu
145                 150                 155                 160
Lys Leu Ser Cys Glu Ala Ser Arg Phe Thr Phe Ser Ser Tyr Ala Met
                165                 170                 175
Ser Trp Val Arg Gln Thr Pro Glu Lys Arg Leu Glu Trp Val Ala Ala
            180                 185                 190
Ile Ser Gly Gly Gly Arg Tyr Thr Tyr Tyr Pro Asp Ser Met Lys Gly
        195                 200                 205
Arg Phe Thr Ile Ser Arg Asp Asn Ala Lys Asn Phe Leu Tyr Leu Gln
    210                 215                 220
Met Ser Ser Leu Arg Ser Glu Asp Thr Ala Met Tyr Tyr Cys Ala Arg
225                 230                 235                 240
His Tyr Asp Gly Tyr Leu Asp Tyr Trp Gly Gln Gly Thr Thr Leu Thr
                245                 250                 255
Val Ser Ser Thr Arg Thr Thr Thr Pro Ala Pro Arg Pro Pro Thr Pro
            260                 265                 270
Ala Pro Thr Ile Ala Ser Gln Pro Leu Ser Leu Arg Pro Glu Ala Cys
        275                 280                 285
Arg Pro Ala Ala Gly Gly Ala Val His Thr Arg Gly Leu Asp Phe Ala
    290                 295                 300
Cys Asp Ile Tyr Ile Trp Ala Pro Leu Ala Gly Thr Cys Gly Val Leu
305                 310                 315                 320
Leu Leu Ser Leu Val Ile Thr Leu Tyr Cys Lys Arg Gly Arg Lys Lys
                325                 330                 335
Leu Leu Tyr Ile Phe Lys Gln Pro Phe Met Arg Pro Val Gln Thr Thr
            340                 345                 350
Gln Glu Glu Asp Gly Cys Ser Cys Arg Phe Pro Glu Glu Glu Gly
        355                 360                 365
Gly Cys Glu Leu Arg Val Lys Phe Ser Arg Ser Ala Asp Ala Pro Ala
    370                 375                 380
Tyr Gln Gln Gly Gln Asn Gln Leu Tyr Asn Glu Leu Asn Leu Gly Arg
385                 390                 395                 400
Arg Glu Glu Tyr Asp Val Leu Asp Lys Arg Arg Gly Arg Asp Pro Glu
                405                 410                 415
Met Gly Gly Lys Pro Arg Arg Lys Asn Pro Gln Glu Gly Leu Tyr Asn
            420                 425                 430
Glu Leu Gln Lys Asp Lys Met Ala Glu Ala Tyr Ser Glu Ile Gly Met
        435                 440                 445
Lys Gly Glu Arg Arg Arg Gly Lys Gly His Asp Gly Leu Tyr Gln Gly
    450                 455                 460
Leu Ser Thr Ala Thr Lys Asp Thr Tyr Asp Ala Leu His Met Gln Ala
465                 470                 475                 480
Leu Pro Pro Arg

<210> SEQ ID NO 3
<211> LENGTH: 7811
<212> TYPE: DNA
<213> ORGANISM: Artificial
<220> FEATURE:
<223> OTHER INFORMATION: plasmid CD28
```

<400> SEQUENCE: 3

```
aagctttgct cttaggagtt tcctaataca tcccaaactc aaatatataa agcatttgac      60
ttgttctatg ccctagggggg cggggggaag ctaagccagc ttttttttaac atttaaaatg    120
ttaattccat tttaaatgca cagatgtttt tatttcataa gggtttcaat gtgcatgaat     180
gctgcaatat tcctgttacc aaagctagta taaataaaaa tagataaacg tggaaattac     240
ttagagtttc tgtcattaac gtttccttcc tcagttgaca acataaatgc gctgctgagc     300
aagccagttt gcatctgtca ggatcaattt cccattatgc cagtcatatt aattactagt    360
caattagttg attttttattt ttgacatata catgtgaatg aaagacccca cctgtaggtt    420
tggcaagcta gcttaagtaa cgccattttg caaggcatgg aaaaatacat aactgagaat    480
agaaaagttc agatcaaggt caggaacaga tggaacagct gaatatgggc caaacaggat     540
atctgtggta agcagttcct gccccggctc agggccaaga acagatggaa cagctgaata    600
tgggccaaac aggatatctg tggtaagcag ttcctgcccc ggctcagggc caagaacaga    660
tggtccccag atgcggtcca gccctcagca gtttctagaa accatcaga tgtttccagg     720
gtgcccaag gacctgaaat gaccctgtgc cttatttgaa ctaaccaatc agttcgcttc      780
tcgcttctgt tcgcgcgctt atgctccccg agctcaataa aagagcccac aacccctcac    840
tcggggcgcc agtcctccga ttgactgagt cgcccgggta cccgtgtatc aataaaccc     900
tcttgcagtt gcatccgact gtggtctcg ctgttccttg ggagggtctc ctctgagtga     960
ttgactaccc gtcagcgggg gtcttttcatt tgggggctcg tccgggatcg ggagacccct    1020
gcccagggac caccgaccca ccaccgggag gtaagctggc cagcaactta tctgtgtctg    1080
tccgattgtc tagtgtctat gactgatttt atgcgcctgc gtcggtacta gttagctaac    1140
tagctctgta tctggcggac ccgtggtgga actgacgagt tcggaacacc cggccgcaac    1200
cctgggagac gtcccaggga cttcgggggc cgttttttgtg gcccgacctg agtcctaaaa    1260
tcccgatcgt ttaggactct ttggtgcacc ccccttagag gagggatatg tggttctggt    1320
aggagacgag aacctaaaac agttcccgcc tccgtctgaa ttttttgcttt cggtttggga    1380
ccgaagccgc gccgcgcgtc ttgtctgctg cagcatcgtt ctgtgttgtc tctgtctgac    1440
tgtgtttctg tatttgtctg aaaatatggg cccgggctag cctgttacca ctcccttaag    1500
tttgaccttta ggtcactgga aagatgtcga gcggatcgct cacaaccagt cggtagatgt    1560
caagaagaga cgttgggtta ccttctgctc tgcagaatgg ccaaccttta acgtcggatg    1620
gccgcgagac ggcacctttta accgagacct catcacccag gttaagatca aggtcttttc    1680
acctggcccg catggacacc cagaccaggt ggggtacatc gtgacctggg aagccttggc    1740
ttttgaccccc cctcccctggg tcaagccctt tgtacaccct aagcctccgc ctcctcttcc    1800
tccatccgcc ccgtctctcc cccttgaacc tcctcgttcg accccgcctc gatcctccct    1860
ttatccagcc ctcactcctt tctctaggcgc cccatatgg ccatatgaga tcttatatgg    1920
ggcaccccg cccttgtaa acttccctga ccctgacatg acaagagtta ctaacagccc    1980
ctctctccaa gctcacttac aggctctcta cttagtccag cacgaagtct ggagacctct    2040
ggcggcagcc taccaagaac aactggaccg accgtggtta cctcacccct accgagtcgg    2100
cgacacagtg tgggtccgcc gacaccagac taagaaccta gaacctcgct ggaaaggacc    2160
ttacacagtc ctgctgacca ccccccaccgc cctcaaagta gacggcatcg cagcttggat    2220
acacgccgcc cacgtgaagg ctgccgaccc cgggggtgga ccatcctcta gactgccatg    2280
gaattcggcc tgagctggct gttcctggtg gccatcctga agggcgtgca gtgcgacatt    2340
```

```
gtgatgaccc agtctcacaa attcatgtcc acatcaattg gagccagggt cagcatcacc      2400
tgcaaggcca gtcaggatgt gagaactgct gtagcctggt atcaacagaa accaggccag      2460
tctcctaaac tactaattta ctcggcatcc taccggtaca ctggagtccc tgatcgcttc      2520
actggcagtg gatctgggac ggatttcact ttcaccatca gcagtgtgca ggctgaagac      2580
ctggcagttt attactgtca gcaacattat ggtactcctc cgtggacgtt cggtggaggc      2640
accaagctgg aaatcaaagg cggcggagga tctggcggag gcggaagtgg cggagggggc      2700
tctgaagtgc agctggtgga gtctggggga ggcttagtga agcctggagg gtccctgaaa      2760
ctctcctgtg aagcctctag attcactttc agtagctatg ccatgtcttg ggttcgccag      2820
actccggaga gaggctggag gtgggtcgca gccattagtg gaggtggtag gtacacctac      2880
tatccagaca gtatgaaggg tcgattcacc atctccagag acaatgccaa gaatttcctg      2940
tacctgcaaa tgagcagtct gaggtctgag gacacggcca tgtattactg tgcaagacac      3000
tatgatggtt atcttgacta ctggggccaa ggcaccactc tcacagtctc ctcaacgcgt      3060
accacgacgc cagcgccgcg accaccaaca ccggcgccca ccatcgcgtc gcagcccctg      3120
tccctgcgcc cagaggcgtg ccggccagcg cggggggcg cagtgcacac gagggggctg       3180
gacttcgcct gtgatatcta catctgggcg cccttggccg gacttgtgg ggtccttctc       3240 ctgtcactgg ttatcaccct ttactgcagg agtaagagga gcaggctcct gcacagtgac      3300
tacatgaaca tgactccccg ccgccccggg cccacccgca agcattacca gccctatgcc      3360
ccaccacgcg acttcgcagc ctatcgctcc agagtgaagt tcagcaggag cgcagacgcc      3420
cccgcgtacc agcagggcca gaaccagctc tataacgagc tcaatctagg acgaagagag      3480
gagtacgatg ttttggacaa gagacgtggc cgggaccctg agatgggggg aaagccgaga      3540
aggaagaacc ctcaggaagg cctgtacaat gaactgcaga agataagat ggcggaggcc       3600 tacagtgaga ttgggatgaa aggcgagcgc cggaggggca aggggcacga tggcctttac      3660
cagggtctca gtacagccac caaggacacc tacgacgccc ttcacatgca ggccctgccc      3720
cctcgctaag catgcaccct cgagatcgat cggattagtc caatttgtta aagacaggat      3780
atcagtggtc caggctctag ttttgactca acaatatcac cagctgaagc ctatagagta      3840
cgagccatag ataaaataaa agattttatt tagtctccag aaaaagggg gaatgaaaga       3900 ccccacctgt aggtttggca agctagctta agtaacgcca ttttgcaagg catggaaaaa      3960
tacataactg agaatagaga agttcagatc aaggtcagga acagatggaa cagctgaata      4020
tgggccaaac aggatatctg tggtaagcag ttcctgcccc ggctcagggc caagaacaga      4080
tggaacagct gaatatgggc caaacaggat atctgtggta agcagttcct gccccggctc      4140
agggccaaga acagatggtc ccagatgcg gtccagccct cagcagtttc tagagaacca       4200
tcagatgttt ccagggtgcc ccaaggacct gaaatgaccc tgtgccttat ttgaactaac      4260
caatcagttc gcttctcgct tctgttcgcg cgcttctgct ccccgagctc aataaaagag      4320
cccacaaccc ctcactcggg cgccagtcc tccgattgac tgagtcgccc gggtacccgt       4380
gtatccaata aaccctcttg cagttgcatc cgacttgtgg tctcgctgtt ccttgggagg      4440
gtctcctctg agtgattgac tacccgtcag cgggggtctt tcacacatgc agcatgtatc      4500
aaaattaatt tggttttttt tcttaagtat ttacattaaa tggccatagt acttaaagtt      4560
acattggctt ccttgaaata aacatggagt attcagaatg tgtcataaat atttctaatt      4620
ttaagatagt atctccattg gctttctact ttttctttta ttttttttg tcctctgtct       4680
```

```
tccatttgtt gttgttgttg tttgtttgtt tgtttgttgg ttggttggtt aattttttt     4740
taaagatcct acactatagt tcaagctaga ctattagcta ctctgtaacc cagggtgacc     4800
ttgaagtcat gggtagcctg ctgttttagc cttcccacat ctaagattac aggtatgagc    4860
tatcattttt ggtatattga ttgattgatt gattgatgtg tgtgtgtgtg attgtgtttg    4920
tgtgtgtgac tgtgaaaatg tgtgtatggg tgtgtgtgaa tgtgtgtatg tatgtgtgtg    4980
tgtgagtgtg tgtgtgtgtg tgtgcatgtg tgtgtgtgtg actgtgtcta tgtgtatgac    5040
tgtgtgtgtg tgtgtgtgtg tgtgtgtgtg tgtgtgtgtg tgtgtgttgt gaaaaaatat    5100
tctatggtag tgagagccaa cgctccggct caggtgtcag gttggttttt gagacagagt    5160
ctttcactta gcttggaatt cactggccgt cgttttacaa cgtcgtgact gggaaaaccc    5220
tggcgttacc caacttaatc gccttgcagc acatccccct ttcgccagct ggcgtaatag    5280
cgaagaggcc cgcaccgatc gcccttccca acagttgcgc agcctgaatg gcgaatggcg    5340
cctgatgcgg tattttctcc ttacgcatct gtgcggtatt tcacaccgca tatggtgcac    5400
tctcagtaca atctgctctg atgccgcata gttaagccag ccccgacacc cgccaacacc    5460
cgctgacgcg ccctgacggg cttgtctgct cccggcatcc gcttacagac aagctgtgac    5520
cgtctccggg agctgcatgt gtcagaggtt ttcaccgtca tcaccgaaac gcgcgatgac    5580
gaaagggcct cgtgatacgc ctatttttat aggttaatgt catgataata atggtttctt    5640
agacgtcagg tggcactttt cggggaaatg tgcgcggaac ccctatttgt ttatttttct    5700
aaatacattc aaatatgtat ccgctcatga caataaccc tgataaatg cttcaataat     5760
attgaaaaag gaagagtatg agtattcaac atttccgtgt cgcccttatt ccctttttg     5820
cggcattttg ccttcctgtt tttgctcacc cagaaacgct ggtgaaagta aaagatgctg    5880
aagatcagtt gggtgcacga gtgggttaca tcgaactgga tctcaacagc ggtaagatcc    5940
ttgagagttt tcgccccgaa gaacgttttc caatgatgag cacttttaaa gttctgctat    6000
gtggcgcggt attatcccgt attgacgccg ggcaagagca actcggtcgc cgcatacact    6060
attctcagaa tgacttggtt gagtactcac cagtcacaga aaagcatctt acggatggca    6120
tgacagtaag agaattatgc agtgctgcca taaccatgag tgataacact gcggccaact    6180
tacttctgac aacgatcgga ggaccgaagg agctaaccgc ttttttgcac aacatggggg    6240
atcatgtaac tcgccttgat cgttgggaac cggagctgaa tgaagccata ccaaacgacg    6300
agcgtgacac cacgatgcct gtagcaatgg caacaacgtt gcgcaaacta ttaactggcg    6360
aactacttac tctagcttcc cggcaacaat taatagactg gatggaggcg gataaagttg    6420
caggaccact tctgcgctcg gcccttccgg ctggctggtt tattgctgat aaatctggag    6480
ccggtgagcg tgggtctcgc ggtatcattg cagcactggg gccagatggt aagccctccc    6540
gtatcgtagt tatctacacg acggggagtc aggcaactat ggatgaacga aatagacaga    6600
tcgctgagat aggtgcctca ctgattaagc attggtaact gtcagaccaa gtttactcat    6660
atatacttta gattgattta aaacttcatt tttaatttaa aaggatctag gtgaagatcc    6720
tttttgataa tctcatgacc aaaatccctt aacgtgagtt ttcgttccac tgagcgtcag    6780
accccgtaga aaagatcaaa ggatcttctt gagatccttt ttttctgcgc gtaatctgct    6840
gcttgcaaac aaaaaaacca ccgctaccag cggtggtttg tttgccggat caagagctac    6900
caactctttt tccgaaggta actggcttca gcagagcgca gataccaaat actgtccttc    6960
tagtgtagcc gtagttaggc caccacttca agaactctgt agcaccgcct acatacctcg    7020
ctctgctaat cctgttacca gtggctgctg ccagtggcga taagtcgtgt cttaccgggt    7080
```

| | | |
|---|---|---|
| tggactcaag acgatagtta ccggataagg cgcagcggtc gggctgaacg gggggttcgt | 7140 |
| gcacacagcc cagcttggag cgaacgacct acaccgaact gagataccta cagcgtgagc | 7200 |
| attgagaaag cgccacgctt cccgaaggga gaaaggcgga caggtatccg gtaagcggca | 7260 |
| gggtcggaac aggagagcgc acgagggagc ttccaggggg aaacgcctgg tatctttata | 7320 |
| gtcctgtcgg gtttcgccac ctctgacttg agcgtcgatt tttgtgatgc tcgtcagggg | 7380 |
| ggcggagcct atggaaaaac gccagcaacg cggccttttt acggttcctg gccttttgct | 7440 |
| ggccttttgc tcacatgttc tttcctgcgt tatcccctga ttctgtggat aaccgtatta | 7500 |
| ccgcctttga gtgagctgat accgctcgcc gcagccgaac gaccgagcgc agcgagtcag | 7560 |
| tgagcgagga agcggaagag cgcccaatac gcaaaccgcc tctccccgcg cgttggccga | 7620 |
| ttcattaatg cagctggcac gacaggtttc ccgactggaa agcgggcagt gagcgcaacg | 7680 |
| caattaatgt gagttagctc actcattagg caccccaggc tttacacttt atgcttccgg | 7740 |
| ctcgtatgtt gtgtggaatt gtgagcggat aacaatttca cacaggaaac agctatgacc | 7800 |
| atgattacgc c | 7811 |

<210> SEQ ID NO 4
<211> LENGTH: 7814
<212> TYPE: DNA
<213> ORGANISM: Artificial
<220> FEATURE:
<223> OTHER INFORMATION: plasmid 4-1-BB

<400> SEQUENCE: 4

| | | |
|---|---|---|
| aagctttgct cttaggagtt tcctaataca tcccaaactc aaatatataa agcatttgac | 60 |
| ttgttctatg ccctaggggg cgggggggaag ctaagccagc ttttttttaac atttaaaatg | 120 |
| ttaattccat tttaaatgca cagatgtttt tatttcataa gggtttcaat gtgcatgaat | 180 |
| gctgcaatat tcctgttacc aaagctagta taaataaaaa tagataaacg tggaaattac | 240 |
| ttagagtttc tgtcattaac gtttccttcc tcagttgaca acataaatgc gctgctgagc | 300 |
| aagccagttt gcatctgtca ggatcaattt cccattatgc cagtcatatt aattactagt | 360 |
| caattagttg attttttattt ttgacatata catgtgaatg aaagaccccca cctgtaggtt | 420 |
| tggcaagcta gcttaagtaa cgccatttttg caaggcatgg aaaatacat aactgagaat | 480 |
| agaaaagttc agatcaaggt caggaacaga tggaacagct gaatatgggc caaacaggat | 540 |
| atctgtggta agcagttcct gccccggctc agggccaaga acagatggaa cagctgaata | 600 |
| tgggccaaac aggatatctg tggtaagcag ttcctgcccc ggctcagggc caagaacaga | 660 |
| tggtccccag atgcggtcca gccctcagca gtttctagag aaccatcaga tgtttccagg | 720 |
| gtgccccaag gacctgaaat gaccctgtgc cttatttgaa ctaaccaatc agttcgcttc | 780 |
| tcgcttctgt tcgcgcgctt atgctccccg agctcaataa aagagcccac aaccccctcac | 840 |
| tcggggcgcc agtcctccga ttgactgagt cgcccgggta cccgtgtatc caataaaccc | 900 |
| tcttgcagtt gcatccgact tgtggtctcg ctgttccttg ggagggtctc ctctgagtga | 960 |
| ttgactaccc gtcagcgggg gtctttcatt tgggggctcg tccggatcg ggagacccct | 1020 |
| gcccagggac caccgaccca ccaccgggag gtaagctggc cagcaactta tctgtgtctg | 1080 |
| tccgattgtc tagtgtctat gactgatttt atgcgcctgc gtcggtacta gttagctaac | 1140 |
| tagctctgta tctggcggac ccgtggtgga actgacgagt tcggaacacc cggccgcaac | 1200 |
| cctgggagac gtcccaggga cttcgggggc cgttttttgtg gcccgacctg agtcctaaaa | 1260 |

```
tcccgatcgt ttaggactct tggtgcacc ccccttagag gagggatatg tggttctggt    1320
aggagacgag aacctaaaac agttcccgcc tccgtctgaa tttttgcttt cggtttggga    1380
ccgaagccgc gccgcgcgtc ttgtctgctg cagcatcgtt ctgtgttgtc tctgtctgac    1440
tgtgtttctg tatttgtctg aaaatatggg cccgggctag cctgttacca ctcccttaag    1500
tttgaccttg ggtcactgga aagatgtcga gcggatcgct cacaaccagt cggtagatgt    1560
caagaagaga cgttgggtta ccttctgctc tgcagaatgg ccaaccttta acgtcggatg    1620
gccgcgagac ggcaccttta accgagacct catcacccag gttaagatca aggtcttttc    1680
acctggcccg catggacacc cagaccaggt ggggtacatc gtgacctggg aagccttggc    1740
ttttgacccc cctccctggg tcaagccctt tgtacaccct aagcctccgc ctcctcttcc    1800
tccatccgcc ccgtctctcc cccttgaacc tcctcgttcg accccgcctc gatcctccct    1860
ttatccagcc ctcactcctt tctaggcgc ccccatatgg ccatatgaga tcttatatgg    1920
ggcacccccg ccccttgtaa acttccctga ccctgacatg acaagagtta ctaacagccc    1980
ctctctccaa gctcacttac aggctctcta cttagtccag cacgaagtct ggagacctct    2040
ggcggcagcc taccaagaac aactggaccg accggtggta cctcacccctt accgagtcgg    2100 cgacacagtg tgggtccgcc gacaccagac taagaaccta gaacctcgct ggaaaggacc    2160
ttacacagtc ctgctgacca cccccaccgc cctcaaagta gacggcatcg cagcttggat    2220
acacgccgcc cacgtgaagg ctgccgaccc cgggggtgga ccatcctcta gactgccatg    2280
gaattcggcc tgagctggct gttcctggtg gccatcctga agggcgtgca gtgcgacatt    2340
gtgatgaccc agtctcacaa attcatgtcc acatcaattg gagccagggt cagcatcacc    2400
tgcaaggcca gtcaggatgt gagaactgct gtagcctggt atcaacagaa accaggccag    2460
tctcctaaac tactaatta tcggcatcc taccggtaca ctggagtccc tgatcgcttc    2520
actggcagtg gatctgggac ggatttcact ttcaccatca gcagtgtgca ggctgaagac    2580
ctggcagttt attactgtca gcaacattat ggtactcctc cgtggacgtt cggtggaggc    2640
accaagctgg aaatcaaagg cggcggagga tctggcggag gcggaagtgg cggaggggc    2700 tctgaagtgc agctggtgga gtctggggga ggcttagtga agcctggagg gtccctgaaa    2760
ctctcctgtg aagcctctag attcactttc agtagctatg ccatgtcttg ggttcgccag    2820
actccggaga gaggctgga gtgggtcgca gccattagtg gaggtggtag gtacacctac    2880
tatccagaca gtatgaaggg tcgattcacc atctccagag acaatgccaa gaatttcctg    2940
tacctgcaaa tgagcagtct gaggtctgag gacacggcca tgtattactg tgcaagacac    3000
tatgatggtt atcttgacta ctggggccaa ggcaccactc tcacagtctc ctcaacgcgt    3060
accacgacgc cagcgccgcg accaccaaca ccggcgccca catcgcgtc gcagcccctg    3120 tccctgcgcc cagaggcgtg ccggccagcg gcggggggcg cagtgcacac gagggggctg    3180
gacttcgcct gtgatatcta catctgggcg cccttggccg ggacttgtgg ggtccttctc    3240
ctgtcactgg ttatcaccct ttactgcaaa cggggcagaa agaaactcct gtatatattc    3300
aaacaaccat ttatgagacc agtacaaact actcaagagg aagatggctg tagctgccga    3360
tttccagaag aagaagaagg aggatgtgaa ctgagagtga agttcagcag gagcgcagac    3420 gccccgcgt accagcaggg ccagaaccag ctctataacg agctcaatct aggacgaaga    3480
gaggagtacg atgttttgga caagagacgt ggccgggacc ctgagatggg gggaaagccg    3540
agaaggaaga accctcagga aggcctgtac aatgaactgc agaaagataa gatggcggag    3600
gcctacagtg agattgggat gaaaggcgag cgccggaggg gcaaggggca cgatggcctt    3660
```

```
taccagggtc tcagtacagc caccaaggac acctacgacg cccttcacat gcaggccctg    3720
ccccctcgct aagcatgcac ctcgagatcg atccggatta gtccaatttg ttaaagacag    3780
gatatcagtg gtccaggctc tagttttgac tcaacaatat caccagctga agcctataga    3840
gtacgagcca tagataaaat aaaagatttt atttagtctc cagaaaaagg ggggaatgaa    3900
agaccccacc tgtaggtttg gcaagctagc ttaagtaacg ccattttgca aggcatggaa    3960
aaatacataa ctgagaatag agaagttcag atcaaggtca ggaacagatg aacagctga    4020 atatgggcca aacaggatat ctgtggtaag cagttcctgc cccggctcag ggccaagaac    4080
agatggaaca gctgaatatg gccaaacag gatatctgtg gtaagcagtt cctgccccgg    4140
ctcagggcca agaacagatg gtccccagat gcggtccagc cctcagcagt ttctagagaa    4200
ccatcagatg tttccagggt gccccaagga cctgaaatga ccctgtgcct tatttgaact    4260
aaccaatcag ttcgcttctc gcttctgttc gcgcgcttct gctccccgag ctcaataaaa    4320
gagcccacaa cccctcactc ggggcgccag tcctccgatt gactgagtcg cccgggtacc    4380
cgtgtatcca ataaaccctc ttgcagttgc atccgacttg tggtctcgct gttccttggg    4440
agggtctcct ctgagtgatt gactacccgt cagcggggg cttcacaca tgcagcatgt    4500 atcaaaatta atttggtttt ttttcttaag tatttacatt aaatggccat agtacttaaa    4560
gttacattgg cttccttgaa ataaacatgg agtattcaga atgtgtcata aatatttcta    4620
attttaagat agtatctcca ttggctttct acttttttctt ttatttttttt ttgtcctctg    4680 tcttccattt gttgttgttg ttgtttgttt gtttgtttgt tggttggttg gttaatttt    4740 ttttaaagat cctacactat agttcaagct agactattag ctactctgta acccagggtg    4800
accttgaagt catgggtagc ctgctgtttt agccttccca catctaagat tacaggtatg    4860
agctatcatt tttggtatat tgattgattg attgattgat gtgtgtgtgt gtgattgtgt    4920
ttgtgtgtgt gactgtgaaa atgtgtgtat gggtgtgtgt gaatgtgtgt atgtatgtgt    4980
gtgtgtgagt gtgtgtgtgt gtgtgtgcat gtgtgtgtgt gtgactgtgt ctatgtgtat    5040
gactgtgtgt gtgtgtgtgt gtgtgtgtgt gtgtgtgtgt gtgtgtgtgt tgtgaaaaaa    5100
tattctatgg tagtgagagc caacgctccg gctcaggtgt caggttggtt tttgagacag    5160
agtctttcac ttagcttgga attcactggc cgtcgtttta caacgtcgtg actgggaaaa    5220
ccctggcgtt acccaactta atcgccttgc agcacatccc cctttcgcca gctggcgtaa    5280
tagcgaagag gcccgcaccg atcgcccttc ccaacagttg cgcagcctga atggcgaatg    5340
gcgcctgatg cggtattttc tccttacgca tctgtgcggt atttcacacc gcatatggtg    5400
cactctcagt acaatctgct ctgatgccgc atagttaagc cagccccgac acccgccaac    5460
acccgctgac gcgccctgac gggcttgtct gctcccggca tccgcttaca gacaagctgt    5520
gaccgtctcc gggagctgca tgtgtcagag gttttcaccg tcatcaccga aacgcgcgat    5580
gacgaaaggg cctcgtgata cgcctatttt tataggttaa tgtcatgata taatggttt    5640 cttagacgtc aggtggcact tttcggggaa atgtgcgcgg aacccctatt tgtttatttt    5700
tctaaataca ttcaaatatg tatccgctca tgagacaata accctgataa atgcttcaat    5760
aatattgaaa aaggaagagt atgagtattc aacatttccg tgtcgccctt attccctttt    5820
ttgcggcatt ttgccttcct gtttttgctc acccagaaac gctggtgaaa gtaaaagatg    5880
ctgaagatca gttgggtgca cgagtgggtt acatcgaact ggatctcaac agcggtaaga    5940
tccttgagag ttttcgcccc gaagaacgtt ttccaatgat gagcactttt aaagttctgc    6000
```

```
tatgtggcgc ggtattatcc cgtattgacg ccgggcaaga gcaactcggt cgccgcatac    6060
actattctca gaatgacttg gttgagtact caccagtcac agaaaagcat cttacggatg    6120
gcatgacagt aagagaatta tgcagtgctg ccataaccat gagtgataac actgcggcca    6180
acttacttct gacaacgatc ggaggaccga aggagctaac cgcttttttg cacaacatgg    6240
gggatcatgt aactcgcctt gatcgttggg aaccggagct gaatgaagcc ataccaaacg    6300
acgagcgtga caccacgatg cctgtagcaa tggcaacaac gttgcgcaaa ctattaactg    6360
gcgaactact tactctagct tcccggcaac aattaataga ctggatggag gcggataaag    6420
ttgcaggacc acttctgcgc tcggcccttc cggctggctg tttattgct gataaatctg     6480 gagccggtga gcgtgggtct cgcggtatca ttgcagcact ggggccagat ggtaagccct    6540
cccgtatcgt agttatctac acgacgggga gtcaggcaac tatggatgaa cgaaatagac    6600
agatcgctga gataggtgcc tcactgatta agcattggta actgtcagac caagtttact    6660
catatatact ttagattgat ttaaaacttc atttttaatt taaaaggatc taggtgaaga    6720
tcctttttga taatctcatg accaaaatcc cttaacgtga gttttcgttc cactgagcgt    6780 cagacccccgt agaaaagatc aaaggatctt cttgagatcc ttttttttctg cgcgtaatct   6840 gctgcttgca acaaaaaaa ccaccgctac cagcggtggt ttgtttgccg gatcaagagc    6900
taccaactct ttttccgaag gtaactggct tcagcagagc gcagatacca aatactgtcc    6960
ttctagtgta gccgtagtta ggccaccact tcaagaactc tgtagcaccg cctacatacc    7020
tcgctctgct aatcctgtta ccagtggctg ctgccagtgg cgataagtcg tgtcttaccg    7080
ggttggactc aagacgatag ttaccggata aggcgcagcg tcgggctga acgggggggtt    7140 cgtgcacaca gcccagcttg gagcgaacga cctacaccga actgagatac ctacagcgtg    7200
agcattgaga aagcgccacg cttcccgaag ggagaaaggc ggacaggtat ccggtaagcg    7260
gcagggtcgg aacaggagag cgcacgaggg agcttccagg gggaaacgcc tggtatcttt    7320
atagtcctgt cgggtttcgc cacctctgac ttgagcgtcg attttttgtga tgctcgtcag    7380 ggggggcggag cctatggaaa aacgccagca acgcggcctt tttacggttc ctggcctttt    7440
gctggccttt tgctcacatg ttctttcctg cgttatcccc tgattctgtg ataaccgta     7500 ttaccgcctt tgagtgagct gataccgctc gccgcagccg aacgaccgag cgcagcgagt    7560
cagtgagcga ggaagcggaa gagcgcccaa tacgcaaacc gcctctcccc gcgcgttggc    7620
cgattcatta atgcagctgg cacgacaggt ttcccgactg gaaagcgggc agtgagcgca    7680
acgcaattaa tgtgagttag ctcactcatt aggcaccca ggctttacac tttatgcttc      7740
cggctcgtat gttgtgtgga attgtgagcg gataacaatt tcacacagga aacagctatg    7800
accatgatta cgcc                                                      7814
```

```
<210> SEQ ID NO 5
<211> LENGTH: 720
<212> TYPE: DNA
<213> ORGANISM: Artificial
<220> FEATURE:
<223> OTHER INFORMATION: chimeric antigen receptor

<400> SEQUENCE: 5
gacattgtga tgacccagtc tcacaaattc atgtccacat caattggagc cagggtcagc      60
atcacctgca aggccagtca ggatgtgaga actgctgtag cctggtatca acagaaacca     120
ggccagtctc ctaaaactact aatttactcg gcatcctacc ggtacactgg agtccctgat    180
cgcttcactg gcagtggatc tgggacggat ttcacttca ccatcagcag tgtgcaggct     240
```

```
gaagacctgg cagtttatta ctgtcagcaa cattatggta ctcctccgtg gacgttcggt    300
ggaggcacca agctggaaat caaaggcggc ggaggatctg cggaggcgg  aagtggcgga    360 ggggctctg  aagtgcagct ggtggagtct gggggaggct tagtgaagcc tggagggtcc    420
ctgaaactct cctgtgaagc ctctagattc actttcagta gctatgccat gtcttgggtt    480
cgccagactc cggagaagag gctggagtgg gtcgcagcca ttagtggagg tggtaggtac    540
acctactatc cagacagtat gaagggtcga ttcaccatct ccagagacaa tgccaagaat    600
ttcctgtacc tgcaaatgag cagtctgagg tctgaggaca cggccatgta ttactgtgca    660
agacactatg atggttatct tgactactgg ggccaaggca ccactctcac agtctcctca    720
```

<210> SEQ ID NO 6
<211> LENGTH: 108
<212> TYPE: PRT
<213> ORGANISM: Artificial
<220> FEATURE:
<223> OTHER INFORMATION: Light chain of scFv

<400> SEQUENCE: 6

Asp Ile Val Met Thr Gln Ser His Lys Phe Met Ser Thr Ser Ile Gly
1               5                   10                  15

Ala Arg Val Ser Ile Thr Cys Lys Ala Ser Gln Asp Val Arg Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Gly Thr Pro Pro
                85                  90                  95

Trp Thr Phe Gly Gly Gly Thr Lys Leu Glu Ile Lys
            100                 105

<210> SEQ ID NO 7
<211> LENGTH: 117
<212> TYPE: PRT
<213> ORGANISM: Artificial
<220> FEATURE:
<223> OTHER INFORMATION: Heavy chain of scFv

<400> SEQUENCE: 7

Glu Val Gln Leu Val Glu Ser Gly Gly Gly Leu Val Lys Pro Gly Gly
1               5                   10                  15

Ser Leu Lys Leu Ser Cys Glu Ala Ser Arg Phe Thr Phe Ser Ser Tyr
            20                  25                  30

Ala Met Ser Trp Val Arg Gln Thr Pro Glu Lys Arg Leu Glu Trp Val
        35                  40                  45

Ala Ala Ile Ser Gly Gly Gly Arg Tyr Thr Tyr Tyr Pro Asp Ser Met
    50                  55                  60

Lys Gly Arg Phe Thr Ile Ser Arg Asp Asn Ala Lys Asn Phe Leu Tyr
65                  70                  75                  80

-continued

```
Leu Gln Met Ser Ser Leu Arg Ser Glu Asp Thr Ala Met Tyr Tyr Cys
             85                  90                      95

Ala Arg His Tyr Asp Gly Tyr Leu Asp Tyr Trp Gly Gln Gly Thr Thr
            100                 105              110

Leu Thr Val Ser Ser
            115
```

METHODS AND COMPOSITIONS FOR CHIMERIC ANTIGEN RECEPTOR TARGETING CANCER CELLS

STATEMENT OF PRIORITY

This application is a continuation application of, and claims priority to, U.S. patent application Ser. No. 16/012,432, filed Jun. 19, 2018 (allowed), which claims the benefit, under 35 U.S.C. § 119(e), of U.S. Provisional Application Ser. No. 62/523,105, filed Jun. 21, 2017, the entire contents of each of which are incorporated by reference herein.

STATEMENT REGARDING ELECTRONIC FILING OF A SEQUENCE LISTING

A Sequence Listing in ASCII text format, submitted under 37 C.F.R. § 1.821, entitled 5470-802CT_ST25.txt, 32,787 bytes in size, generated on Apr. 12, 2019 and filed via EFS-Web, is provided in lieu of a paper copy. This Sequence Listing is hereby incorporated herein by reference into the specification for its disclosures.

FIELD OF THE INVENTION

The present invention is directed to chimeric antigen receptor (CAR) compositions and methods of their use in cancer immunotherapy.

BACKGROUND OF THE INVENTION

B7-H3 (CD276) is a type I transmembrane protein and a member of the B7 superfamily of ligands that has an inhibitory effect on T-cells. B7-H3 is highly expressed in several human malignancies and its expression correlates with poor survival. B7-H3 is of interest as a target of chimeric antigen receptor (CAR)-redirected T cells, since it is expressed in tumor cells, but has a restricted distribution in normal tissues. In view of the broad tumor expression of B7-H3, there is much interest in the applicability of the B7-H3.CAR derived from particular monoclonal antibodies for the treatment of many types of solid and liquid human tumors. This invention describes compositions and methods for a chimeric antigen receptor (CAR) that targets the B7-H3 (CD276) transmembrane protein.

The present invention overcomes previous shortcomings in the art by providing a chimeric antigen receptor (CAR) that targets the B7-H3 (CD276) transmembrane protein and methods of its use in treating cancer.

SUMMARY OF THE INVENTION

The present invention provides methods and compositions for the treatment of cancer, including treatment of cancer employing immunotherapy. In particular cases, the immunotherapy includes T lymphocytes engineered to target certain cancers.

Thus, in one embodiment, the present invention provides a chimeric antigen receptor (CAR) comprising the amino acid sequence:

(SEQ ID NO: 1)
MEFGLSWLFLVAILKGVQCDIVMTQSHKFMSTSIGARVSITCKASQDVRT

AVAWYQQKPGQSPKLLIYSASYRYTGVPDRFTGSGSGTDFTFTISSVQAE

DLAVYYCQQHYGTPPWTFGGGTKLEIKGGGGSGGGGSGGGGSEVQLVESG

GGLVKPGGSLKLSCEASRFTFSSYAMSWVRQTPEKRLEWVAAISGGGRYT

YYPDSMKGRFTISRDNAKNFLYLQMSSLRSEDTAMYYCARHYDGYLDYWG

QGTTLTVSSTRTTTPAPRPPTPAPTIASQPLSLRPEACRPAAGGAVHTRG

LDFACDIYIWAPLAGTCGVLLLSLVITLYCRSKRSRLLHSDYMNMTPRRP

GPTRKHYQPYAPPRDFAAYRSRVKFSRSADAPAYQQGQNQLYNELNLGRR

EEYDVLDKRRGRDPEMGGKPRRKNPQEGLYNELQKDKMAEAYSEIGMKGE

RRRGKGHDGLYQGLSTATKDTYDALHMQALPPR.

In another embodiment, the present invention provides a chimeric antigen receptor (CAR) comprising the amino acid sequence:

(SEQ ID NO: 2)
MEFGLSWLFLVAILKGVQCDIVMTQSHKFMSTSIGARVSITCKASQDVRT

AVAWYQQKPGQSPKLLIYSASYRYTGVPDRFTGSGSGTDFTFTISSVQAE

DLAVYYCQQHYGTPPWTFGGGTKLEIKGGGGSGGGGSGGGGSEVQLVESG

GGLVKPGGSLKLSCEASRFTFSSYAMSWVRQTPEKRLEWVAAISGGGRYT

YYPDSMKGRFTISRDNAKNFLYLQMSSLRSEDTAMYYCARHYDGYLDYWG

QGTTLTVSSTRTTTPAPRPPTPAPTIASQPLSLRPEACRPAAGGAVHTRG

LDFACDIYIWAPLAGTCGVLLLSLVITLYCKRGRKKLLYIFKQPFMRPVQ

TTQEEDGCSCRFPEEEEGGCELRVKFSRSADAPAYQQGQNQLYNELNLGR

REEYDVLDKRRGRDPEMGGKPRRKNPQEGLYNELQKDKMAEAYSEIGMKG

ERRRGKGHDGLYQGLSTATKDTYDALHMQALPPR.

In a further embodiment, the present invention provides a nucleic acid molecule encoding the CAR of this invention, including, in some embodiments, the nucleotide sequence of SEQ ID NO:3, which comprises a nucleotide sequence that encodes the amino acid sequence of SEQ ID NO:1 and in some embodiments, the nucleotide sequence of SEQ ID NO:4, which comprises a nucleotide sequence that encodes the amino acid sequence of SEQ ID NO:2. The present invention further provides vectors and cells comprising the nucleic acid molecule of this invention. The present invention also provides a nucleic acid molecule having the nucleotide sequence of SEQ ID NO:5.

In a further embodiment, the present invention provides a method of stimulating a T cell-mediated immune response to a B7-H3 expressing target cell population or tissue in a subject, comprising administering to the subject an effective amount of the nucleic acid molecule, vector and/or cell of this invention, thereby stimulating a T cell-mediated immune response to the B7-H3 expressing target cell population or tissue in the subject.

In additional embodiments, the present invention provides a method of providing an anti-tumor immunity in a subject, comprising administering to the subject an effective amount of the nucleic acid molecule, vector, and/or the cell of this invention, thereby providing an anti-tumor immunity in the subject.

The present invention further provides a method of treating a subject having a disease or disorder associated with elevated expression of B7-H3 (CD276) by a cell of the subject, comprising administering to the subject an effective amount of the nucleic acid molecule, vector, and/or cell of this invention, thereby treating the subject having the disease or disorder associated with elevated expression of B7-H3 by the cell of the subject.

In an additional embodiment, the present invention provides a method of generating a persisting population of genetically engineered T cells in a subject (e.g., a subject diagnosed with cancer), comprising administering to the subject a T cell genetically engineered to express the CAR of this invention, wherein the persisting population of genetically engineered T cells persists in the subject following administration.

In a further embodiment, the present invention provides a method of expanding a population of genetically engineered T cells in a subject (e.g., a subject diagnosed with cancer), comprising administering to the subject a T cell genetically engineered to express a CAR of this invention, wherein the administered genetically engineered T cell produces a population of progeny T cells in the subject.

In an additional embodiment, the present invention provides a method of treating cancer in a subject, comprising administering to the subject an effective amount of the nucleic acid molecule, vector and/or the cell of this invention, thereby treating cancer in the subject.

The present invention also provides a method of targeting a cancer cell and/or a cancer initiating cell (CIC) having a B7-H3 (CD276) antigen, comprising contacting the cancer cell and/or the CIC with a cell comprising the CAR of this invention.

Also provided herein is a method of detecting cancer cells and/or cancer initiating cells (CICs) in a *cell sample*, comprising: a) contacting the *cell sample* with the CAR of this invention under conditions whereby a binding complex can form; and b) detecting formation of the binding complex, wherein detection of the binding complex is indicative of cancer cells and/or CICs in the *cell sample*.

Another embodiment of this invention is a method of detecting cancer cells and/or cancer initiating cells (CICs) in a subject, comprising: a) contacting a cell sample obtained from the subject with the CAR of this invention under conditions whereby a binding complex can form; and b) detecting formation of the binding complex, wherein detection of the binding complex is indicative of the presence of cancer cells and/or CICs in the subject.

Further embodiments of the invention provide related nucleic acid molecules, recombinant expression vectors, host cells, populations of cells, antibodies or antigen binding portions thereof, antibody fragments and pharmaceutical compositions relating to the CARs of the invention.

BRIEF DESCRIPTION OF THE DRAWINGS

FIGS. 4A-F. B7-H3.CAR-Ts target PDAC cell lines in vitro. (4A) Six PDAC cell lines were co-cultured with control (NT) or B7-H3.CAR-Ts at the T cell to PDAC ratio of 1:5 or 1:10. PDAC tumor cell lines were labeled with green fluorescent protein (GFP). By day 7, PDAC (GFP+) and B7-H3.CAR-T cells (CD3+) were enumerated by flow cytometry. (4B) Statistics of the tumor cell frequency for T cell to PDAC ratio 1:5, and (4C) T cell to PDAC ratio 1:10 (n=4). (4D) IFNγ and (4E) IL2 released by control and B7-H3.CAR-Ts after 24 hours co-cultured with PDAC as measured by ELISA (n=4). (4F) CFSE-labeled B7-H3.CAR-Ts were co-cultured with PDAC for 5 days at 1:1 ratio. Proliferation of CAR-T cells was measured by CFSE dilution by flow cytometry. CFSE-labeled B7-H3.CAR-T cells alone were used as control, which is shown as filled gray peak.

DETAILED DESCRIPTION OF THE INVENTION

Figure 1A:
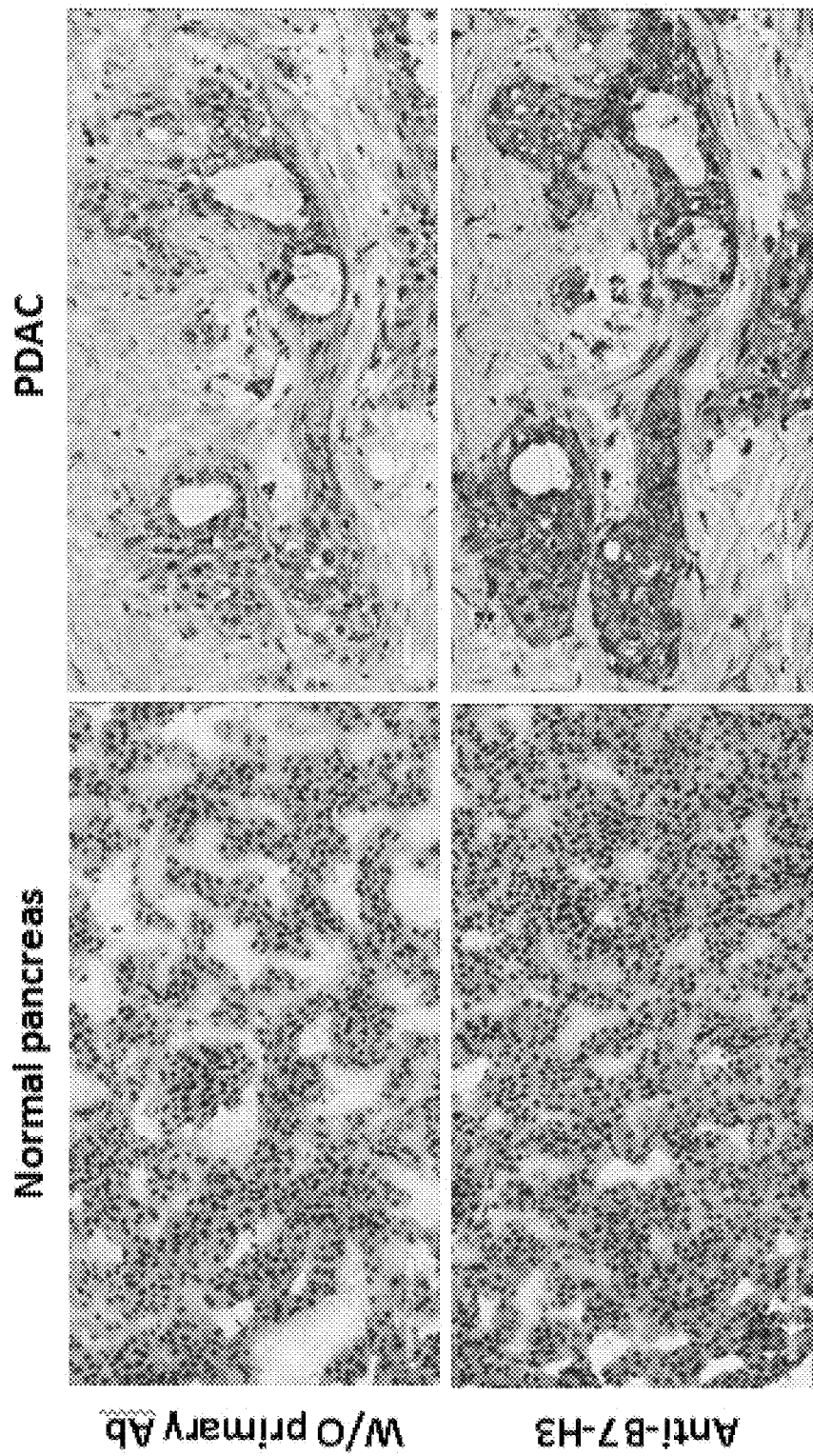
FIGS. 1A-C. B7-H3 is highly expressed in pancreatic cancer. (1A) Immunohistochemistry of frozen tissues of normal human pancreas and pancreatic ductal adenocarcinoma (PDAC). Staining was performed using the anti-B7-H3 mAb 376.96, from which the B7-H3.CAR was derived. The final concentration of the mAb was 1 µg/mL. Scale bars are 100 µm. Human PDAC tumor cell lines (1B) and primary pancreatic tumor cell lines derived from PDX (1C) were also stained with anti-B7-H3 mAb 376.96, and the expression of the antigen was assessed by flow cytometry.

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

Unless the context indicates otherwise, it is specifically intended that the various features of the invention described herein can be used in any combination. Moreover, the present invention also contemplates that in some embodiments of the invention, any feature or combination of features set forth herein can be excluded or omitted.

In the following description, certain details are set forth such as specific quantities, sizes, etc. so as to provide a thorough understanding of the present embodiments disclosed herein. However, it will be obvious to those skilled in the art that the present disclosure may be practiced without such specific details. In many cases, details concerning such considerations and the like have been omitted inasmuch as such details are not necessary to obtain a complete understanding of the present disclosure and are within the skills of persons of ordinary skill in the relevant art.

The present invention is based on the discovery of a chimeric antigen receptor (CAR) that targets cancer cells and/or cancer initiating cells (CICs) having a B7-H3 antigen. Accordingly, the present invention provides a chimeric antigen receptor (CAR) that targets cancer cells and/or CICs having a B7-H3 antigen, wherein the CAR comprises, consists essentially of and/or consists of the components described herein.

Thus, in one embodiment, the present invention provides a chimeric antigen receptor (CAR) comprising, consisting essentially of, or consisting of the amino acid sequence:

```
(B7-H3.CAR including CD28 co-stimulatory domain)
                                        (SEQ ID NO: 1)
MEFGLSWLFLVAILKGVQCDIVMTQSHKFMSTSIGARVSITCKASQDVRT

AVAWYQQKPGQSPKLLIYSASYRYTGVPDRFTGSGSGTDFTFTISSVQAE

DLAVYYCQQHYGTPPWTFGGGTKLEIKGGGGSGGGGSGGGGSEVQLVESG

GGLVKPGGSLKLSCEASRFTFSSYAMSWVRQTPEKRLEWVAAISGGGRYT

YYPDSMKGRFTISRDNAKNFLYLQMSSLRSEDTAMYYCARHYDGYLDYWG

QGTTLTVSSTRTTTPAPRPPTPAPTIASQPLSLRPEACRPAAGGAVHTRG

LDFACDIYIWAPLAGTCGVLLLSLVITLYCRSKRSRLLHSDYMNMTPRRP

GPTRKHYQPYAPPRDFAAYRSRVKFSRSADAPAYQQGQNQLYNELNLGRR

EEYDVLDKRRGRDPEMGGKPRRKNPQEGLYNELQKDKMAEAYSEIGMKGE

RRRGKGHDGLYQGLSTATKDTYDALHMQALPPR.
```

In another embodiment, the present invention provides a chimeric antigen receptor (CAR) comprising, consisting essentially of, or consisting of the amino acid sequence:

```
(B7-H3.CAR including 4-1BB co-stimulatory domain)
                                        (SEQ ID NO: 2)
MEFGLSWLFLVAILKGVQCDIVMTQSHKFMSTSIGARVSITCKASQDVRT

AVAWYQQKPGQSPKLLIYSASYRYTGVPDRFTGSGSGTDFTFTISSVQAE

DLAVYYCQQHYGTPPWTFGGGTKLEIKGGGGSGGGGSGGGGSEVQLVESG

GGLVKPGGSLKLSCEASRFTFSSYAMSWVRQTPEKRLEWVAAISGGGRYT

YYPDSMKGRFTISRDNAKNFLYLQMSSLRSEDTAMYYCARHYDGYLDYWG

QGTTLTVSSTRTTTPAPRPPTPAPTIASQPLSLRPEACRPAAGGAVHTRG

LDFACDIYIWAPLAGTCGVLLLSLVITLYCKRGRKKLLYIFKQPFMRPVQ

TTQEEDGCSCRFPEEEEGGCELRVKFSRSADAPAYQQGQNQLYNELNLGR

REEYDVLDKRRGRDPEMGGKPRRKNPQEGLYNELQKDKMAEAYSEIGMKG

ERRRGKGHDGLYQGLSTATKDTYDALHMQALPPR.
```

In particular embodiments, the chimeric antigen receptor (CAR) of this invention has one, two, three, four, or more components, and in some embodiments the one, two, three, four or more components facilitate targeting and/or binding of the CAR to the B7-H3 antigen-comprising cancer cell and/or CIC, although in some cases one or more components can be useful to promote and/or maintain growth and/or maturity of the cell comprising the CAR.

The present invention additionally provides a nucleic acid molecule encoding the CAR of this invention. In some embodiments, the nucleic acid molecule can comprise the nucleotide sequence of SEQ ID NO:3, which encodes a B7-H3 CAR including a CD28 co-stimulatory domain. In some embodiments, the nucleic acid molecule can comprise the nucleotide sequence of SEQ ID NO:4, which encodes a B7-H3 CAR including a 4-1BB co-stimulatory domain.

Further provided herein is a vector comprising the nucleic acid molecule of this invention.

In some embodiments, the present invention provides a cell comprising the CAR of this invention and in some embodiments, the present invention provides a cell comprising the nucleic acid molecule of this invention.

Nonlimiting examples of a cell of this invention include a αβT cell, a natural killer (NK) cell, a cytotoxic T lymphocyte (CTL), a regulatory T cell, a natural killer T (NKT) cell, a Th17 cell, a γδT cell, and any combination thereof.

In some embodiments, the present invention provides a cytotoxic T lymphocyte comprising a CAR that recognizes and binds B7-H3 antigen. The cytotoxic T lymphocyte can be transduced with a viral vector or transfected with a plasmid or nucleic acid construct comprising a nucleotide sequence encoding the CAR of this invention and in some embodiments the nucleotide sequence can be SEQ ID NO:3 and/or SEQ ID NO:4.

In certain embodiments, the present invention includes T lymphocytes engineered to comprise a chimeric antigen receptor having an antibody, antigen binding fragment and/or engineered antibody specific for B7-H3, part or all of a cytoplasmic signaling domain, and/or part or all of one or more costimulatory molecules, for example endodomains of costimulatory molecules. In specific embodiments, the antibody for B7-H3 is a single-chain variable fragment (scFv), although in certain aspects the antibody can be directed at other target antigens on the cell surface, such as HER2 or CD19, for example. In certain embodiments, a cytoplasmic signaling domain, such as those derived from the T cell receptor .zeta.-chain, can be included as at least part of the chimeric antigen receptor in order to produce stimulatory signals for T lymphocyte proliferation and effector function following engagement of the chimeric antigen receptor with the target antigen. Examples would include, but are not limited to, endodomains from co-stimulatory molecules such as CD28, 4-1BB, and OX40 or the signaling components of cytokine receptors such as interleukin 7 (IL7), interleukin 15 (IL15) and interleukin 12 (IL12). In particular embodiments, costimulatory molecules are employed to enhance the activation, proliferation and/or cytotoxicity of T cells produced by the CAR after antigen engagement. In specific embodiments, the costimulatory molecules can be CD28, OX40, and 4-1BB and cytokine receptors. Nonlimiting examples of cytokine receptors of this invention include IL7 and IL15.

Genetic engineering of human T lymphocytes to express tumor-directed chimeric antigen receptors (CAR) can produce antitumor effector cells that bypass tumor immune escape mechanisms that are due to abnormalities in protein-antigen processing and presentation.

In certain embodiments, the present invention provides cells specific for the B7-H3 antigen, wherein said cells have a chimeric antigen receptor on the cell surface that is produced by joining an extracellular antigen-binding domain derived from the B7-H3-specific antibody 376.96 to a cytoplasmic signaling domain derived from the T-cell receptor zeta-chain, and endodomains of the costimulatory molecules CD28 and/or 4-1BB, as nonlimiting examples.

In some embodiments, the CAR of this invention can comprise, consist essentially of and/or consist of the effector domain of the T cell receptor zeta chain or a related signal transduction endodomain derived from a T cell receptor. In some embodiments the chimeric antigen receptor is encoded by the nucleotide sequence of SEQ ID NO:3 or SEQ ID NO:4. Thus, the present invention further provides a vector (e.g., a viral vector) comprising the nucleotide sequence of SEQ ID NO:3 and/or SEQ ID NO:4 and the T lymphocytes of this invention can be transduced with a viral vector comprising the nucleotide sequence of SEQ ID NO:3 and/or SEQ ID NO:4 under conditions whereby the chimeric antigen receptor is produced in the T lymphocyte.

As used herein, the term "co-stimulatory molecule" refers to a molecular component that promotes activation, proliferation and effector function of a T cell after engagement of an antigen specific receptor. In some embodiments, the CAR of this invention can comprise one or more (e.g., 2, 3, 4, 5, 6, 7, 8, 9, 10, etc.) co-stimulatory molecules and/or active fragments thereof, nonlimiting examples of which include CD28, OX40, 4-1BB or any other co-stimulatory molecule and/or active fragment thereof now known or later identified, singly or in any combination.

In further embodiments, the chimeric antigen receptor (CAR) of this invention can further comprise a detectable moiety as would be known in the art and/or an effector molecule, nonlimiting examples of which include a drug, a toxin, a small molecule, an antibody, and/or an antibody fragment, singly or in any combination.

As used herein, the term "cytoplasmic signaling domain" refers to the component of a co-stimulatory molecule or cytokine receptor that exists inside the cell and is responsible for transducing the external signal received to the internal metabolic processes of the cell, thereby altering its phenotype and function.

In some embodiments of the present invention, the overexpression of B7-H3 by cancer cells allows these cells to be targeted in vitro and in vivo by B7-H3 CAR-expressing T cells, and in some embodiments, incorporation of endodomains (e.g., from both CD28 and OX40 molecules and/or from CD28 and/or from 4-1BB) mediates co-stimulation of the T lymphocytes, inducing T cell activation, proliferation, and/or cytotoxicity against B7-H3-positive cancer and/or CIC cells.

In particular embodiments of the invention, there are methods for killing cancer cells using genetically manipulated T-cells that express a chimeric antigen receptor (CAR) directed against the antigen B7-H3. In some embodiments, engagement (antigen binding) of this CAR leads to activation of the linked T-cell receptor C chain and the costimulatory molecules CD28 and 4-1BB.

In particular embodiments of the invention, the CAR receptor comprises a single-chain variable fragment (scFv) that recognizes B7-H3. The skilled artisan recognizes that scFv is a fusion protein of the variable regions of the heavy (VH) and light chains (VL) of immunoglobulins, connected with a short linker peptide of ten to about 25 amino acids. The linker may be rich in glycine for flexibility and/or it may have serine or threonine for solubility, in certain cases. In a particular embodiment, the 376.96 scFv antibody is used in the CAR of this invention. The scFv may be generated by methods known in the art.

In certain aspects, one can use cytokine exodomains or other ligand/receptor molecules as exodomains to provide targeting to the tumor cells.

The skilled artisan recognizes that T cells utilize co-stimulatory signals that are antigen non-specific to become fully activated. In particular cases they are provided by the interaction between co-stimulatory molecules expressed on the membrane of an antigen presenting cell (APC) and the T cell. In specific embodiments, the one or more costimulatory molecules in the chimeric antigen receptor come from the B7/CD28 family, TNF superfamily, or the signaling lymphocyte activation molecule (SLAM) family. Exemplary costimulatory molecules include one or more of the following in any combination: B7-1/CD80; CD28; B7-2/CD86; CTLA-4; B7-H1/PD-L1; ICOS; B7-H2; PD-1; B7-H3; PD-L2; B7-H4; PDCD6; BTLA; 4-1BB/TNFRSF9/CD137; CD40 Ligand/TNFSF5; 4-1BB Ligand/TNFSF9; GITR/TNFRSF18; BAFF/BLyS/TNFSF13B; GITR Ligand/TNFSF18; BAFF R/TNFRSF13C; HVEM/TNFRSF14; CD27/TNFRSF7; LIGHT/TNFSF14; CD27 Ligand/TNFSF7; OX40/TNFRSF4; CD30/TNFRSF8; OX40 Ligand/TNFSF4; CD30 Ligand/TNFSF8; TAC1/TNFRSF13B; CD40/TNFSF5; 2B4/CD244/SLAMF4;

CD84/SLAMF5; BLAME/SLAMF8; CD229/SLAMF3; CD2 CRACC/SLAMF7; CD2F-10/SLAMF9; NTB-A/SLAMF6; CD48/SLAMF2; SLAM/CD150; CD58/LFA-3; CD2; Ikaros; CD53; Integrin alpha 4/CD49d; CD82/Kai-1; Integrin alpha 4 beta 1; CD90/Thy1; Integrin alpha 4 beta 7/LPAM-1; CD96; LAG-3; CD160; LMIR1/CD300A; CRTAM; TCL1A; DAP12; TIM-1/KIM-1/HAVCR; Dectin-1/CLEC7A; TIM-4; DPPIV/CD26; TSLP; EphB6; TSLP R; and HLA-DR.

The effector domain is a signaling domain that transduces the event of receptor ligand binding to an intracellular signal that partially activates the T lymphocyte. Absent appropriate co-stimulatory signals, this event is insufficient for useful T cell activation and proliferation. A nonlimiting example of an effector domain of this invention is the effector domain of the T cell receptor zeta chain.

The present invention additionally provides embodiments of the amino acid sequences and nucleotide sequences of this invention wherein the amino acid sequence and/or the nucleotide sequence has at least 60% (e.g., 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94 95, 96, 97, 98, 99 or 100%) identity with the amino acid sequence and/or nucleotide sequences described herein. The present invention further encompasses all nucleotide sequences that encode the amino acid sequences described herein.

In further embodiments, the present invention provides a composition (e.g., a pharmaceutical composition) comprising, consisting essentially of and/or consisting of the CAR of this invention, the nucleic acid molecule of this invention, the vector of this invention and/or the cell of this invention, in a pharmaceutically acceptable carrier.

The present invention also provides methods employing the CAR of this invention. Thus, in one embodiment, the present invention provides a method of stimulating a T cell-mediated immune response to a B7-H3 expressing target cell population and/or tissue in a subject, comprising administering to the subject an effective amount of the CAR of this invention, the nucleic acid molecule of this invention, the vector of this invention, and/or the cell of this invention, thereby stimulating a T cell-mediated immune response to the B7-H3 expressing target cell population and/or tissue in the subject.

In another embodiment, the present invention provides a method of providing an anti-tumor immunity (e.g., an immune response to tumor cells) in a subject, comprising administering to the subject an effective amount of the CAR of this invention, the nucleic acid molecule of this invention, the vector of this invention, and/or the cell of this invention, thereby providing an anti-tumor immunity in the subject.

In a further embodiment, the present invention provides a method of treating a subject having a disease or disorder associated with elevated expression of B7-H3 (CD276) by a cell of the subject, comprising administering to the subject an effective amount of the CAR of this invention, the nucleic acid molecule of this invention, the vector of this invention, and/or the cell of this invention, thereby treating the subject having the disease or disorder associated with elevated expression of B7-H3 by the cell of the subject.

In addition, the present invention provides a method of generating a population of genetically engineered T cells in a subject (e.g., a subject diagnosed with cancer and/or otherwise in need thereof), comprising administering to the subject a T cell genetically engineered to express the CAR of this invention, wherein the population of genetically engineered T cells persists in the subject for a period of time (e.g., at least one week, one month two months, three months, four months, five months, nine months, one year, two years, five years, etc.) following administration to the subject.

Additionally provided herein is a method of expanding a population of genetically engineered cells in a subject (e.g., a subject diagnosed with cancer and/or a subject in need thereof), comprising administering to the subject a cell genetically engineered to express the CAR of this invention, wherein the administered genetically engineered cell produces a population of progeny cells in the subject.

In additional embodiments of this invention, a method is provided of treating cancer in a subject (e.g., a subject in need thereof), comprising administering to the subject an effective amount of the CAR of this invention, the nucleic acid molecule of this invention, the vector of this invention, and/or the cell of this invention, thereby treating cancer in the subject. In some embodiments, the subject of this method has had and/or is having therapy for cancer.

Thus, in an additional embodiment of this invention, the present invention provides a method of treating cancer in a subject, comprising administering to the subject cytotoxic T lymphocytes having a chimeric antigen receptor that recognizes a B7-H3 antigen on the surface of cancer cells and/or cancer initiating cells (CICs).

In further embodiments of this invention, a method is provided of preventing cancer in a subject (e.g., a subject in need thereof), comprising administering to the subject an effective amount of the CAR of this invention, the nucleic acid molecule of this invention, the vector of this invention, and/or the cell of this invention, thereby preventing cancer in the subject.

In one embodiment, the present invention provides a method of targeting a cancer cell and/or a cancer initiating cell (CIC) having a B7-H3 (CD276) antigen, comprising providing to the cancer cell and/or the CIC or contacting the cancer cell and/or the CIC with a cell comprising the CAR of this invention.

In some embodiments of this invention, the cell of this invention (e.g., a αβT cell, a natural killer (NK) cell, a cytotoxic T lymphocyte (CTL), a regulatory T cell, a natural killer T (NKT) cell, a Th17 cell, a γδT cell) can be an autologous cell from the subject to whom treatment is administered. In some embodiments, the cell of this invention can be from a different individual of the same species as the subject receiving treatment or from an individual of a different species from the subject receiving treatment.

In the methods of this invention, the cancer cell and/or CIC can be in vitro, ex vivo, and/or in vivo. In some embodiments, the cell can be in a subject. In some embodiments, the cell can be an autologous cell. In some embodiments, the cell is not an autologous cell. In some embodiments, the cell is of the same species of the subject. In some embodiments, the cell is of a species that is different than the species of the subject.

In further embodiments, the present invention provides a method of detecting cancer cells and/or cancer initiating cells (CICs) in a cell sample, comprising: a) contacting the cell sample with the CAR of this invention under conditions whereby a binding complex can form; and b) detecting formation of the binding complex, wherein detection of the binding complex is indicative of cancer cells and/or CICs in the cell sample.

In another embodiment, the present invention provides a method of detecting cancer cells and/or cancer initiating cells (CICs) in a subject, comprising: a) contacting a cell sample obtained from the subject with the CAR of this invention under conditions whereby a binding complex can form; and b) detecting formation of the binding complex, wherein detection of the binding complex is indicative of the presence of cancer cells and/or CICs in the subject.

In methods of this invention, the cell can be an αβT cell, a natural killer (NK) cell, a cytotoxic T lymphocyte (CTL), a regulatory T cell, a natural killer T (NKT) cell, a Th17 cell, a γδT cell and any combination thereof. In some embodiments, the cell can be an autologous cell. In some embodiments, the cell can be of the same species of the subject and in some embodiments, the cell can be of a species that is different than the species of the subject.

In some embodiments, the cancer of this invention can be a cancer associated with increased expression or overexpression of B7-H3 antigen and in some embodiments, cancer cells and CICs of this invention can overexpress the B7-H3 antigen relative to a noncancerous cell or a cancer cell of a cancer that is not associated with increased expression or overexpression of B7-H3 antigen.

In some embodiments, the cancer cells and/or CICs of this invention can be contacted with LDE225, an inhibitor of the sonic hedgehog homolog (SHH) pathway, before, during and/or after contacting with the CAR of this invention.

The term "cancer" as used herein is defined as disease characterized by the rapid and uncontrolled growth of aberrant cells. Cancer cells can spread locally or through the bloodstream and lymphatic system to other parts of the body, Nonlimiting examples of a cancer that can be treated according to the methods of this invention include B cell lymphoma, T cell lymphoma, myeloma, leukemia, hematopoietic neoplasias, thymoma, lymphoma, sarcoma, lung cancer, liver cancer, non-Hodgkins lymphoma, Hodgkins lymphoma, skin cancer, uterine cancer, cervical cancer, endometrial cancer, adenocarcinoma, breast cancer, pancreatic cancer, colorectal cancer, anal cancer, lung cancer, renal cancer, bladder cancer, liver cancer, prostate cancer, ovarian cancer, primary or metastatic melanoma, squamous cell carcinoma, basal cell carcinoma, brain cancer, angiosarcoma, hemangiosarcoma, head and neck carcinoma, thyroid carcinoma, soft tissue sarcoma, bone sarcoma, testicular cancer, gastrointestinal cancer, and any other cancer now known or later identified (see, e.g., Rosenberg (1996) *Ann. Rev. Med.* 47:481-491, the entire contents of which are incorporated by reference herein).

The term "autoimmune disease" as used herein is defined as a disorder that results from an autoimmune response. An autoimmune disease is the result of an inappropriate and excessive response to a self-antigen. Examples of autoimmune diseases include but are not limited to, Addison's disease, alopecia greata, ankylosing spondylitis, autoimmune hepatitis, autoimmune parotitis, Crohn's disease, diabetes (Type 1), dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, ulcerative colitis, among others.

In certain embodiments of the invention, methods of the present invention for clinical aspects are combined with other agents effective in the treatment of hyperproliferative disease, such as anti-cancer agents. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, and/or increasing the lifespan of a subject with cancer. More generally, these other compositions would be provided in a combined amount effective to kill or inhibit proliferation of the cancer cell. This process may involve contacting the cancer cells with the nucleic acid molecule, vector and/or cell of this invention and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the nucleic acid molecule, vector and/or cell of the invention and the other composition includes the second agent(s).

Tumor cell resistance to chemotherapy and radiotherapy agents represents a major problem in clinical oncology. One goal of current cancer research is to find ways to improve the efficacy of chemo- and radiotherapy by combining it with gene therapy. For example, the herpes simplex-thymidine kinase (HS-tK) gene, when delivered to brain tumors by a retroviral vector system, successfully induced susceptibility to the antiviral agent ganciclovir. In the context of the present invention, it is contemplated that cell therapy could be used similarly in conjunction with chemotherapeutic, radiotherapeutic, or immunotherapeutic intervention, in addition to other pro-apoptotic or cell cycle regulating agents.

Alternatively, the present inventive therapy may precede and/or follow the other agent treatment(s) by intervals ranging from minutes to weeks. In embodiments where the other agent and present invention are applied separately to the individual, one would generally ensure that a significant period of time did not expire between the time of each delivery, such that the agent and inventive therapy would still be able to exert an advantageously combined effect on the cell. In such instances, it is contemplated that one may contact the cell with the multiple modalities within about 12-24 h of each other and, more preferably, within about 6-12 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It is expected that the treatment cycles would be repeated as necessary. It also is contemplated that various standard therapies, as well as surgical intervention, may be applied in combination with the inventive cell therapy.

Cancer therapies also include a variety of combination therapies with both chemical and radiation based treatments. Combination chemotherapies include, for example, abraxane, altretamine, docetaxel, herceptin, methotrexate, novantrone, zoladex, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin and methotrexate, or any analog or derivative variant of the foregoing.

In specific embodiments, chemotherapy for B7-H3 positive cancer is employed in conjunction with the invention, for example before, during and/or after administration of the invention.

Other factors that cause DNA damage and have been used extensively include what are commonly known as gamma-rays, X-rays, and/or the directed delivery of radioisotopes to tumor cells. Other forms of DNA damaging factors are also contemplated such as microwaves and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted with," "provided to" and "exposed to," when applied to a cell, are used herein to describe the process by which a therapeutic agent (e.g., a CAR) is delivered to a target cell and/or are placed in direct juxtaposition with the target cell, e.g., under conditions that facilitate binding of the CAR to the target antigen in and/or on the target cell. In some embodiments, chemotherapy and/or radiation therapy can also be included before, after and/or during the contacting or exposing or providing to step to achieve cell killing or stasis, wherein both agents are delivered to a cell in a combined amount effective to kill the cell or prevent it from dividing.

Immunotherapeutics generally rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy could thus be used as part of a combined therapy, in conjunction with the present cell therapy. The general approach for combined therapy is discussed herein. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

Immunotherapy for a cancer of this invention may include interleukin-2 (IL-2) or interferon (IFN), for example.

In yet another embodiment, the secondary treatment can be a gene therapy in which a therapeutic polynucleotide is administered before, after, and/or at the same time as the present invention clinical embodiments. A variety of expression products are encompassed within the invention, including inducers of cellular proliferation, inhibitors of cellular proliferation, or regulators of programmed cell death.

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abilities of the present invention by establishment of an autocrine or paracrine effect on hyperproliferative cells. Increasing intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyerproliferative efficacy of the treatments. Inhibitors of cell adhesion are contemplated to improve the efficacy of the present invention. Examples of cell adhesion inhibitors are focal adhesion kinase (FAKs) inhibitors and lovastatin. It is further contemplated that other agents that increase the sensitivity of a hyperproliferative cell to apoptosis, such as the antibody c225, could be used in combination with the present invention to improve the treatment efficacy.

Definitions

As used herein, "a," "an" and "the" can mean one or more than one, depending on the context in which it is used. For example, "a" cell can mean one cell or multiple cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

As used herein, the transitional phrase "consisting essentially of" means that the scope of a claim is to be interpreted to encompass the specified materials or steps recited in the claim, "and those that do not materially affect the basic and novel characteristic(s)" of the claimed invention. See, *In re Herz*, 537 F.2d 549, 551-52, 190 USPQ 461, 463 (CCPA 1976) (emphasis in the original); see also MPEP § 2111.03. Thus, the term "consisting essentially of" when used in a claim of this invention is not intended to be interpreted to be equivalent to "comprising."

Also as used herein, "one or more" means one, two, three, four, five, six, seven, eight, nine, ten, 11, 12, 13, 14, 15, 16, 17, 18, 19, 20, etc.

Subjects that may be treated by the present invention include both human subjects for medical and/or therapeutic purposes and animal subjects for veterinary and drug screening and development purposes. Other suitable animal subjects are, in general, mammalian subjects such as primates, bovines, ovines, caprines, porcines, equines, felines, canines, lagomorphs, rodents (e.g., rats and mice), etc. Human subjects are the most preferred. Human subjects include fetal, neonatal, infant, juvenile, adult and geriatric subjects.

The term "anti-tumor effect" as used herein, refers to a biological effect which can be manifested by a decrease in tumor volume, a decrease in the number of tumor cells, a decrease in the proliferation rate, a decrease in the number of metastases, an increase in life expectancy, and/or amelioration of various physiological symptoms associated with the cancerous condition. An "anti-tumor effect" can also be manifested by the ability of the peptides, polynucleotides, cells and antibodies of the invention to prevent and/or delay the occurrence of tumor in the first place.

The term "auto-antigen" means, in accordance with the present invention, any self-antigen which is mistakenly recognized by the immune system as being foreign. Auto-antigens comprise, but are not limited to, cellular proteins, phosphoproteins, cellular surface proteins, cellular lipids, nucleic acids, and glycoproteins, including cell surface receptors.

As used herein, the term "autologous" is meant to refer to any material derived from the same individual to whom it is later to be re-introduced.

"Allogeneic" refers to a graft derived from a different animal of the same species, "Xenogeneic" refers to a graft derived from an animal of a different species.

"Treat" or "treating" as used herein refers to any type of treatment that imparts a benefit to a subject that has a disease or disorder or is at risk of having or developing the disease or disorder, including, for example, improvement in the condition of the subject (e.g., in one or more symptoms) and/or slowing of the progression of symptoms, etc.

As used herein, "prevent," "preventing" or "prevention" includes prophylactic treatment of the subject to prevent the onset or advancement of a disorder, as determined, e.g., by the absence or delay in the manifestation of symptoms associated with the disorder. As used herein, "prevent," "preventing" or "prevention" is not necessarily meant to imply complete abolition of symptoms.

"Treatment effective amount," "effective amount," "amount effective to treat" or the like as used herein means an amount of the antibody or fragment thereof or CAR or cell of this invention sufficient to produce a desirable effect upon a patient that has a disease, disorder and/or condition of this invention. This includes improvement in the condition of the patient (e.g., in one or more symptoms), delay in the progression of the disease, etc.

"Pharmaceutically acceptable" as used herein means that the compound or composition is suitable for administration to a subject to achieve the treatments described herein, without unduly deleterious side effects in light of the severity of the disease and necessity of the treatment.

"Antibody" or "antibodies" as used herein refers to all types of immunoglobulins, including IgG, IgM, IgA, IgD, and IgE. The term "immunoglobulin" includes the subtypes of these immunoglobulins, such as $IgG_1$, $IgG_2$, $IgG_3$, $IgG_4$, etc. The antibodies may be of any species of origin, including (for example) mouse, rat, rabbit, horse, or human, or may be chimeric or humanized antibodies. The term "antibody" as used herein includes antibody fragments which retain the capability of binding to a target antigen, for example, Fab, $F(ab')_2$, and Fv fragments, and the corresponding fragments obtained from antibodies other than IgG. Such fragments are also produced by known techniques. In some embodiments antibodies may be coupled to or conjugated to a detectable group or therapeutic group in accordance with known techniques.

Furthermore, the term "antibody" as used herein, is intended to refer to immunoglobulin molecules comprising four polypeptide chains, two heavy (H) chains and two light (L) chains inter-connected by disulfide bonds. Each heavy chain comprises a heavy chain variable region (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain (CL1). The VH and VL regions can be further subdivided into regions of hypervariability, termed complementary determining regions (CDR), interspersed with regions that are more conserved, termed framework regions (FR). In various embodiments of the antibody or antigen binding fragment thereof of the invention, the FRs may be identical to the human germline sequences, or may be naturally or artificially modified. Each VH and VL is composed of three CDRs and four FRs, arranged from amino-terminus to carboxy-terminus in the following order: FR1, CDR1, FR2, CDR2, FR3, CDR3, FR4.

In general, the antibodies and antigen binding fragments thereof of the present invention possess very high affinities, typically possessing $K_D$ values of from about $10^{-8}$ through about $10^{-12}$ M or higher, for example, at least $10^{-8}$ M, at least $10^{-9}$ M, at least $10^{-10}$ M, at least $10^{-11}$ M, or at least $10^{-12}$ M, when measured by binding to antigen presented on cell surface.

The antibodies and antigen binding fragments thereof of the present invention possess very high affinities, typically possessing $EC_{50}$ values of from about $10^{-8}$ through about $10^{-12}$ M or higher, for example, at least $10^{-8}$M, at least $10^{-9}$ M, at least $10^{-10}$ M, at least $10^{-11}$ M, or at least $10^{-12}$ M, when measured by binding to antigen presented on cell surface.

The term "antigen-binding portion" or "antigen-binding fragment" of an antibody (or simply "antibody portion" or "antibody fragment"), as used herein, refers to one or more fragments, portions or domains of an antibody that retain the ability to specifically bind to an antigen. It has been shown that fragments of a full-length antibody can perform the antigen-binding function of an antibody. Examples of binding fragments encompassed within the term "antigen-binding portion" of an antibody include (i) an Fab fragment, a monovalent fragment consisting of the VL, VH, CL1 and CH1 domains; (ii) an $F(ab')_2$ fragment, a bivalent fragment comprising two F(ab)' fragments linked by a disulfide bridge at the hinge region; (iii) an Fd fragment consisting of the VH and CH1 domains; (iv) an Fv fragment consisting of the VL and VH domains of a single arm of an antibody; (v) a dAb fragment (Ward et al. (1989) *Nature* 241:544-546), which consists of a VH domain; and (vi) an isolated complementary determining region (CDR). Furthermore, although the two domains of the Fv fragment, VL and VH, are coded for by separate genes, they can be joined, using recombinant methods, by a synthetic linker that enables them to be made as a single contiguous chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. Other forms of single chain antibodies, such as diabodies, are also encompassed (see e.g., Holliger et al. (1993) *Proc. Natl. Acad Sci. USA* 90:6444-6448).

The term "epitope" refers to an antigenic determinant that interacts with a specific antigen binding site in the variable region of an antibody molecule known as a paratope. A single antigen may have more than one epitope. Epitopes may be either conformational or linear. A conformational epitope is produced by spatially juxtaposed amino acids from different segments of one (or more) linear polypeptide chain(s). A linear epitope is an epitope produced by adjacent amino acid residues in a polypeptide chain. In certain embodiments, an epitope may include other moieties, such as saccharides, phosphoryl groups, or sulfonyl groups on the antigen.

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations, An "antibody light chain," as used herein, refers to the smaller of the two types of polypeptide chains present in all antibody molecules in their naturally occurring conformations, κ and λ light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

Amino acid as used herein refers to a compound having a free carboxyl group and a free unsubstituted amino group on the α carbon, which may be joined by peptide bonds to form a peptide active agent as described herein. Amino acids may be standard or non-standard, natural or synthetic, with examples (and their abbreviations) including but not limited to:

Asp=D=Aspartic Acid
Ala=A=Alanine
Arg=R=Arginine
Asn=N=Asparagine
Cys=C=Cysteine
Gly=G=Glycine
Glu=E=Glutamic Acid
Gln=Q=Glutamine
His=H=Histidine
Ile=I=Isoleucine
Leu=L=Leucine
Lys=K=Lysine
Met=M=Methionine
Phe=F=Phenylalanine
Pro=P=Proline
Ser=S=Serine
Thr=T=Threonine
Trp=W=Tryptophan
Tyr=Y=Tyrosine
Val=V=Valine
Orn=Ornithine
Nal=2-napthylalanine
Nva=Norvaline
Nle=Norleucine
Thi=2-thienylalanine
Pcp=4-chlorophenylalanine
Bth=3-benzothienyalanine
Bip=4,4'-biphenylalanine
Tic=tetrahydroisoquinoline-3-carboxylic acid
Aib=aminoisobutyric acid
Anb=α-aminonormalbutyric acid
Dip=2,2-diphenylalanine
Thz=4-Thiazolylalanine All peptide sequences mentioned herein are written according to the usual convention whereby the N-terminal amino acid is on the left and the C-terminal amino acid is on the right. A short line (or no line) between two amino acid residues indicates a peptide bond.

Basic amino acid" refers to any amino acid that is positively charged at a pH of 6.0, including but not limited to R, K, and H.

Aromatic amino acid" refers to any amino acid that has an aromatic group in the side-chain coupled to the alpha carbon, including but not limited to F, Y, W, and H.

Hydrophobic amino acid" refers to any amino acid that has a hydrophobic side chain coupled to the alpha carbon, including but not limited to I, L, V, M, F, W and C, most preferably I, L, and V.

Neutral amino acid" refers to a non-charged amino acid, such as M, F, W, C and A.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well-known to those of skill in the art. See, e.g., Pearson (1994) *Methods Mol. Biol.* 24: 307-331, herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-1soleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) *Science* 256: 1443 45, herein incorporated by reference. A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) *J. Mol. Biol.* 215: 403 410 and Altschul et al. (1997) *Nucleic Acids Res.* 25:3389 402, each of which is herein incorporated by reference in its entirety.

"Therapeutic group" means any suitable therapeutic group, including but not limited to radionuclides, chemotherapeutic agents and cytotoxic agents.

"Radionuclide" as described herein may be any radionuclide suitable for delivering a therapeutic dosage of radiation to a tumor or cancer cell, including but not limited to $^{227}$Ac, $^{211}$At, $^{131}$Ba, $^{77}$Br, $^{109}$Cd, $^{51}$Cr, $^{67}$Cu, $^{165}$Dy, $^{155}$Eu, $^{153}$Gd, $^{198}$Au, $^{166}$Ho, $^{113m}$In, $^{115m}$In, $^{123}$I, $^{125}$I, $^{131}$I, $^{189}$Ir, $^{191}$Ir, $^{192}$Ir, $^{194}$Ir, $^{52}$Fe, $^{55}$Fe, $^{59}$Fe, $^{177}$Lu, $^{109}$Pd, $^{32}$P, $^{226}$Ra, $^{186}$Re, $^{188}$Re, $^{153}$Sm, $^{46}$Sc, $^{47}$Sc, $^{72}$Se, $^{75}$Se, $^{105}$Ag, $^{89}$Sr, $^{35}$S, $^{177}$Ta, $^{117m}$Sn, $^{121}$Sn, $^{166}$Yb, $^{169}$Yb, $^{90}$Y, $^{212}$Bi, $^{119}$Sb, $^{197}$Hg, $^{97}$Ru, $^{100}$Pd, $^{101m}$Rh, and $^{212}$Pb.

"Cytotoxic agent" as used herein includes but is not limited to ricin (or more particularly the ricin A chain), aclacinomycin, diphtheria toxin. Monensin, Verrucarin A, Abrin, Vinca alkaloids, Tricothecenes, and Pseudomonas exotoxin A.

"Detectable group" as used herein includes any suitable detectable group, such as radiolabels (e.g. $^{35}$S, $^{125}$I, $^{131}$I, etc.), enzyme labels (e.g., horseradish peroxidase, alkaline phosphatase, etc.), fluorescence labels (e.g., fluorescein, green fluorescent protein, etc.), etc., as are well known in the art and used in accordance with known techniques.

Formulations and Administration

For administration in the methods of use described below, the active agent (e.g., the antibody or antigen-binding fragment thereof, cell, nucleic acid molecule and/or vector of this invention) will generally be mixed, prior to administration, with a non-toxic, pharmaceutically acceptable carrier substance (e.g., normal saline or phosphate-buffered saline), and will be administered using any medically appropriate procedure, e.g., parenteral administration (e.g., injection) such as by intravenous or intra-arterial injection.

The active agents described above may be formulated for administration in a pharmaceutical carrier in accordance with known techniques. See, e.g., Remington, *The Science And Practice of Pharmacy* (latest edition). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the subject. The carrier may be a liquid and is preferably formulated with the compound as a unit-dose formulation which may contain from 0.01 or 0.5% to 95% or 99% by weight of the active compound. The carrier may be sterile or otherwise free from contaminants that would be undesirable to administer or deliver to a subject.

Formulations of the present invention suitable for parenteral administration comprise sterile aqueous and non-aqueous injection solutions of the active compound, which preparations are preferably isotonic with the blood of the intended subject. These preparations may contain anti-oxidants, buffers, bacteriostats and solutes which render the formulation isotonic with the blood of the intended subject.

The active agents may be administered by any medically appropriate procedure, e.g., normal intravenous or intra-arterial administration. In certain cases, direct administration to a tumor and/or a body cavity, orifice and/or tissue containing a tumor may be desired.

Active agents may be provided in lyophilized form in a sterile aseptic container or may be provided in a pharmaceutical formulation in combination with a pharmaceutically acceptable carrier, such as sterile pyrogen-free water or sterile pyrogen-free physiological saline solution.

CAR-modified T cells of this invention may also serve as a type of vaccine for ex vivo immunization and/or in vivo therapy in a subject of this invention.

In some embodiments involving ex vivo immunization, at least one of the following occurs in vitro prior to administering the cell into a subject: i) expansion of the cells, ii) introducing a nucleic acid encoding a CAR of this invention to the cells, and/or iii) cryopreservation of the cells.

Ex vivo procedures are well known in the art and are discussed more fully below. Briefly, cells are isolated from a mammal (preferably a human) and genetically modified (i.e., transduced or transfected in vitro) with a vector expressing a CAR of this invention. The resulting CAR-modified cell can be administered to a subject of this invention to provide a therapeutic benefit. In some embodiments, the subject can be a human and the CAR-modified cell can be autologous with respect to the subject who is the recipient of the CAR-modified cells. Alternatively, the cells can be allogeneic, syngeneic or xenogeneic with respect to the subject who is the recipient of the CAR-modified cells.

In addition to using a cell-based vaccine for ex vivo immunization, the present invention also provides compositions and methods for in vivo immunization to elicit and/or enhance an immune response directed against an antigen in a subject of this invention.

Generally, the cells activated and expanded as described herein can be used in the treatment and/or prevention of diseases and/or disorders that arise in subjects; e.g., subjects who are immunocompromised or at risking of becoming immunocompromised.

CAR-modified T cells of the present invention may be administered either alone, or as a pharmaceutical composition in combination with diluents and/or with other components such as IL-2 and/or other cytokines and/or cell populations. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline, sterile saline and the like; carbohydrates such as glucose, mannose, sucrose or dextrans, mannitol; proteins; polypeptides or amino acids such as glycine; antioxidants; chelating agents such as EDTA and/or glutathione; adjuvants (e.g., aluminum hydroxide) and/or preservatives, singly or in any combination.

Pharmaceutical compositions of the present invention can be administered in a manner appropriate to the disease to be treated and/or prevented. The quantity and frequency of administration will be determined by such factors as the condition of the subject, as well as the type and severity of the subject's disease, although in some embodiments, appropriate dosages may be determined by clinical trials.

When "an immunologically effective amount," "an anti-tumor effective amount," "a tumor-inhibiting effective amount," or a "therapeutic amount" is indicated, the precise amount of the compositions of the present invention to be administered can be determined by a physician with consideration of individual differences in age, weight, tumor size, extent of infection or metastasis, and condition of the patient (subject). In some embodiments, a pharmaceutical composition comprising cells of this invention can be administered at a dosage of about $10^3$ to about $10^{10}$ cells/kg body weight, and in some embodiments, the dosage can be from about $10^5$ to about $10^6$ cells/kg body weight, including all integer values (e.g., $10^4$, $10^5$, $10^6$, $10^7, 10^8$, $10^9$) within those ranges.

The cell compositions of this invention can also be administered multiple times (e.g., hourly, four times daily, three times daily, two times daily, daily, twice weekly, three times weekly, weekly, monthly, bi-monthly, semi-annually, annually, etc.) at these dosages.

The cells of this invention can be administered by using infusion techniques that are commonly known in immunotherapy (see, e.g., Rosenberg et al. *New Eng. J. of Med.* 319:1676 (1988)). The optimal dosage and treatment regimen for a particular subject can readily be determined by one skilled in the art of medicine by monitoring the subject for signs of disease and adjusting the treatment accordingly.

In some embodiments, it may be desirable to administer activated T cells to a subject and then subsequently redraw blood (or have an apheresis performed), activate T cells therefrom as described herein, and reinfuse the subject with these activated and expanded T cells. This process can be carried out multiple times, e.g., weekly or every few weeks. In certain embodiments, T cells can be activated from blood draws of from about 10 cc to about 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocol may serve to select out certain populations of T cells.

Administration of the compositions of this invention can be carried out in any manner, including by aerosol inhalation, injection, ingestion, transfusion, implantation and/or transplantation. The compositions of this invention can be administered to a patient subcutaneously, intradermally, mtratumorally, intranodally, intramedullary, intramuscularly, by intravenous (i.v.) injection, and/or intraperitoneally. In some embodiments, the T cell compositions of the present invention can be administered to a subject by intradermal or subcutaneous injection. In another embodiment, the T cell compositions of the present invention can be administered by i.v. injection. In some embodiments, the compositions of T cells can be injected directly into a tumor, lymph node and/or site of infection.

In some embodiments of the present invention, cells activated and expanded using the methods described herein, or other methods known in the art where T cells are expanded to therapeutic levels, can be administered to a subject in conjunction with (e.g., before, concurrently and/or following) any number of relevant treatment modalities, In some embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytotoxin, fludaribine, cyclosporin, FK506, rapamycin, mycophenolic acid, steroids, FR901228, cytokines, and/or irradiation.

In some embodiments, the cell compositions of the present invention can be administered to a patient in conjunction with (e.g., before, concurrently and/or following) bone marrow transplantation, T cell ablative therapy using either chemotherapy agents such as fludarabine, external-beam radiation therapy (XRT), cyclophosphamide, or antibodies such as OKT3 or CAMPATH. In another embodiment, the cell compositions of the present invention can be administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects can receive an infusion of the expanded immune cells of the present invention. In an additional embodiment, expanded cells can be administered before and/or following surgery.

In the treatment of cancers or tumors the CARs and/or nucleic acid molecules encoding CARs of the present invention may optionally be administered in conjunction with other, different, cytotoxic agents such as chemotherapeutic or antineoplastic compounds or radiation therapy useful in the treatment of the disorders or conditions described herein (e.g., chemotherapeutics or antineoplastic compounds). The other compounds may be administered prior to, concurrently and/or after administration of the antibodies or antigen binding fragments thereof of this invention. As used herein, the word "concurrently" means sufficiently close in time to produce a combined effect (that is, concurrently may be simultaneously, or it may be two or more administrations occurring before or after each other)

As used herein, the phrase "radiation therapy" includes, but is not limited to, x-rays or gamma rays which are delivered from either an externally applied source such as a beam or by implantation of small radioactive sources.

Nonlimiting examples of suitable chemotherapeutic agents which may be administered with the antibodies or antigen binding fragments, cells, nucleic acid molecules and/or vectors as described herein include daunomycin, cisplatin, verapamil, cytosine arabinoside, aminopterin, democolcine, tamoxifen, Actinomycin D, Alkylating agents (including, without limitation, nitrogen mustards, ethylenimine derivatives, alkyl sulfonates, nitrosoureas and triazenes): Uracil mustard, Chlormethine, Cyclophosphamide (Cytoxan®), Ifosfamide, Melphalan, Chlorambucil, Pipobroman, Triethylene-melamine, Triethylenethiophosphoramine, Busulfan, Carmustine, Lomustine, Streptozocin, Dacarbazine, and Temozolomide; Antimetabolites (including, without limitation, folic acid antagonists, pyrimidine analogs, purine analogs and adenosine deaminase inhibitors): Methotrexate, 5-Fluorouracil, Floxuridine, Cytarabine, 6-Mercaptopurine, 6-Thioguanine, Fludarabine phosphate, Pentostatine, and Gemcitabine, Natural products and their derivatives (for example, vinca alkaloids, antitumor antibiotics, enzymes, lymphokines and epipodophyllotoxins): Vinblastine, Vincristine, Vindesine, Bleomycin, Dactinomycin, Daunorubicin, Doxorubicin, Epirubicin, Idarubicin, Ara-C, paclitaxel (paclitaxel is commercially available as Taxol®), Mithramycin, Deoxyco-formycin, Mitomycin-C, L-Asparaginase, Interferons (especially IFN-a), Etoposide, and Teniposide; Other anti-proliferative cytotoxic agents are navelbene, CPT-11, anastrazole, letrazole, capecitabine, reloxafine, cyclophosphamide, ifosamide, and droloxafine. Additional anti-proliferative cytotoxic agents include, but are not limited to, melphalan, hexamethyl melamine, thiotepa, cytarabin, idatrexate, trimetrexate, dacarbazine, L-asparaginase, camptothecin, topotecan, bicalutamide, flutamide, leuprolide, pyridobenzoindole derivatives, interferons, and interleukins. Preferred classes of antiproliferative cytotoxic agents are the EGFR inhibitors, Her-2 inhibitors, CDK inhibitors, and Herceptin® (trastuzumab). (see, e.g., U.S. Pat. Nos. 6,537,988; 6,420,377). Such compounds may be given in accordance with techniques currently known for the administration thereof.

Antibodies of the invention include antibodies that are modified, i.e., by the covalent attachment of any type of molecule to the antibody such that covalent attachment does not prevent the antibody from specifically binding to its binding site. For example, antibodies of the invention may be modified, e.g., by glycosylation, acetylation, pegylation, phosphorylation, amidation, or with other protecting/blocking groups, proteolytic cleavage, linkage to a cellular ligand or other protein, etc. Any of numerous chemical modifications may be carried out by known techniques, including but not limited to specific chemical cleavage, acetylation, formylation, metabolic synthesis of tunicamycin, etc. Additionally, the antibodies may contain one or more non-classical amino acids.

Monoclonal antibodies can be prepared using a wide variety of techniques including the use of hybridoma, recombinant, and phage display technologies, or a combination thereof. For example, monoclonal antibodies can be produced using hybridoma techniques including those taught, for example, in Harlow et al., *Antibodies: A Laboratory Manual*, (Cold Spring Harbor Laboratory Press, 2nd ed. 1988); and Hammerling et al., *Monoclonal Antibodies and T-Cell Hybridomas* 563-681 Elsevier, N.Y., 1981). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and known. Briefly, mice are immunized with an antigen or a cell expressing such antigen. Once an immune response is detected, e.g., antibodies specific for the antigen are detected in the mouse serum, the mouse spleen is harvested and splenocytes isolated. The splenocytes are then fused by known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide or antigen of the invention. Ascites fluid, which generally contains high levels of antibodies, can be generated by immunizing mice with positive hybridoma clones.

Examples of techniques which can be used to produce single-chain Fvs (scFv) and antibodies include those described in U.S. Pat. Nos. 4,946,778 and 5,258,498; Huston et al. *Methods in Enzymology* 203:46-88 (1991); Shu et al. *PNAS* 90:7995-7999 (1993); and Skerra et al. *Science* 240: 1038-1040 (1988).

The term "humanized" as used herein refers to antibodies from non-human species whose amino acid sequences have been modified to increase their similarity to antibody variants produced naturally in humans. Thus, humanized antibodies are antibody molecules from a non-human species antibody that binds the desired antigen, having one or more complementarity determining regions (CDRs) from the non-human species and framework regions from a human immunoglobulin molecule. Often, framework residues in the human framework regions will be substituted with the corresponding residue from the donor antibody to alter, preferably to improve, antigen binding and/or reduce immunogenicity of the humanized antibody in a subject. These framework substitutions are identified by methods well known in the art, e.g., by modeling of the interactions of the CDR and framework residues to identify framework residues important for antigen binding and/or immunogenicity and sequence comparison to identify unusual framework residues at particular positions. (See, e.g., Queen et al. U.S. Pat. No. 5,585,089; Riechmann et al. *Nature* 332:323 (1988), which are incorporated herein by reference in their entireties.) Antibodies can be humanized using a variety of techniques known in the art including, for example, CDR-grafting (see, e.g., U.S. Pat. Nos. 5,225,539; 5,530,101; and 5,585,089), veneering or resurfacing (see, e.g., EP Patent No. 592,106; EP Patent No. 519,596; Padlan, *Molecular Immunology* 28(4/5):489-498 (1991); Studnicka et al., *Protein Engineering* 7(6):805-814 (1994); Roguska. et al., *PNAS* 91:969-973 (1994)), and chain shuffling (U.S. Pat. No. 5,565,332). A detailed description of the production and characterization of the humanized monoclonal antibodies of the present invention is provided in the Examples section herein.

Completely human antibodies are desirable for therapeutic treatment, diagnosis, and/or detection of human subjects. Human antibodies can be made by a variety of methods known in the art including phage display methods described above using antibody libraries derived from human immunoglobulin sequences. See, e.g., U.S. Pat. Nos. 4,444,887 and 4,716,111.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, *Int. Rev. Immunol.* 13:65-93). For a detailed discussion of this technology for producing human antibodies and human monoclonal antibodies and protocols for producing such antibodies, see, e.g., U.S. Pat. Nos. 5,413,923; 5,625,126; 5,633,425; 5,569,825; 5,661,016; 5,545,806; 5,814,318 and 5,939,598.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., *Bio/technology* 12:899-903 (1988)).

Further, antibodies to the polypeptides of the invention can, in turn, be utilized to generate anti-1diotype antibodies that "mimic" polypeptides of the invention using techniques well known to those skilled in the art. (See, e.g., Greenspan & Bona, *FASEB J.* 7(5):437-444; (1989) and Nissinoff, *J. Immunol.* 147(8):2429-2438 (1991)). For example antibodies which bind to and competitively inhibit polypeptide multimerization and/or binding of a polypeptide of the invention to a ligand can be used to generate anti-1diotypes that "mimic" the polypeptide multimerization and/or binding domain and, as a consequence, bind to and neutralize polypeptide and/or its ligand. Such neutralizing anti-1diotypes or Fab fragments of such anti-1diotypes can be used in therapeutic regimens to neutralize polypeptide ligand. For example, such anti-1diotypic antibodies can be used to bind a polypeptide of the invention and/or to bind its ligands/receptors, and thereby block its biological activity.

The invention further provides polynucleotides comprising a nucleotide sequence encoding a chimeric antigen receptor of the invention as described above. The polynucleotides may be obtained, and the nucleotide sequence of the polynucleotides determined, by any method known in the art. For example, if the nucleotide sequence of the components of the chimeric antigen receptor are known, a polynucleotide encoding the components may be assembled from chemically synthesized oligonucleotides, which involves the synthesis of overlapping oligonucleotides containing portions of the sequence encoding the components of the chimeric antigen receptor, annealing and ligation of those oligonucleotides, and then amplification of the ligated oligonucleotides by polymerase chain reaction (PCR). Alternatively, a polynucleotide encoding a chimeric antigen receptor may be generated from nucleic acid from a suitable source. Amplified nucleic acids generated by PCR may then be cloned into replicable cloning vectors using any method well known in the art.

The present invention is explained in greater detail in the following non-limiting examples. The following examples are presented in order to more fully illustrate the preferred embodiments of the invention. They should in no way, however, be construed as limiting the broad scope of the invention.

EXAMPLES

Example 1

B7-H3 (CD276) is a type I transmembrane protein and a member of the B7 superfamily of ligands that has an inhibitory effect on T-cells. B7-H3 is highly expressed in several human malignancies and its expression correlates with poor survival. We have selected B7-H3 as a target of chimeric antigen receptor (CAR)-redirected T cells, since it is expressed in tumor cells, but has a restricted distribution in normal tissues. Noteworthy, the mAb 376.96—from which we have derived the B7-H3-specific CAR targets a defined B7-H3 epitope that is not detectable in normal tissues, thus further minimizing potential side effects due to "on target but off tumor" recognition. Furthermore, this epitope is highly expressed in cancer initiating cells and tumor-associated vasculature and fibroblasts. We have generated a CAR from the single chain Fv (scFv) obtained from the mAb 376.96. We found that B7-H3.CAR can be stably expressed by human T lymphocytes upon gene transfer and that B7-H3.CAR-modified T cells can specifically recognize and efficiently eliminate B7-H3 positive cells, and cross-react with both human and murine B7-H3. We have found that B7-H3 highly express on pancreatic cancer (PDAC) cell lines, which can be efficiently eliminated by B7-H3.CAR-Ts (using either CD28 or 4-1-BB as co-stimulatory domains) in vitro. In vivo experiments showed that B7-H3.CAR-T cells effectively target pancreatic tumor cells both in systemic metastatic model and orthotopic pancreas model in NSG mice. In view of the broad tumor expression of B7-H3, we anticipate the applicability of the B7-H3.CAR derived from the mAb 376.96 for the treatment of many types of solid and liquid human tumors.

Cell Lines.

Human pancreatic tumor cell lines Panc-1, BxPC-3, Panc-10.05, Capan-1, Hpaf-II and AsPC-1 were purchased from American Type Culture Collection (ATCC). 293T, Phenix Eco and Capan-1 cell lines were cultured in IMDM (Gibco, Invitrogen) supplemented with 10% FBS (Sigma), 2 mM GlutaMax (Gibco). BxPC-3, Panc-10.05, KPC-4662 were cultured in RPMI1640 (Gibco) supplemented with 10% FBS and 2 mM GlutaMax. AsPC-1 was cultured in RPMI1640 (Gibco) supplemented with 10% FBS, 2 mM GlutaMax and 1 mM Sodium pyruvate (Gibco). Panc-1 cells were cultured in DMEM (GIBCO) supplemented with 10% FBS and 2 mM GlutaMax. Hpaf-II was cultured in MEM (Gibco) supplemented with 10% FBS and 2 mM GlutaMax. Penicillin (100 unit/mL) (Gibco) and streptomycin (100 µg/mL) (Gibco) were added to all cell culture mediums. Cells were maintained in a humidified atmosphere containing 5% $CO_2$ at 37° C. Panc-1, Panc-10.05, BxPC-3, Hpaf-II, Capan-1 and Aspc-1 cells were transduced with a retroviral vector encoding the eGFP, and Raji cell was transduced with retroviral vectors encoding either human or murine B7-H3 cdna. The murine pancreatic tumor cell line KPC-4662 was transduced with a retroviral vector encoding the murine B7-H3 cdna. Panc-1 and BxPC-3 cells were also transduced with a retroviral vector encoding the eGFP-Firefly-Luciferase (eGFP-FFluc) gene. All lines were routinely checked over the course of the experiments and always found mycoplasma free and routinely validated by flow cytometry for surface markers and functional readouts as needed.

Plasmid Construction and Retrovirus Production.

Figure 3A:
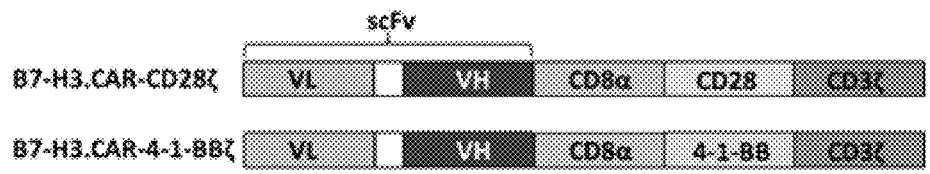
FIGS. 3A-G. B7-H3.CAR-T cells recognize human and mouse B7-H3. (3A) Schematic structure of the retroviral vector SFG encoding the B7-H3.CARs including either CD28 or 4-1BB co-stimulatory domains. (3B) Representative expression of the B7-H3.CARs in transduced human T cells. CAR expression was detected using an anti-mouse-FAB antibody and analyzed by flow cytometry. (3C) The human lymphoma tumor cell line Raji was engineered to express either the two human isoforms of B7-H3 (2Ig-hB7-H3 or 4Ig-hB7-H3) or the mouse isoform (mB7-H3) via retrovirus gene transfer. Single clones were then selected. The anti-B7-H3 mAb 376.96 recognizes both human and mouse B7-H3, as assessed by flow cytometry. (3D) Wild type (WT) Raji cells and Raji cells modified to express either human or mouse B7-H3 were co-cultured with either control T cells or B7-H3.CAR-Ts (1:1 ratio). By day 5, tumor cells (CD19+) and B7-H3.CAR-Ts (CD3+) were enumerated by flow cytometry. (3E) Statistics of the tumor cell frequency by day 5 of co-culture (n=4). (3F) IFNγ and (3G) IL2 released by control T cells and B7-H3.CAR-T cells after 24 hours of co-cultured with Raji cells as measured by ELISA (n=4).

The full-length human 2Ig-B7-H3 (accession number NM_001329628) and 4Ig-B7-H3 (accession number NM_001024736) genes were amplified by PCR from cDNA generated from Panc-1 cell line, and cloned into the retroviral vector SFG using NcoI and XhoI restriction sites. Murine B7-H3 (accession number NM_133983) was amplified by PCR from a plasmid obtained from InVivogene (San Diego, Calif.) and cloned into the retroviral vector SFG using NcoI and MluI restriction sites. The scFv.376.96 specific for human B7-H3, was cloned into the retroviral vector SFG using NcoI and MluI restriction sites, and the entire cassette of the B7-H3.CARs are illustrated in FIG. 3A. The retroviral supernatant was prepared as previously described. Briefly, 293T cells were cotransfected with 3 plasmids (the retroviral construct, Peg-Pam-e encoding for gag-pol, and RDF encoding for the RD114 envelop), using the GeneJuice transfection reagent (Novagen), and supernatants were collected at 48 and 72 hours later.

T Cell Transduction and Expansion.

Buffy coats from healthy donors were obtained through the Gulf Coast Regional Blood Center, Houston, Tex. Peripheral blood mononuclear cells (PBMCs) were isolated with Lymphoprep density separation (Fresenius Kabi Norge), were activated using 1 µg/mL anti-CD3 (Miltenyi Biotec) and 1 µg/mL anti-CD28 (BD Biosciences) antibodies coated plates. On day 3, T lymphocytes were transduced with retroviral supernatants using retronectin-coated plates (Takara Bio Inc., Shiga, Japan). After removal from the retronectin plates, T cells were expanded in complete medium (45% RPMI-1640 and 45% Click's medium (Irvine Scientific), 10% FBS (Hyclone), 2 mM GlutaMAX, 100 unit/mL of Penicillin and 100 µg/mL of streptomycin) with IL-7 (10 ng/mL; PeproTech) and IL-15 (5 ng/mL; PeproTech), changing medium every 2-3 days. On day 12-14, cells were collected for in vitro or in vivo experiments. T cells were cultured in IL-7/IL-15 depleted medium for two days prior to functional assays.

Immunohistochemistry.

Frozen normal human tissue microarrays and normal murine tissue microarrays were purchased from US Biomax. Frozen pancreatic cancer samples were obtained from the Tissue Procurement Facility at the UNC Lineberger Comprehensive Cancer Center. Tissues were sectioned by the Histology Research core facility at University of North Carolina. Slides were fixed in 4% PFA in PBS for 15 min, dried for 30 min at room temperature and blocked with 1% BSA and 10% horse serum (Company) in PBS with 0.05% tween-20. Slides were stained with the primary antibody specific for human B7-H3 (clone 376.96, 1:1000 dilution) at 4° C. overnight, and probed with HRP polymer conjugated goat anti-mouse secondary antibody (Dako, code K4000, 1:8 dilution at 25° C. for 1.5 h). Slides were developed using DAB chromogen (Vector Labs), counterstained with CAT hematoxylin (Biocare medical), dehydrated in ethanol, and cleared in xylene (Fisher chemical). Cover slips were added using histological mounting medium (Fisher, toluene solution). Stained TMA slides were digitally imaged at 20× objective using the Aperio ScanScope XT (Leica). Tissue microarray slides were de-arrayed to visualize individual cores and each core was visually inspected. Folded tissues were excluded from the analysis using a negative pen, and all other artifacts were automatically excluded with the Aperio Genie software. The B7-H3 staining was measured using Aperio membrane v9 (cell quantification) algorithm. Percentage of positive cells obtained with this algorithm at each intensity level (negative, low, medium, high) were used to calculate the H-Score using the formula: H-Score=(% at 1+)*1+(% at 2+)*2+(% at 3+)*3. The Aperio color deconvolution v9 algorithm with the Genie classifier was also applied to calculate the area and intensity of the positive stain and generate a Score (0-300).

ELISA

T cells ($5 \times 10^5$ or $1 \times 10^5$) were co-cultured with tumor cells ($5 \times 10^5$) in a 24 well plate without exogenous cytokines. After 24 hours, supernatants were collected and cytokines (interferon gamma (IFNγ) and interleukin 2 (IL2)) were measured by using ELISA kit (R&D system) following manufacturer's instructions. Each supernatant was measured in triplicate.

Flow Cytometry.

We performed flow cytometry using Abs specific to CD45, CD56, CD8, CD4, CD3, CD45RA, CD45RO, CD62L, hB7-H3 (clone 7-517), mB7-H3 clone MIH32), mCD3, mCD4, mCD8, mCD11b, mCD11c, mLy6cG, mCD19 (all from Becton Dickinson, San Jose, Calif.) and CCR7 (from E&D) conjugated with BV421, AF488, FITC, PE, PE-cy7, PerCP-cy5.5, APC, and APC-cy7 fluorochromes. Expression of B7-H3 in tumor cell lines was assessed with anti-B7-H3 specific Abs (clone 7-517 from BD, and clone 376.96). The expression of B7-H3.CAR was detected using Protein-L (Genscript) and Anti-Fab antibody (Jackson ImmunoResearch Laboratories INC.). Samples were analyzed with BD FACScanto II or BD FACSfortessa with the BD Diva software (BD Biosciences), for each sample we acquired a minimum of 10,000 events, and data was analyzed using Flojo 10.

Long-Term In Vitro Cytotoxic Activity.

Tumor cells were seeded in 24-well plates at a concentration of $5 \times 10^5$/well. T cells were added to the culture at different ratios (E:T of 1:1; 1:5, or 1:10) without the addition of exogenous cytokines. Cells were analyzed by day 5-7 to measure residual tumor cells and T cells by FACS. Dead cells were removed by Zombie Aqua (Biolegend) staining, T cells and tumor cells were identified by the expression of CD3, GFP (pancreatic cancer cell lines and fibroblast cells), CD19 (Raji, Raji-2IgB7-H3, Raji-4IgB7-H3 and Raji-mB7-H3) and mB7-H3 (KPC-4662 and KPC-4662-mB7-H3).

Proliferation Assay.

T cells were labeled with 1.5 mM carboxyfluorescein diacetate succinimidyl ester (CFSE; Invitrogen) and plated with tumor cell targets at an E:T ratio of 1:1. CFSE dilution was measured on $CD3^+$ T cells by day 5 using flow cytometry.

Xenogenic Mouse Models.

Figure 6A:
FIGS. 6A-J. B7-H3.CAR-Ts showed antitumor activity in xenograft model. (6A) Schema of the orthotopic mouse models. FFluc labeled Panc-1 ($2 \times 10^5$/mouse) or BxPC-3 ($1 \times 10^5$/mouse) human PDAC tumor cell lines were implanted into the pancreas of NSG mice. By day 12, mice were infused with either control CD19.CAR-T cells or B7-H3.CAR-T cells encoding either CD28 or 4-1BB co-stimulatory domains ($10^7$ cells/mouse by intravenous (i.v.) route). Tumor growth was monitored by luminescence imaging weekly after T cell infusion. (6B) Bioluminescence of Panc-1 orthotopic model. (6C) Representative ultrasound (US) measurement of Panc-1 by day 50 after tumor implant in mice treated with CD19.CAR-T cells. (6D) Bioluminescence signal measurements of Panc-1. (6E) Bioluminescence of BxPC-3 orthotopic model. (6F) Bioluminescence signal measurement of BxPC-3. (6G) Kaplan-Meier survival curve analysis of the BxPC-3 orthotopic model. (6H) Schema of the metastatic model of Panc-1. (6I) Bioluminescence of Panc-1 metastatic model. (6J) Bioluminescence signal measurement of metastatic Panc-1.
Figure 6B:
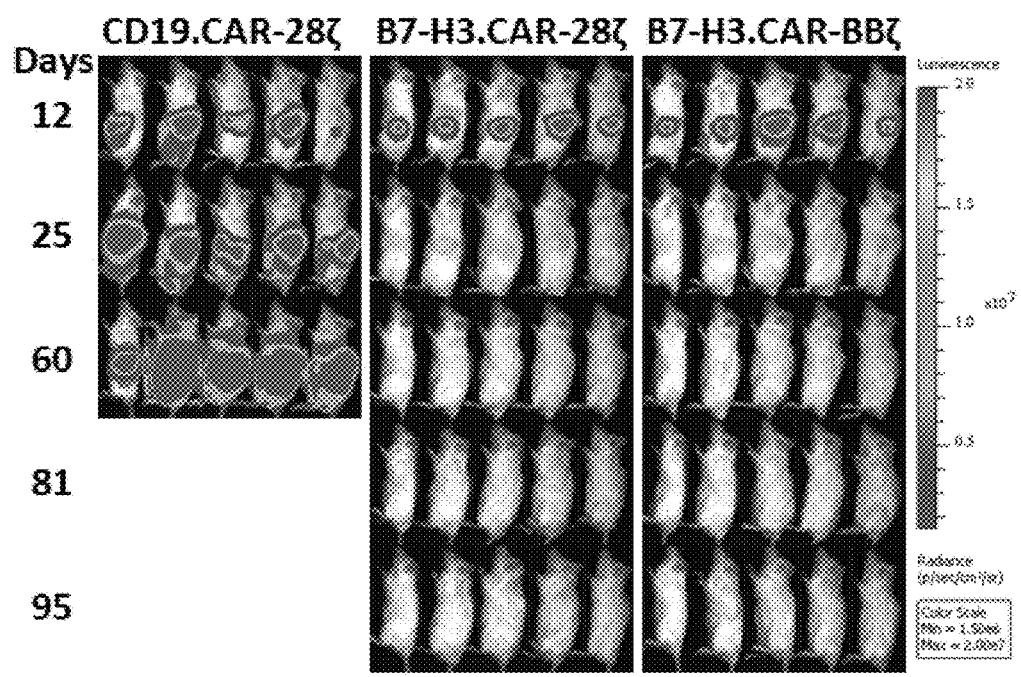
Figure 6C:
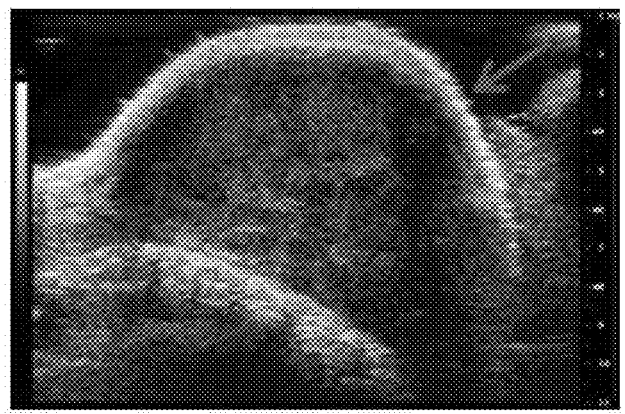
Figure 6D:
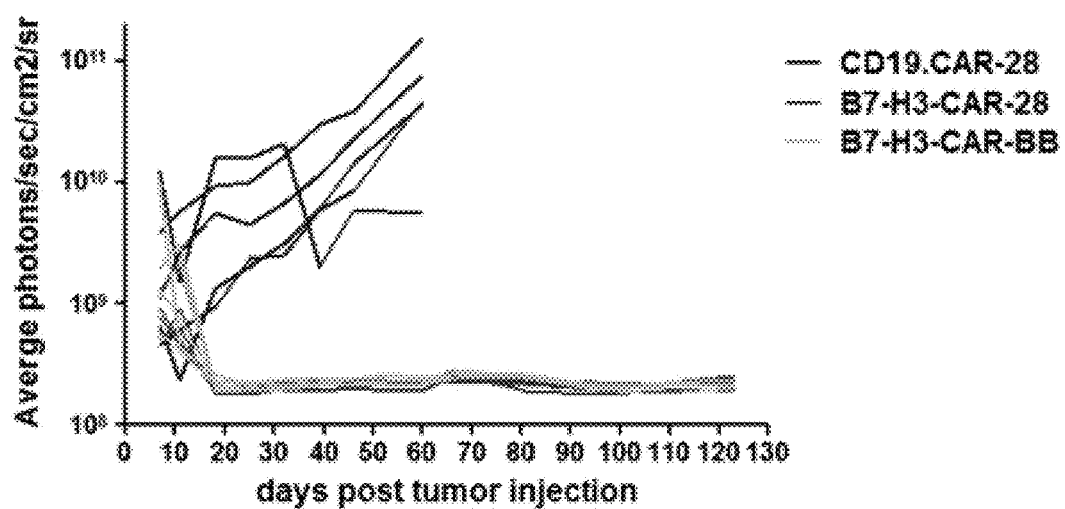
Figure 6E:
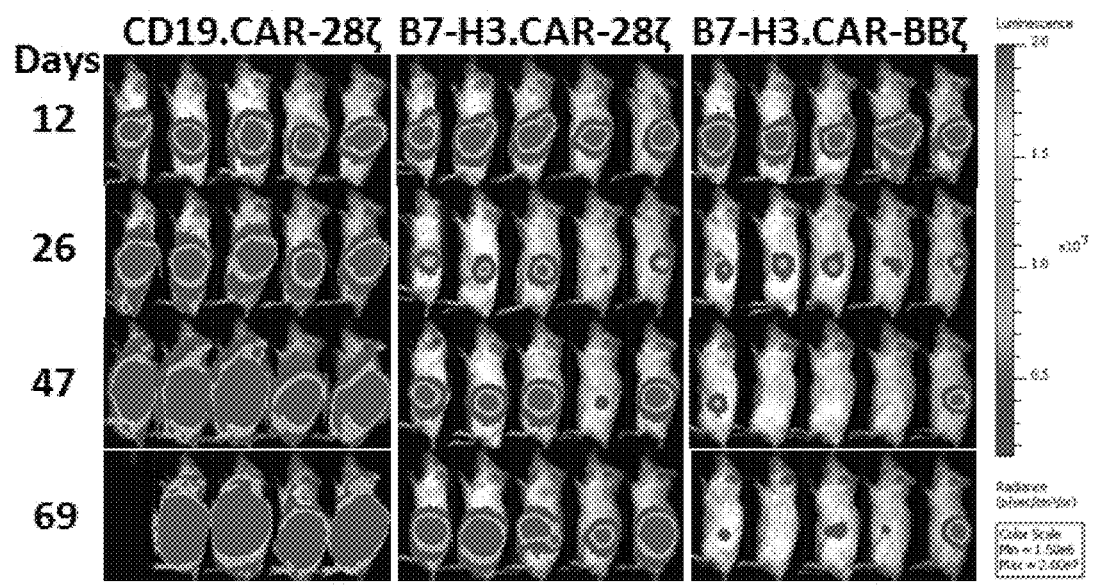
Figure 6F:
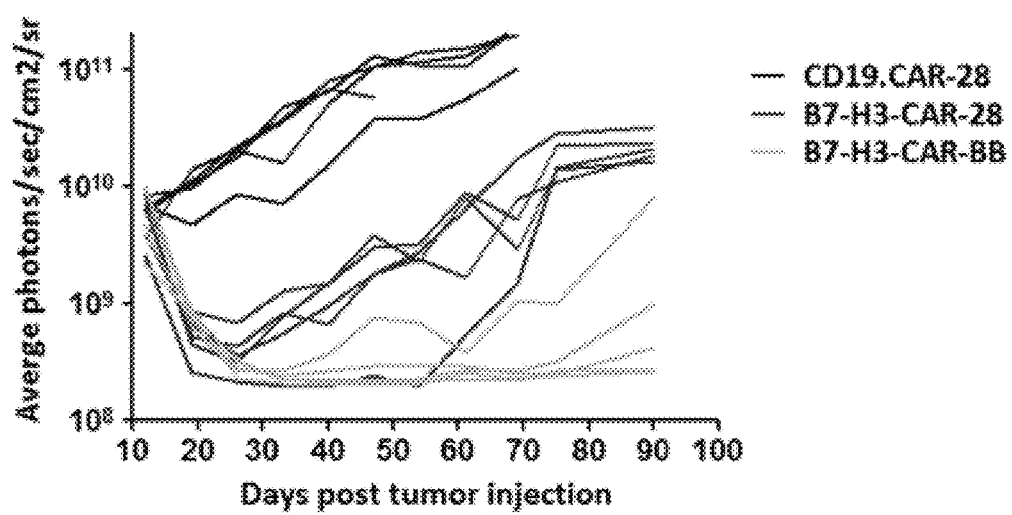
Figure 6G:
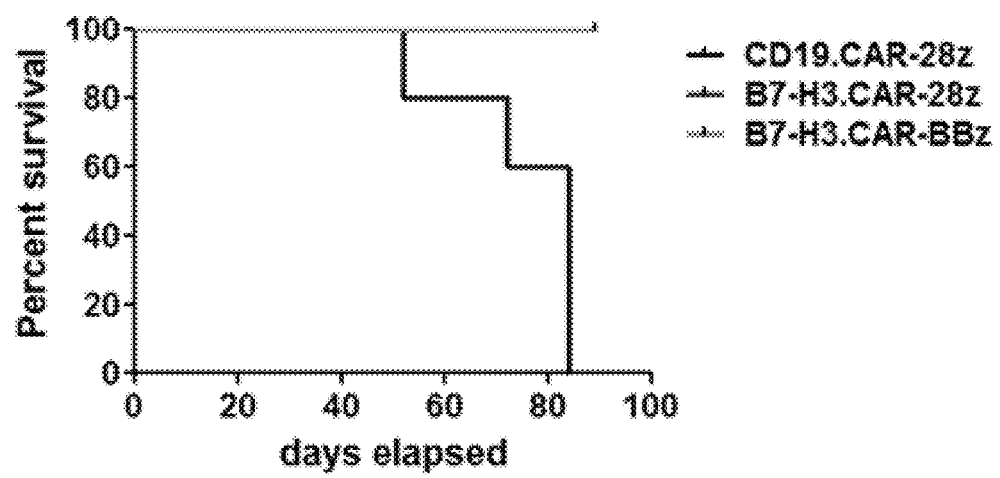
Figure 6H:
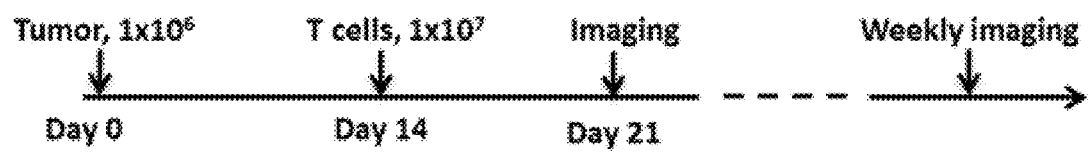

NSG mice were used to assess the in vivo antitumor effect of control and transduced T cells. All mouse experiments were approved by the Institutional Animal Care and Use Committee of University of North Carolina at Chapel Hill. For systemic metastatic model, 8-10-week-old male and female NSG mice (UNC animal facility) were injected i.v. with FFluc transduced either Panc-1 ($1\times10^6$) or BxPC-3 ($1\times10^6$) tumor cells, 14 days after tumor cells inoculation, none-transduced T cell, B7-H3.CAR-28 or B7-H3.CAR-BB T cells were injected i.v. ($1\times10^7$ cells per mouse) (FIG. 6H). For pancreatic orthotopic model, FFluc transduced Panc-1 ($2\times10^5$) or BxPC-3 ($1\times10^5$) tumor cells were suspended in 25 μL DPBS and mixed with 25 μL Matrigel (Corning), then surgically implanted into pancreas of 8-10-week-old male mice using 28-gauge needle. Briefly, an incision is performed in the left flank and tumor cells mixed with Matrigel were injected using a 28-gauge needle into a tail of the pancreas. The wound is closed in two layers, with running 4-0 Vicryl, and wound clips or polypropylene sutures for the skin. 12 days after tumor cells inoculation, CD19.CAR-T (control) or B7-H3.CAR-T cells were injected i.v. ($1\times10^7$ cells per mouse) (FIG. 6A). No randomization was used. Investigators were not blinded, but mice were matched based on the signal of tumor cells before assignment to control or treatment groups. Tumor growth was monitored by bioluminescence imaging weekly using IVIS lumina II in vivo imaging system (PerkinElmer). Mice were euthanized when signs of discomfort were detected by the investigator or as recommended by the veterinarian who monitored the mice three times a week, or when luciferase signal reached $2\times10^{11}$ photons per second per $cm^2$ to investigate animal survival. Tumor specimen was collected and snap froze for IHC staining to detect B7-H3 expression.

Statistical Analyses.

Unless otherwise noted, data were reported as mean±s.d. Student's t-test (two-sided) was used to determine statistically significant differences between samples, with P<0.05 indicating a significant difference. Graph generation and statistical analyses were performed using Prism version 5.0d software (GraphPad, La Jolla, Calif.).

B7-H3 is Highly Expressed on Pancreatic Cancer Tissues but not Normal Human Tissues.

Figure 1B:
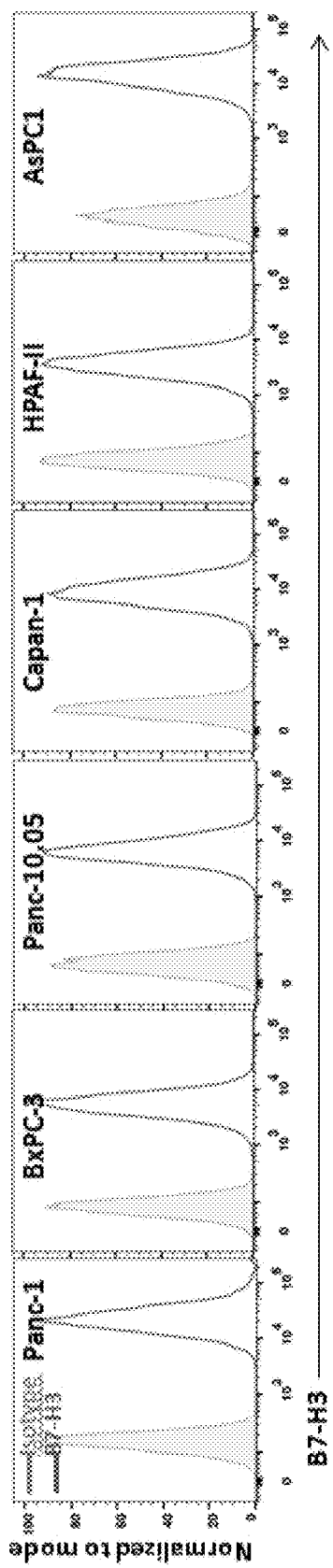
Figure 1C:
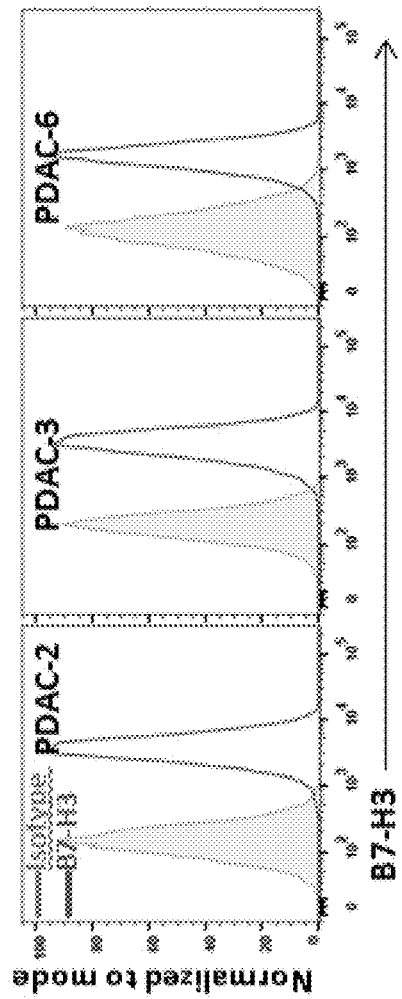
Figure 2:
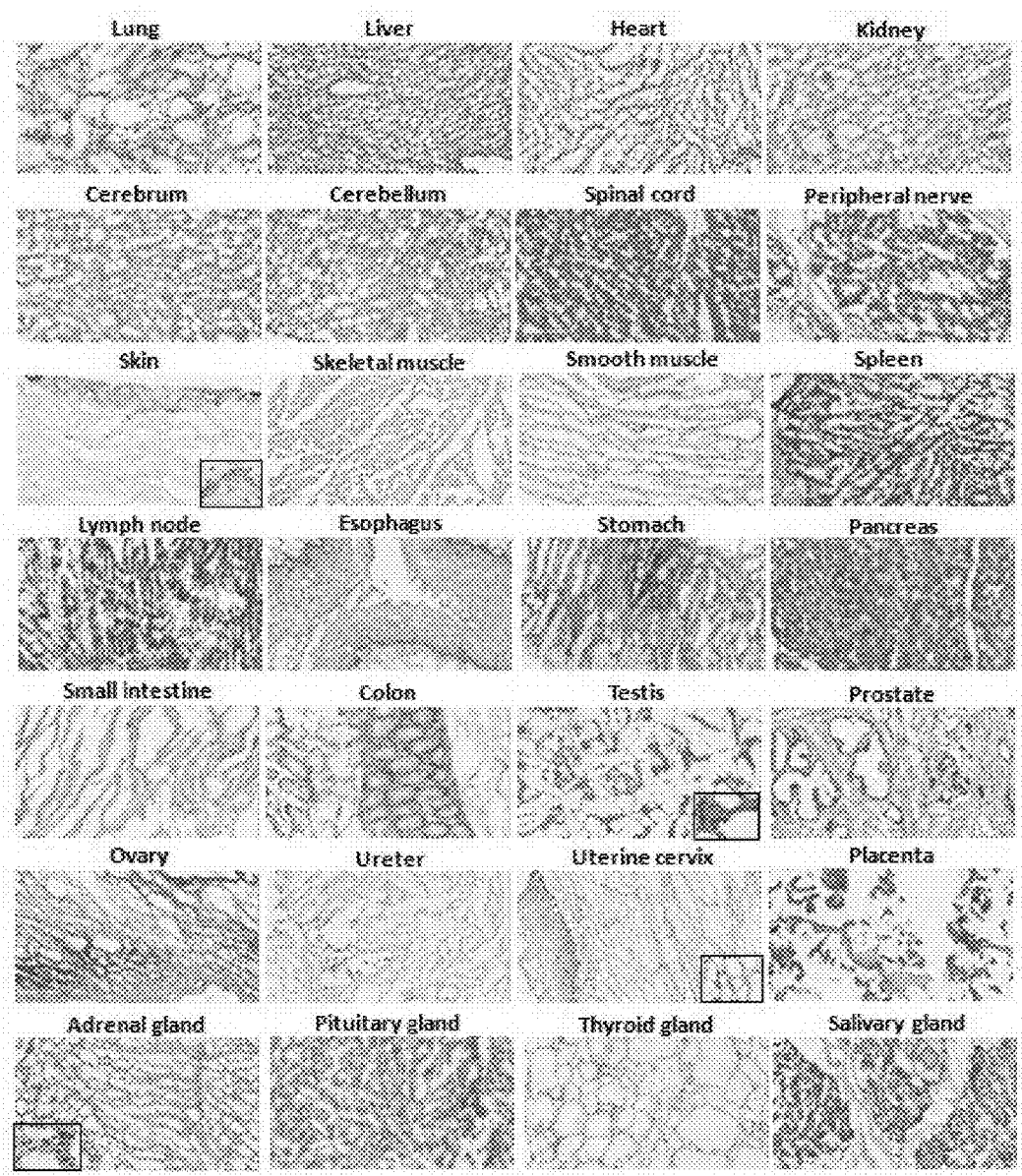
FIG. 2. Limited expression of B7-H3 in normal human tissues. Immunohistochemistry of frozen microarrays of normal human tissues. Staining was performed using the anti-B7-H3 mAb 376.96. The final concentration of the Ab was 1 µg/mL. Representative photomicrographs are shown. Black boxes indicate zoomed in cutout. Data represent at least three sections per tissue. Scale bars are 200 µm.

To evaluate the expression of B7-H3 on normal human tissues, frozen normal human tissue microarray (TMA) slides were stained with the 376.96 mAb. Frozen human pancreatic ductal adenocarcinoma (PDAC) tissues were used as positive control. As shown in FIG. 1A, PDAC tissues were positive for B7-H3, and the antigen is expressed by both tumor cells and stroma fibroblasts, while normal pancreas is B7-H3 negative. Similarly, six human PDAC tumor cell lines and three primary pancreatic tumor cell lines from PDX models are B7-H3 positive (FIGS. 1B-C). Normal human tissues including heart, lung, liver, kidney, spleen, muscle, cerebrum, cerebellum, spinal cord and peripheral nerves were B7-H3 negative (FIG. 2). Weak positivity was detected in adrenal gland, salivary gland, epithelia cells of prostate and basal layer of the skin (FIG. 2).

B7-H3.CAR-Ts Specifically Target B7-H3 Positive Cells and Cross-React with Both Human and Murine B7-H3.

Figure 3B:
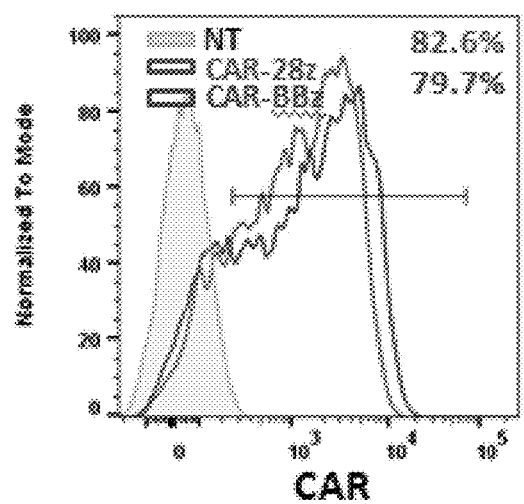
Figure 3C:
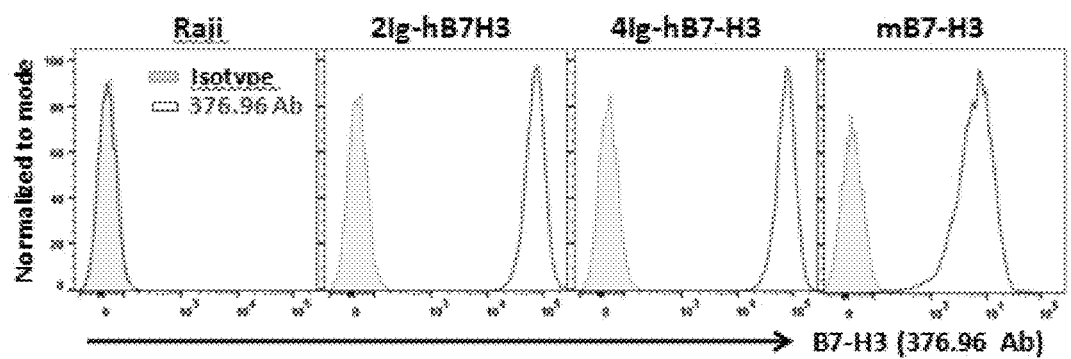
Figure 3D:
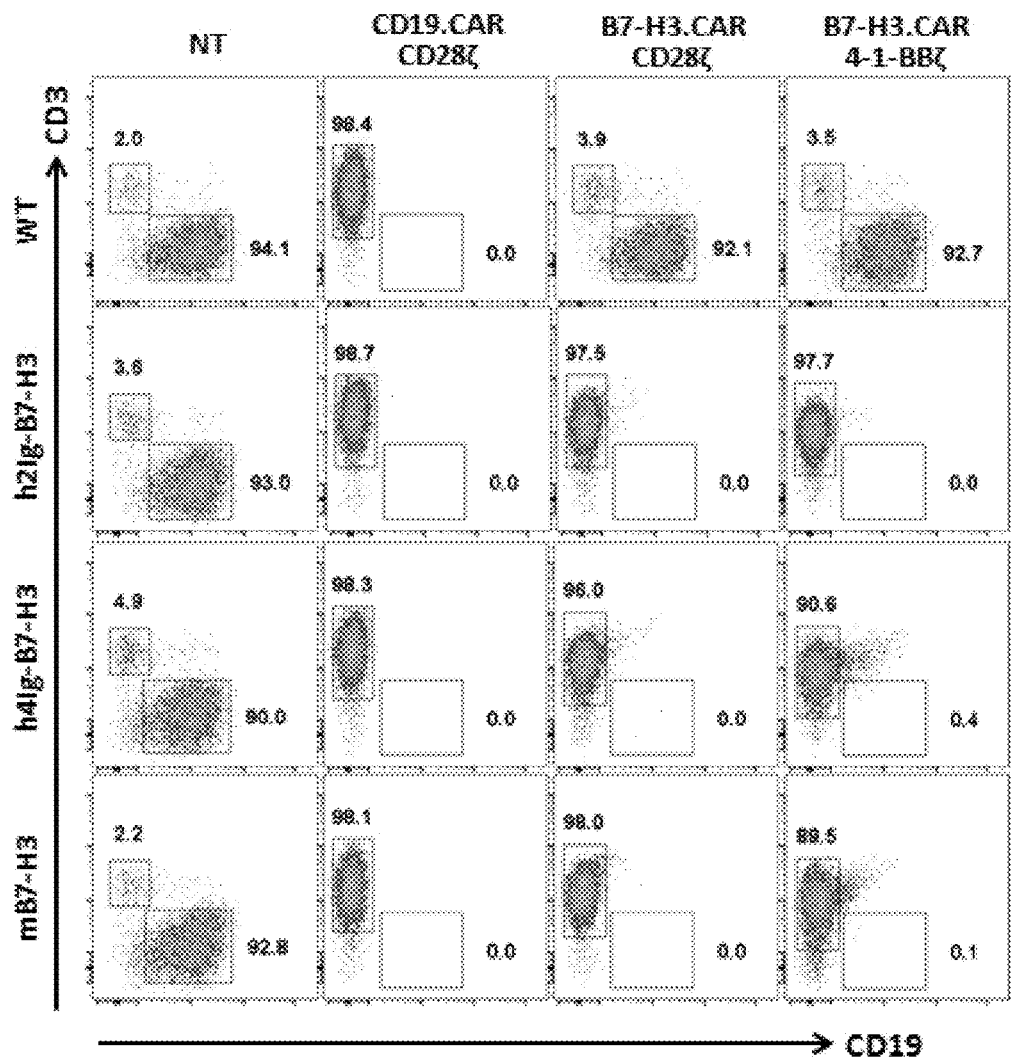
Figure 3E:
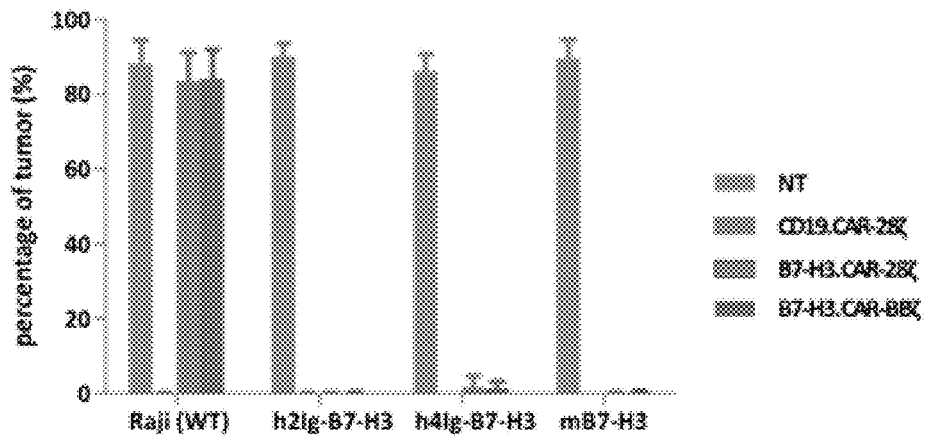
Figure 3F:
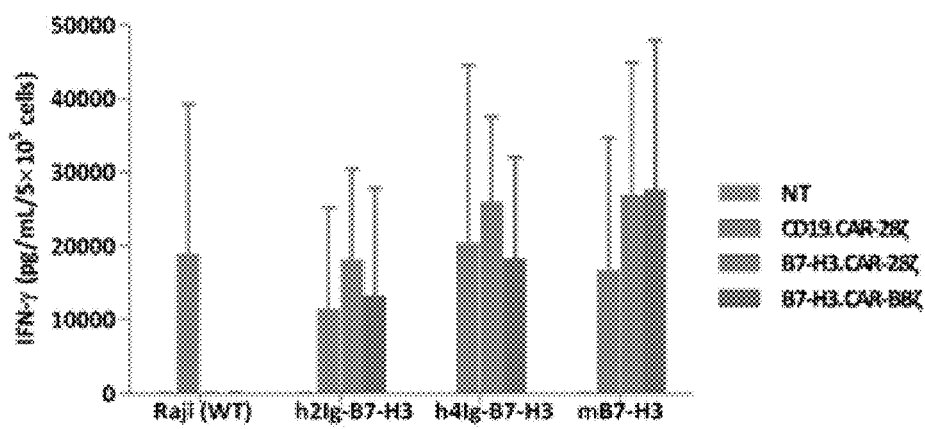
Figure 3G:
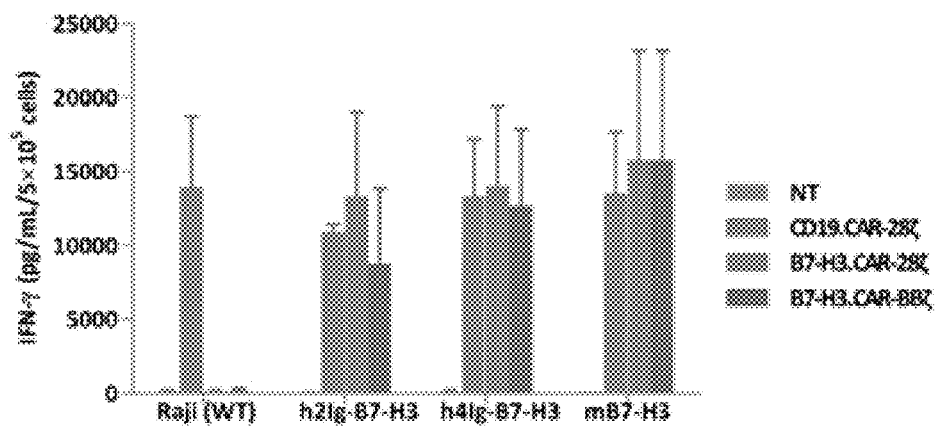

We have generated a B7-H3.CAR using the 376.96 mAb. The scFv sequence obtained from the hybridoma 376.96 was cloned into previously validated CAR formats including the human CD8α hinge and transmembrane domain, CD28 or 4-1-BB intracellular costimulatory domains and CD3ζ intracellular signaling domain. The B7-H3.CAR cassettes were cloned into the retroviral vector SFG and are illustrated in FIG. 3A. The transduction efficiency of B7-H3.CAR-Ts is 65%-85% (FIG. 3B). To verify the specificity of B7-H3.CAR-Ts, the tumor cell line Raji that is B7-H3 negative was genetically modified to express either the two isoforms of human B7-H3 (4Ig-B7-H3 and 2Ig-B7-H3) or the corresponding mouse B7-H3 (mB7-H3). Single cell clones of these cells were obtained (FIG. 3C). Control and B7-H3-expressing Raji cells were then co-cultured with either control or B7-H3.CAR-Ts. As shown in FIG. 3D, B7-H3.CAR-Ts encoding either CD28 or 4-1-BB co-stimulatory domains specifically targeted B7-H3-expressing Raji cells. B7-H3.CAR-Ts also targeted Raji cells expressing mB7-H3 demonstrating that the scFv derived from the 376.96 mAb targets both human and mouse B7-H3 molecule (FIG. 3D-E). The antitumor effect was also parallel by IFNγ and IL-2 release (FIG. 3F-G).

B7-H3.CAR-Ts Target PDAC Cell Lines In Vitro.

Figure 4A:
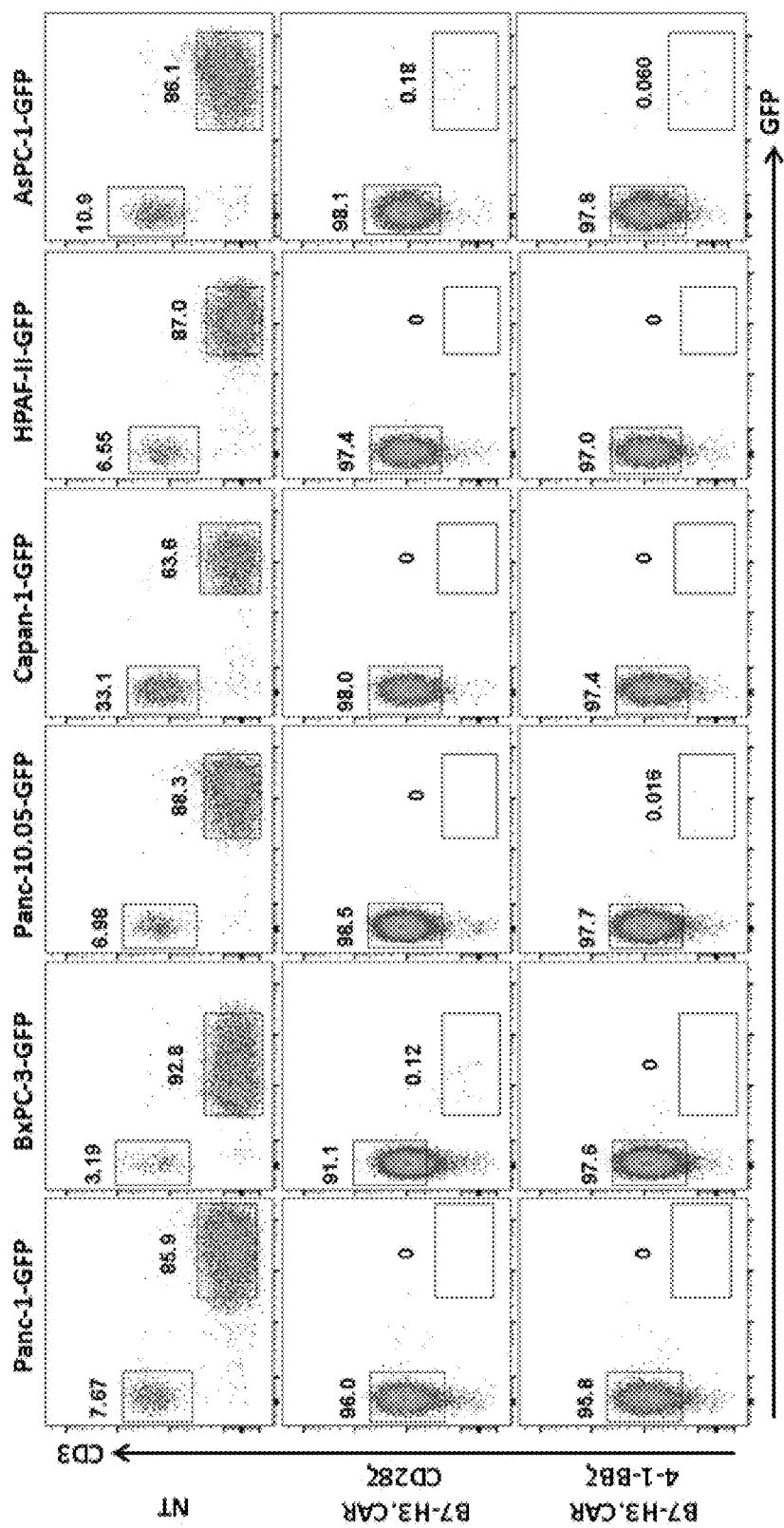
Figure 4B:
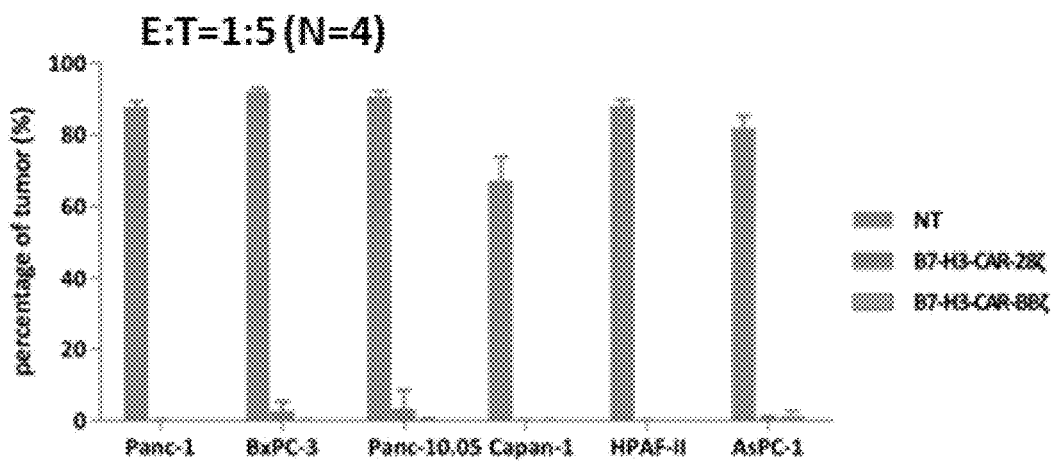
Figure 4C:
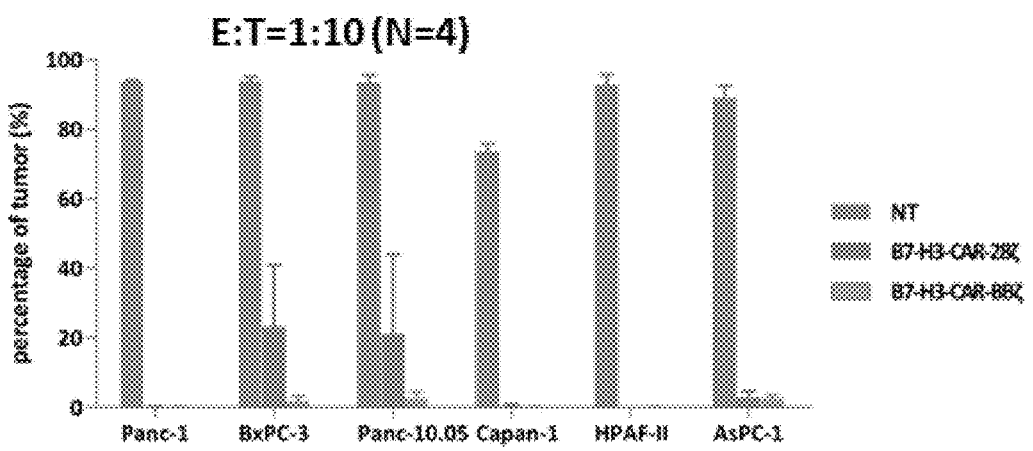
Figure 4D:
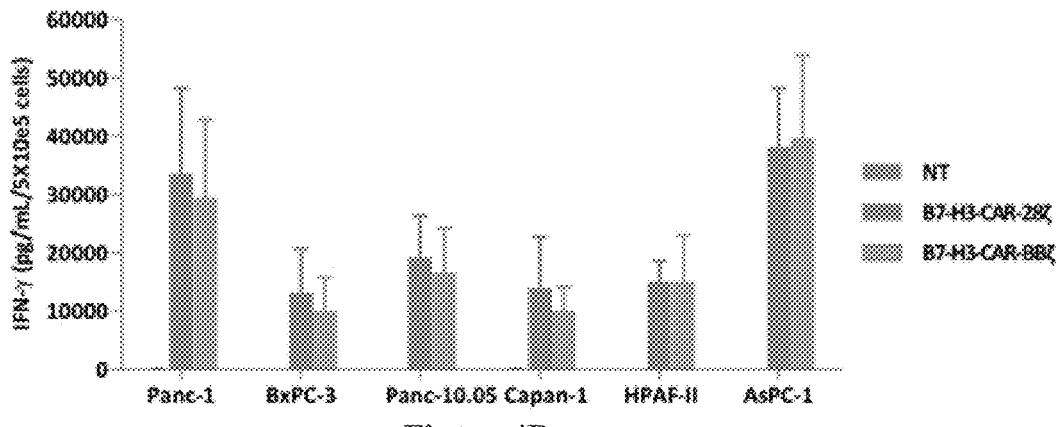
Figure 4E:
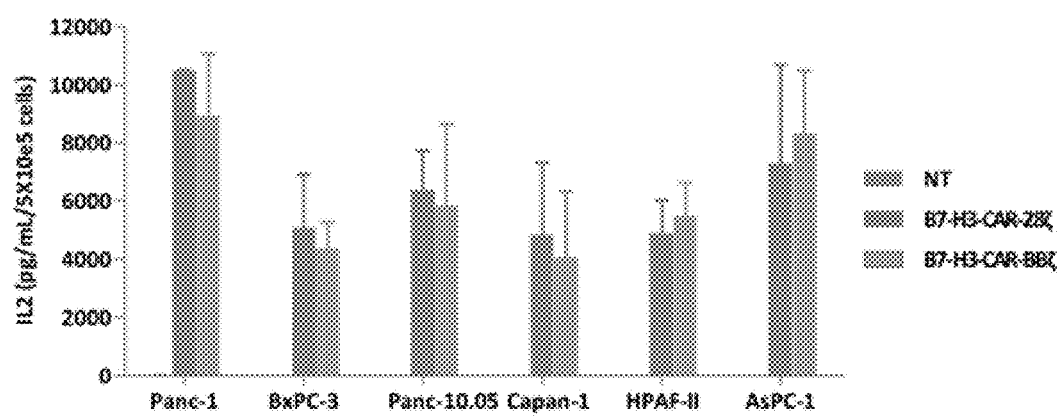
Figure 5A:
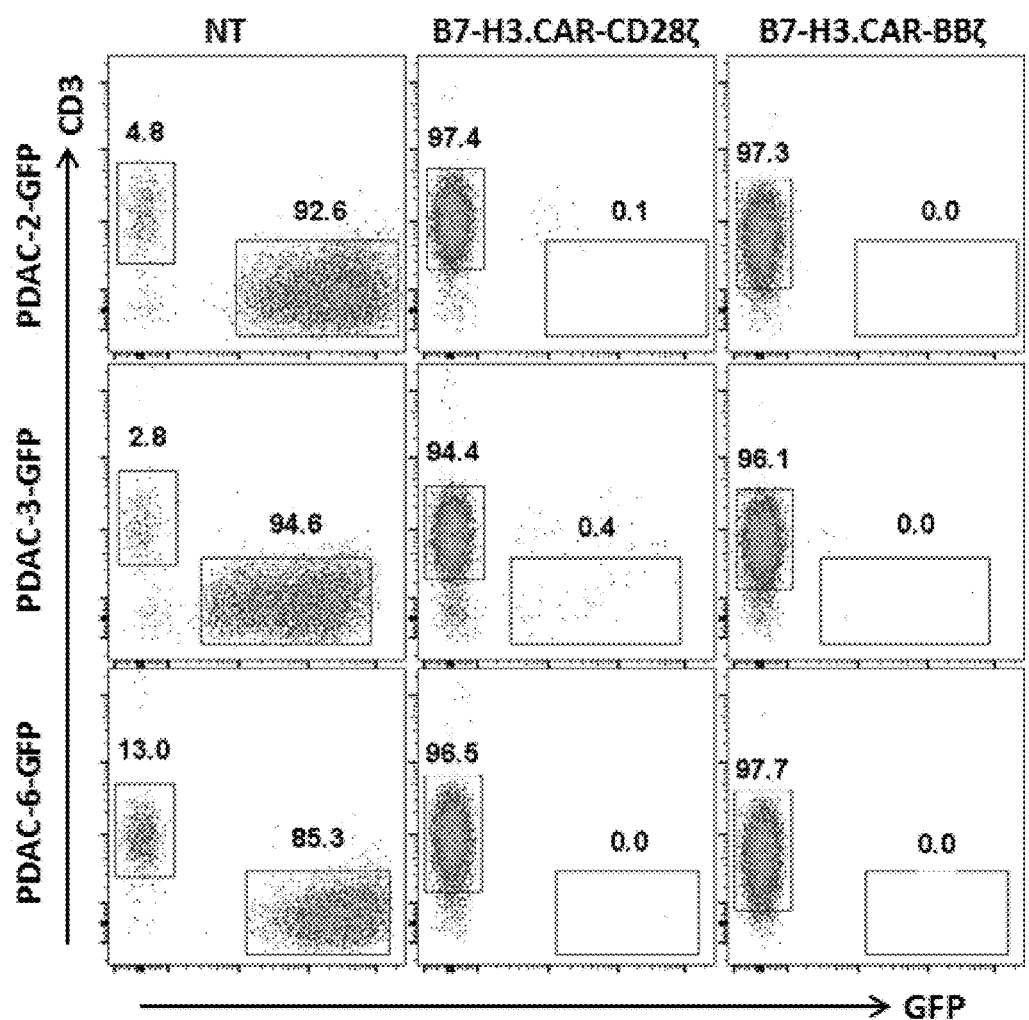
FIGS. 5A-F. B7-H3.CAR-T cells target primary PDAC cell lines derived from PDX. (5A) Three primary PDAC cell lines derived from PDX were co-cultured with control T cells (NT) or B7-H3.CAR-T cells at the T cell to PDAC ratio 1:5. PDAC tumor cell lines were labeled with GFP. By day 7, tumor cells (GFP+) and B7-H3.CAR-T cells (CD3+) were enumerated by flow cytometry. (5B) Statistics of the tumor cell frequency after 7 days co-culture with either control or B7-H3.CAR-T cells for T cell to PDAC ratio 1:5 (n=6), and (5C) for T cell to PDAC ratio 1:10 (n=4). (5D) IFNγ and (5E) IL2 released by either T cells or B7-H3.CAR-Ts after 24 hours of co-cultured with PDAC as measured by ELISA (n=4). (5F) CFSE-labeled B7-H3.CAR-T cells were co-cultured with PDAC for 5 days at 1:1 ratio. Proliferation of B7-H3.CAR-T cells was measured by CFSE dilution and analyzed by flow cytometry. CFSE-labeled B7-H3.CAR-T cells alone were used as control, which is shown as filled gray peak.
Figure 5B:
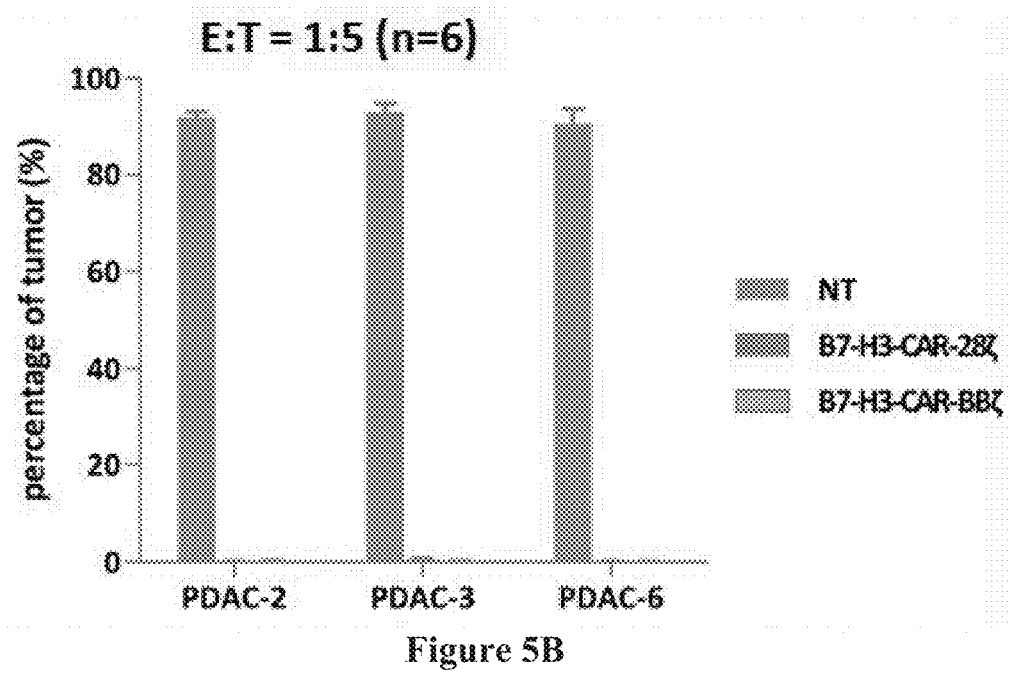
Figure 5C:
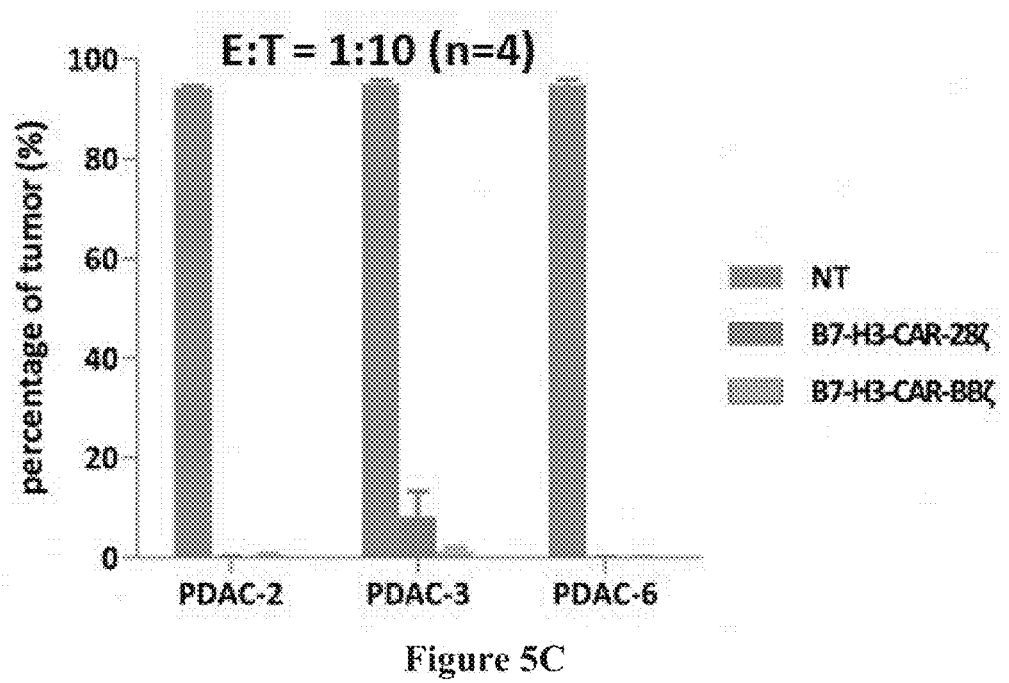
Figure 5D:
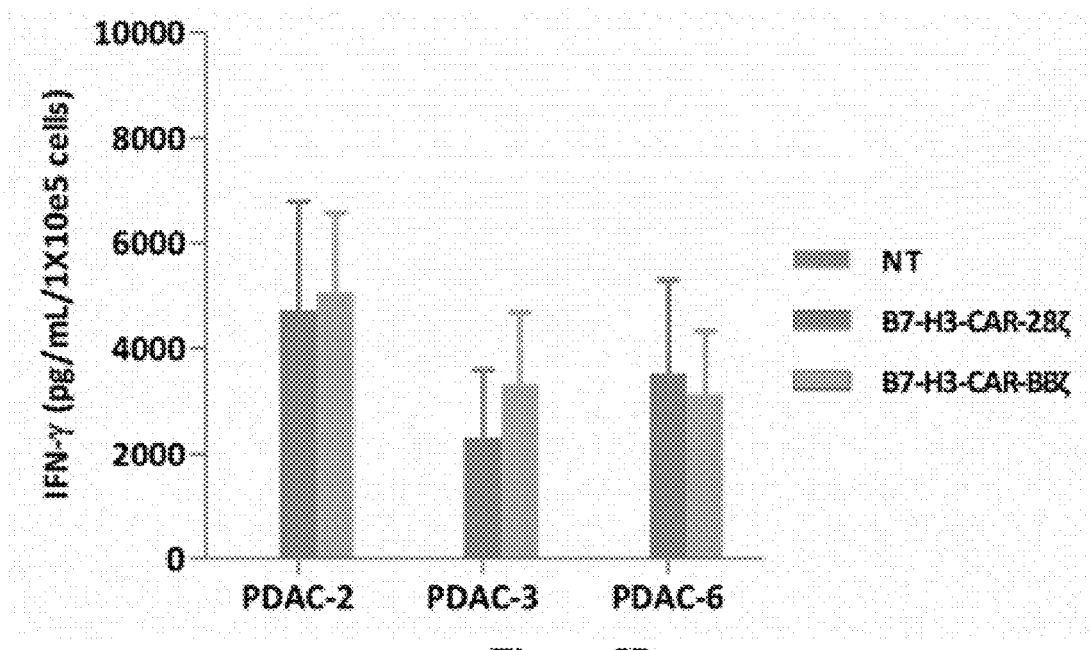
Figure 5E:
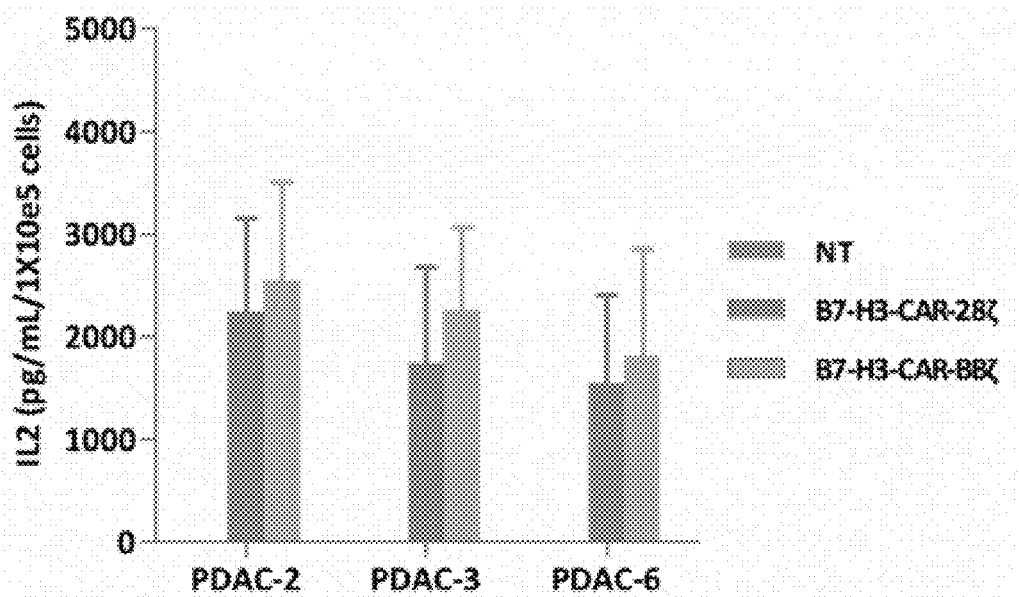
Figure 5F:
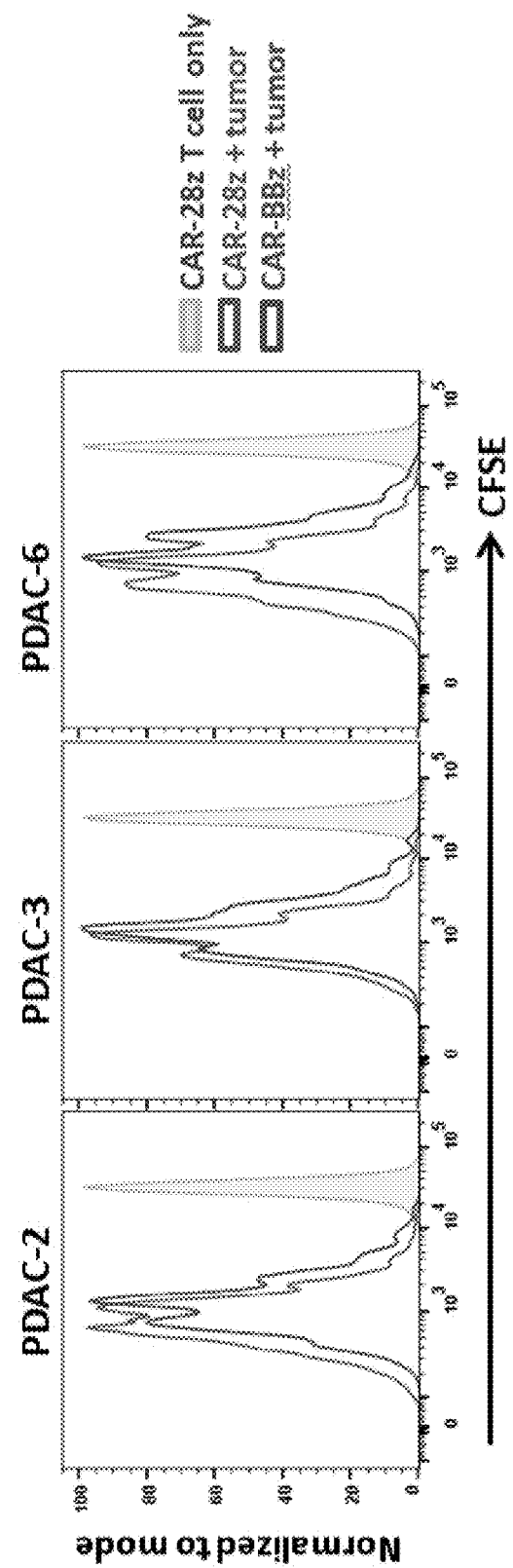

To assess the effects of B7-H3.CAR-Ts on tumor cell lines naturally expressing B7-H3, we co-cultured six PDAC cell lines with CD19.CAR-Ts (negative control) and B7-H3.CAR-Ts at different T cell to tumor cell ratios. As shown in FIG. 4A, B7-H3.CAR-Ts effectively eliminated PDAC cells, even at 1:10 T cell to tumor cell ratio (FIG. 4B-C). For two PDAC tumor cell lines, BxPC-3 and Panc-10.05, B7-H3.CAR-Ts encoding 4-1BB seemed more efficient than B7-H3.CAR-Ts encoding CD28 (FIG. 4C). Cytolytic activity of B7-H3.CAR-Ts was corroborated by cytokine release (IFNγ and IL2) (FIG. 4D-E) and proliferation (FIG. 4F). Similar results were obtained when B7-H3.CAR-Ts were co-cultured with PDAC cell lines derived from PDX (FIG. 5A-F).

B7-H3.CAR-Ts Show Antitumor Activity in Xenograft Models.

Figure 6I:
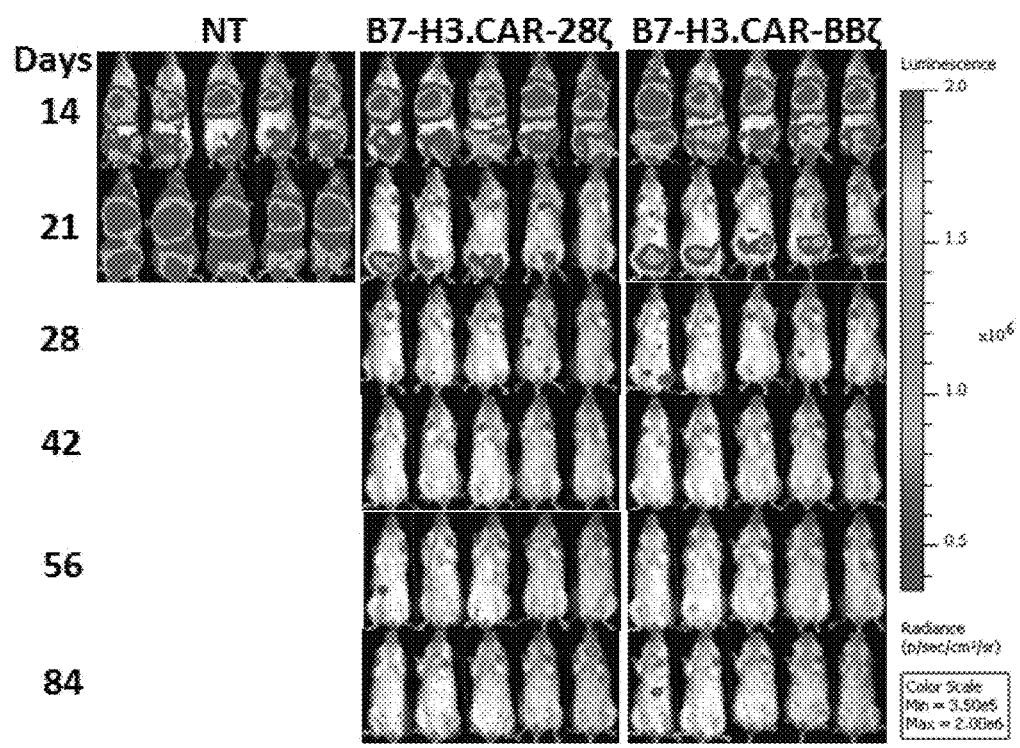
Figure 6J:
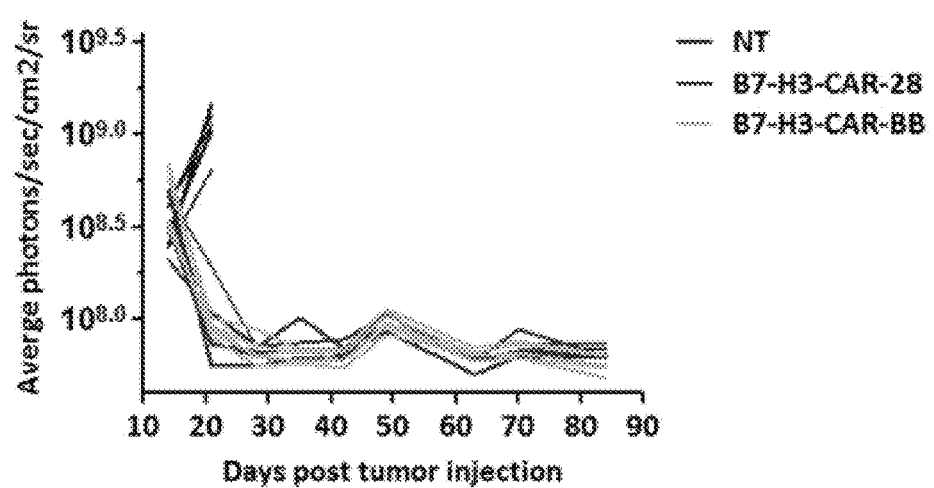
Figure 7:
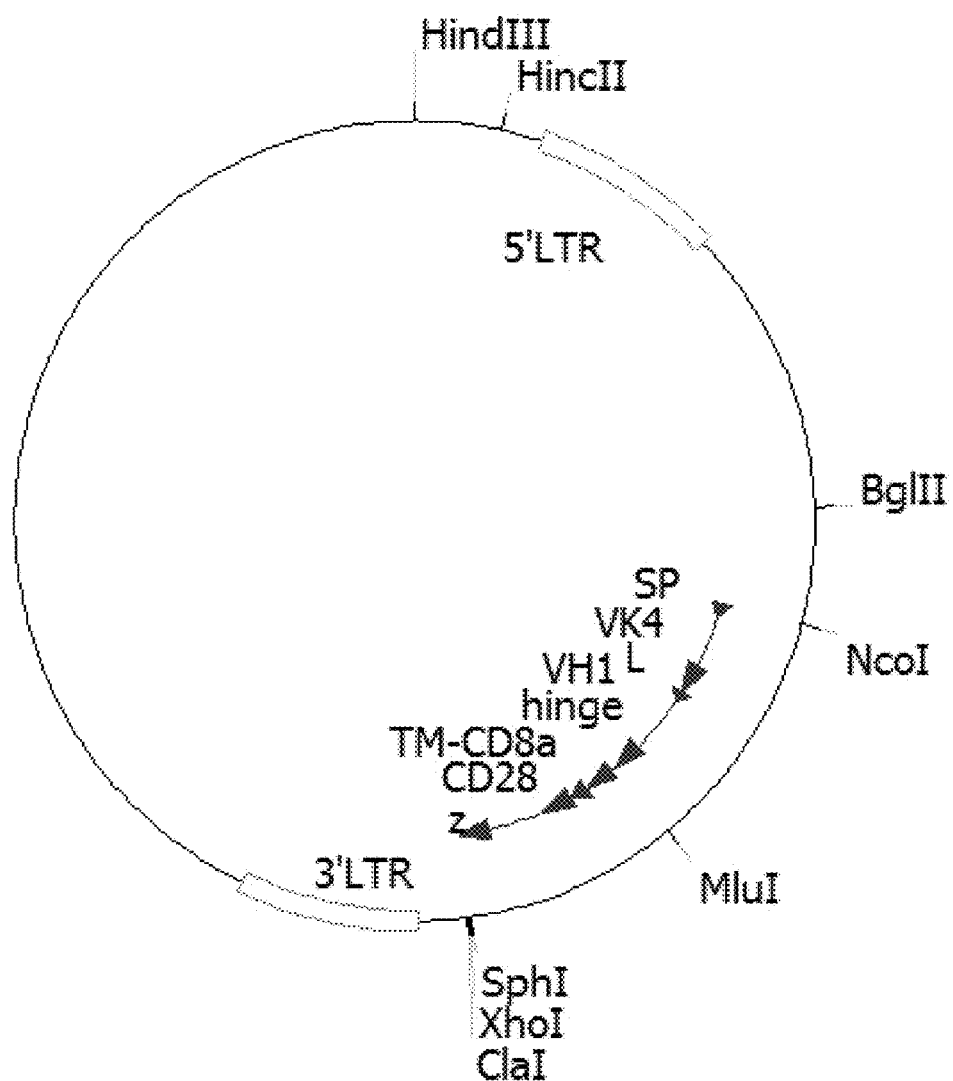
FIG. 7. Plasmid map and nucleotide sequence of plasmid encoding CD28 version of CAR (SEQ ID NO:3) with translation into amino acid sequence (SEQ ID NO:1).
Figure 8:
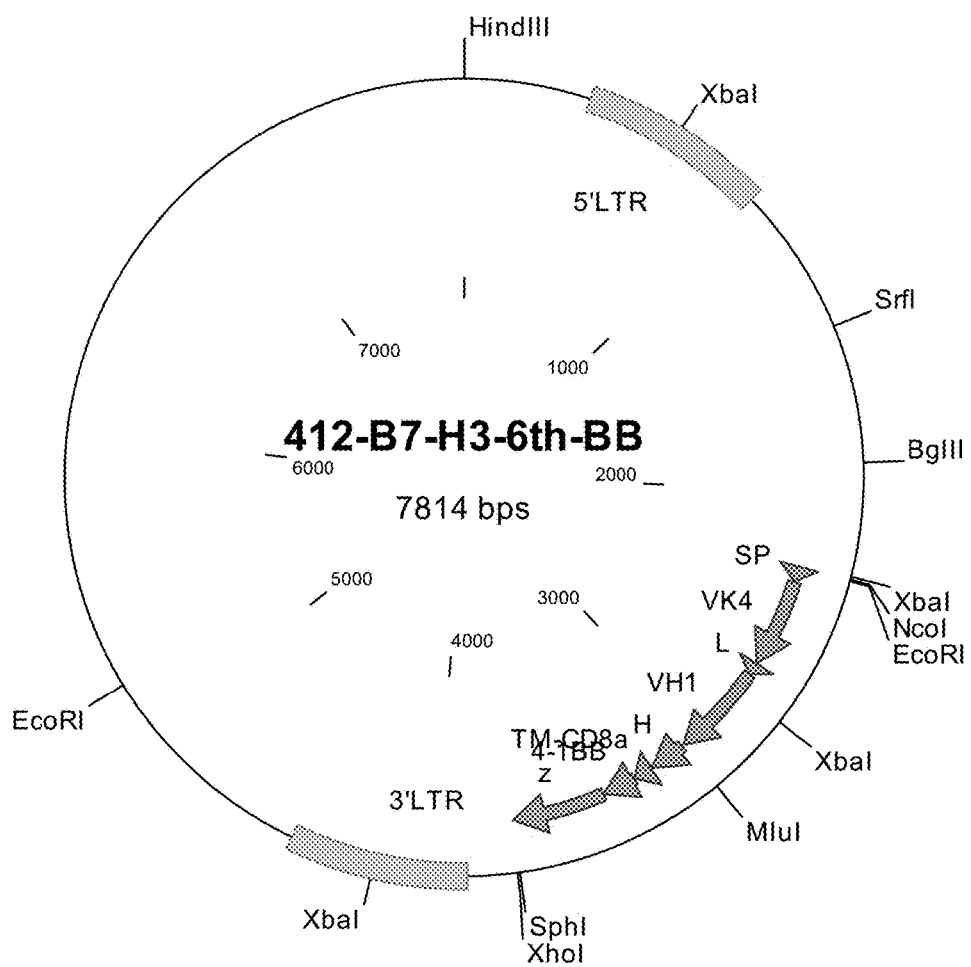
FIG. 8. Plasmid map and nucleotide sequence of plasmid encoding 4-1-BB version of CAR (SEQ ID NO:4) with translation into amino acid sequence (SEQ ID NO:2).

To investigate the antitumor effects of B7-H3.CAR-Ts in vivo, FFluc transduced Panc-1 and BxPC-3 tumor cells were implanted into pancreas of NSG mice by surgery for pancreas orthotopic models, and treated with control CD19.CAR-Ts and B7-H3.CAR-Ts (FIG. 6A). As shown in FIG. 6B-D, B7-H3.CAR-Ts effectively eliminated Panc-1 tumor cells and mice remained tumor free up to day 80 after treatment. In the BxPC-3 orthotopic model, B7-H3.CAR-Ts also controlled tumor but in this model B7-H3.CAR-Ts encoding 4-1BB were more effective than B7-H3.CAR-Ts encoding CD28 (FIG. 6E-G). In metastatic model, FFluc transduced Panc-1 tumor cell was implanted into NSG mice by i.v. injection (FIG. 6H). Mice were then treated via tail vein injection with CD19.CAR-Ts and B7-H3.CAR-Ts. As shown in FIG. 6I-J, B7-H3.CAR-Ts controlled Panc-1 tumor growth until day 70 post treatment when the experiment was terminated. In this model both B7-H3.CAR-Ts encoding either CD28 or 4-1BB showed similar activity.

All publications, patent applications, patents, patent publications and other references cited herein are incorporated by reference in their entireties for the teachings relevant to the sentence and/or paragraph in which the reference is presented.

scFV sequence of B7-H3-CAR (SEQ ID NO: 5)
GACATTGTGATGACCCAGTCTCACAAATTCATGTCCACATCAATTGGAGC

CAGGGTCAGCATCACCTGCAAGGCCAGTCAGGATGTGAGAACTGCTGTAG

CCTGGTATCAACAGAAACCAGGCCAGTCTCCTAAACTACTAATTTACTCG

GCATCCTACCGGTACACTGGAGTCCCTGATCGCTTCACTGGCAGTGGATC

TGGGACGGATTTCACTTTCACCATCAGCAGTGTGCAGGCTGAAGACCTGG

-continued

CAGTTTATTACTGTCAGCAACATTATGGTACTCCTCCGTGGACGTTCGGT

GGAGGCACCAAGCTGGAAATCAAAGGCGGCGGAGGATCTGGCGGAGGCGG

AAGTGGCGGAGGGGGCTCTGAAGTGCAGCTGGTGGAGTCTGGGGGAGGCT

TAGTGAAGCCTGGAGGGTCCCTGAAACTCTCCTGTGAAGCCTCTAGATTC

ACTTTCAGTAGCTATGCCATGTCTTGGGTTCGCCAGACTCCGGAGAAGAG

GCTGGAGTGGGTCGCAGCCATTAGTGGAGGTGGTAGGTACACCTACTATC

CAGACAGTATGAAGGGTCGATTCACCATCTCCAGAGACAATGCCAAGAAT

TTCCTGTACCTGCAAATGAGCAGTCTGAGGTCTGAGGACACGGCCATGTA

TTACTGTGCAAGACACTATGATGGTTATCTTGACTACTGGGGCCAAGGCA

CCACTCTCACAGTCTCCTCA

---

That which is claimed is:

1. A method of stimulating a T cell-mediated immune response to a B7-H3 expressing target cell population or tissue in a subject, comprising administering to the subject an effective amount of a cell comprising a CAR comprising:
   a) a signal peptide;
   b) a light chain variable region comprising the amino acid sequence:

(SEQ ID NO: 6)
   DIVMTQSHKFMSTSIGARVSITCKASQDVRTAVAWYQQKPGQSPKLLIYS

ASYRYTGVPDRFTGSGSGTDFTFTISSVQAEDLAVYYCQQHYGTPPWTFG

GGTKLEIK;

c) a linker peptide;
   d) a heavy chain variable region comprising the amino acid sequence:

(SEQ ID NO: 7)
   EVQLVESGGGLVKPGGSLKLSCEASRFTFSSYAMSWVRQTPEKRLEWVAA

ISGGGRYTYYPDSMKGRFTISRDNAKNFLYLQMSSLRSEDTAMYYCARHY

DGYLDYWGQGTTLTVSS;

e) a CD8α hinge polypeptide;
   f) a CD8α transmembrane domain;
   g) a 4-1BB or CD28 costimulatory domain; and
   h) a CD3ζ signaling domain;
   thereby stimulating a T cell-mediated immune response to the B7-H3 expressing target cell population or tissue in the subject.

2. The method of claim 1, wherein the cell is an autologous cell.

3. The method of claim 1, wherein the CAR further comprises a detectable moiety.

4. The method of claim 1, wherein the CAR further comprises an effector molecule selected from the group consisting of a drug, a toxin, a small molecule, an antibody, a cytokine, an oncolytic virus, an enzyme, a nanoparticle, a biomaterial, a scaffold and any combination thereof.

5. The method of claim 1, wherein the cell is selected from the group consisting of a αβT cell, a natural killer (NK) cell, a cytotoxic T lymphocyte (CTL), a regulatory T cell, a natural killer T (NKT) cell, a Th17 cell, a γδT cell and any combination thereof.

6. A method of treating a subject having a disease or disorder associated with elevated expression of B7-H3 (CD276) by a cell of the subject, comprising administering to the subject an effective amount of a cell comprising a chimeric antigen receptor (CAR) comprising:
   a) a signal peptide;
   b) a light chain variable region comprising the amino acid sequence:

(SEQ ID NO: 6)
   DIVMTQSHKFMSTSIGARVSITCKASQDVRTAVAWYQQKPGQSPKLLIYS

ASYRYTGVPDRFTGSGSGTDFTFTISSVQAEDLAVYYCQQHYGTPPWTFG

GGTKLEIK;

c) a linker peptide;
   d) a heavy chain variable region comprising the amino acid sequence:

(SEQ ID NO: 7)
   EVQLVESGGGLVKPGGSLKLSCEASRFTFSSYAMSWVRQTPEKRLEWVAA

ISGGGRYTYYPDSMKGRFTISRDNAKNFLYLQMSSLRSEDTAMYYCARHY

DGYLDYWGQGTTLTVSS;

e) a CD8α hinge polypeptide;
   f) a CD8α transmembrane domain;
   g) a 4-1BB or CD28 costimulatory domain; and
   h) a CD3ζ signaling domain;
   thereby treating the subject having the disease or disorder associated with elevated expression of B7-H3 by the cell of the subject.

7. The method of claim 6, wherein the cell comprising the CAR is an autologous cell.

8. The method of claim 6, wherein the disease or disorder is cancer.

9. The method of claim 6, wherein the CAR further comprises a detectable moiety.

10. The method of claim 6, wherein the CAR further comprises an effector molecule selected from the group consisting of a drug, a toxin, a small molecule, an antibody, a cytokine, an oncolytic virus, an enzyme, a nanoparticle, a biomaterial, a scaffold and any combination thereof.

11. The method of claim 6, wherein the cell comprising the CAR is selected from the group consisting of a αβT cell, a natural killer (NK) cell, a cytotoxic T lymphocyte (CTL), a regulatory T cell, a natural killer T (NKT) cell, a Th17 cell, a γδT cell and any combination thereof.

12. A method of targeting a cancer cell and/or a cancer initiating cell (CIC) having a B7-H3 (CD276) antigen, comprising contacting the cancer cell and/or the CIC with a cell comprising a CAR comprising:
   a) a signal peptide;
   b) a light chain variable region comprising the amino acid sequence:

(SEQ ID NO: 6)
   DIVMTQSHKFMSTSIGARVSITCKASQDVRTAVAWYQQKPGQSPKLLIYS

ASYRYTGVPDRFTGSGSGTDFTFTISSVQAEDLAVYYCQQHYGTPPWTFG

GGTKLEIK;

c) a linker peptide;
d) a heavy chain variable region comprising the amino acid sequence:

(SEQ ID NO: 7)
EVQLVESGGGLVKPGGSLKLSCEASRFTFSSYAMSWVRQTPEKRLEWVAA

ISGGGRYTYYPDSMKGRFTISRDNAKNFLYLQMSSLRSEDTAMYYCARHY

DGYLDYWGQGTTLTVSS;

e) a CD8α hinge polypeptide;
f) a CD8α transmembrane domain;
g) a 4-1BB or CD28 costimulatory domain; and
h) a CD3ζ signaling domain.

13. The method of claim 12, wherein the cancer cell and/or CIC is in vitro or in vivo.

14. The method of claim 12, wherein the cell is an autologous cell.

15. The method of claim 12, wherein the CAR further comprises a detectable moiety.

16. The method of claim 12, wherein the CAR further comprises an effector molecule selected from the group consisting of a drug, a toxin, a small molecule, an antibody, a cytokine, an oncolytic virus, an enzyme, a nanoparticle, a biomaterial, a scaffold and any combination thereof.

17. The method of claim 12, wherein the cell is selected from the group consisting of a αβT cell, a natural killer (NK) cell, a cytotoxic T lymphocyte (CTL), a regulatory T cell, a natural killer T (NKT) cell, a Th17 cell, a γδT cell and any combination thereof.

18. A method of detecting cancer cells and/or cancer initiating cells (CICs) having a B7-H3 (CD276) antigen in a cell population, comprising:
a) contacting the cell population with a CAR comprising:
a) a signal peptide;
b) a light chain variable region comprising the amino acid sequence:

(SEQ ID NO: 6)
DIVMTQSHKFMSTSIGARVSITCKASQDVRTAVAWYQQKPGQSPKLLIYS

ASYRYTGVPDRFTGSGSGTDFTFTISSVQAEDLAVYYCQQHYGTPPWTFG

GGTKLEIK;

c) a linker peptide;
d) a heavy chain variable region comprising the amino acid sequence:

(SEQ ID NO: 7)
EVQLVESGGGLVKPGGSLKLSCEASRFTFSSYAMSWVRQTPEKRLEWVAA

ISGGGRYTYYPDSMKGRFTISRDNAKNFLYLQMSSLRSEDTAMYYCARHY

DGYLDYWGQGTTLTVSS;

e) a CD8α hinge polypeptide;
f) a CD8α transmembrane domain;
g) a 4-1BB or CD28 costimulatory domain; and
h) a CD3ζ signaling domain;
under conditions whereby a binding complex can form; and
b) detecting formation of the binding complex, thereby detecting cancer cells and/or cancer initiating cells (CICs) having a B7-H3 (CD276) antigen in the cell population.

19. The method of claim 18, wherein the cancer cell and/or CIC is in vitro or in vivo.

20. The method of claim 18, wherein the cell population is in a subject.

21. The method of claim 18, wherein the CAR further comprises a detectable moiety.

22. The method of claim 18, wherein the CAR further comprises an effector molecule selected from the group consisting of a drug, a toxin, a small molecule, an antibody, a cytokine, an oncolytic virus, an enzyme, a nanoparticle, a biomaterial, a scaffold and any combination thereof.

* * * * *